US009176150B2

(12) United States Patent
Hillen et al.

(10) Patent No.: US 9,176,150 B2
(45) Date of Patent: *Nov. 3, 2015

(54) AMYLOID BETA(1-42) OLIGOMERS, DERIVATIVES THEREOF AND ANTIBODIES THERETO, METHODS OF PREPARATION THEREOF AND USE THEREOF

(75) Inventors: Heinz Hillen, Hassloch (DE); Andreas Striebinger, Speyer (DE); Carsten Krantz, Allschwll (DE); Achim Moeller, Grunstadt (DE); Reinhold Mueller, Schifferstadt (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/195,533

(22) Filed: Aug. 1, 2011

(65) Prior Publication Data

US 2012/0034166 A1 Feb. 9, 2012

Related U.S. Application Data

(60) Continuation of application No. 12/559,255, filed on Sep. 14, 2009, now abandoned, which is a division of application No. 10/543,841, filed as application No. PCT/EP2004/000927 on Feb. 2, 2004, now Pat. No. 7,902,328.

(30) Foreign Application Priority Data

Jan. 31, 2003 (DE) .................................. 103 03 974

(51) Int. Cl.
*C07K 16/18* (2006.01)
*G01N 33/68* (2006.01)
*A61K 38/17* (2006.01)
*C07K 14/47* (2006.01)
*G01N 33/53* (2006.01)
*A61K 39/395* (2006.01)

(52) U.S. Cl.
CPC ........ *G01N 33/6896* (2013.01); *A61K 38/1709* (2013.01); *C07K 14/4711* (2013.01); *C07K 16/18* (2013.01)

(58) Field of Classification Search
CPC ............... C07K 16/18; C07K 14/4711; C07K 2317/76; G01N 33/6896; G01N 2800/2821; G01N 2333/4709; A61K 2039/505; A61K 39/3955; A61K 38/17
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,526,938 A | 7/1985 | Churchill et al. |
| 4,582,788 A | 4/1986 | Erlich |
| 4,634,665 A | 1/1987 | Axel et al. |
| 4,666,829 A | 5/1987 | Glenner et al. |
| 4,683,194 A | 7/1987 | Saiki et al. |
| 4,683,202 A | 7/1987 | Mullis |
| 4,816,397 A | 3/1989 | Boss et al. |
| 4,816,567 A | 3/1989 | Cabilly et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,107,065 A | 4/1992 | Shewmaker et al. |
| 5,128,326 A | 7/1992 | Balazs et al. |
| 5,134,062 A | 7/1992 | Blass |
| 5,168,062 A | 12/1992 | Stinski |
| 5,179,017 A | 1/1993 | Axel et al. |
| 5,218,100 A | 6/1993 | Muller-Hill et al. |
| 5,223,409 A | 6/1993 | Ladner et al. |
| 5,225,539 A | 7/1993 | Winter |
| 5,231,000 A | 7/1993 | Majocha et al. |
| 5,231,020 A | 7/1993 | Jorgensen et al. |
| 5,231,170 A | 7/1993 | Averback |
| 5,234,814 A | 8/1993 | Card et al. |
| 5,258,498 A | 11/1993 | Huston et al. |
| 5,262,332 A | 11/1993 | Selkoe |
| 5,290,540 A | 3/1994 | Prince et al. |

(Continued)

FOREIGN PATENT DOCUMENTS

| | | |
|---|---|---|
| AU | 2007200047 | 1/2007 |
| CA | 2541522 | 9/2007 |

(Continued)

OTHER PUBLICATIONS

Terryberry et al. (1998) Neurobiology Aging, 19(3):205-216.*
Barghorn, S. et al., "Globular amyloid beta-peptide 1-42 oligomer—a homogeneous and stable neuropathological protein in Alzheimer's disease," J. Neurochem. (2005) 95(1):834-847.
Chromy, B. et al., "Self-assembly of a beta 1-42 into globular neurotoxins," Biochem. (2003) 42(17):12749-12760.
Chromy et al., "Oligomer/conformation-dependent Abeta antibodies," Abstracts of the Annual Meeting of the Society for Neuroscience (2000) 26(1-2):4.
Gellermann, G.P. et al., "Abeta-globulomers are formed independently of the fibril pathway," Neurobiol. Of Dis. (2008) 30(2):212-220.

(Continued)

*Primary Examiner* — Kimberly A Ballard
(74) *Attorney, Agent, or Firm* — Lisa V. Mueller; Michael Best & Friedrich LLP

(57) ABSTRACT

The invention relates to neuromodulatory oligomers of the amyloid-β(1-42) protein, a particular production method, by means of which the oligomer can be obtained in a reproducible manner at high yield, the use of the oligomers as diagnostic and therapeutics agents, for the generation of oligomer-specific antibodies and for the discovery of substances which can interact with the oligomers and in the formation thereof. Corresponding methods for the production of the antibodies and for discovery of the substances are also disclosed as are the antibodies themselves and the use of the antibodies or substances as diagnostic and therapeutic agents. The invention further relates to derivatives of the oligomers and oligomers based on abbreviated forms of the amyloid-β (1-42) proteins, the production and use thereof.

12 Claims, 15 Drawing Sheets

(56) References Cited

U.S. PATENT DOCUMENTS

| | | |
|---|---|---|
| 5,403,484 A | 4/1995 | Ladner et al. |
| 5,427,908 A | 6/1995 | Dower et al. |
| 5,441,870 A | 8/1995 | Seubert et al. |
| 5,455,169 A | 10/1995 | Mullan |
| 5,516,637 A | 5/1996 | Huang et al. |
| 5,530,101 A | 6/1996 | Queen et al. |
| 5,538,845 A | 7/1996 | Knops et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,567,720 A | 10/1996 | Averback |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,846 A | 1/1997 | Schenk et al. |
| 5,605,811 A | 2/1997 | Seubert et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,665,355 A | 9/1997 | Primi |
| 5,679,377 A | 10/1997 | Bernstein et al. |
| 5,679,531 A | 10/1997 | Konig |
| 5,693,753 A | 12/1997 | Konig |
| 5,693,762 A | 12/1997 | Queen et al. |
| 5,698,426 A | 12/1997 | Huse |
| 5,705,330 A | 1/1998 | Shah et al. |
| 5,705,401 A | 1/1998 | Masters et al. |
| 5,714,350 A | 2/1998 | Co et al. |
| 5,714,352 A | 2/1998 | Jakobovits |
| 5,721,130 A | 2/1998 | Seubert et al. |
| 5,723,323 A | 3/1998 | Kauffman et al. |
| 5,733,743 A | 3/1998 | Johnson et al. |
| 5,750,349 A | 5/1998 | Suzuki et al. |
| 5,750,753 A | 5/1998 | Kimae et al. |
| 5,763,192 A | 6/1998 | Kauffman et al. |
| 5,766,846 A | 6/1998 | Schlossmacher et al. |
| 5,766,886 A | 6/1998 | Studnicka et al. |
| 5,770,429 A | 6/1998 | Lonberg et al. |
| 5,780,225 A | 7/1998 | Wigler et al. |
| 5,786,180 A | 7/1998 | Konig |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,837,500 A | 11/1998 | Ladner et al. |
| 5,855,913 A | 1/1999 | Hanes et al. |
| 5,874,064 A | 2/1999 | Edwards et al. |
| 5,877,397 A | 3/1999 | Lonberg et al. |
| 5,879,909 A | 3/1999 | Perl |
| 5,882,644 A | 3/1999 | Chang et al. |
| 5,885,793 A | 3/1999 | Griffiths et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,955,285 A | 9/1999 | Averback |
| 5,955,317 A | 9/1999 | Suzuki et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,010,913 A | 1/2000 | Vandermeeren et al. |
| 6,018,024 A | 1/2000 | Seubert et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,133 A | 9/2000 | Seubert et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,218,506 B1 | 4/2001 | Finch et al. |
| 6,284,221 B1 | 9/2001 | Schenk et al. |
| 6,287,793 B1 | 9/2001 | Schenk et al. |
| 6,294,171 B2 | 9/2001 | Mcmichael |
| 6,309,892 B1 | 10/2001 | Averback |
| 6,323,218 B1 | 11/2001 | Bush et al. |
| 6,333,034 B1 | 12/2001 | Gupta-bansal et al. |
| 6,350,861 B1 | 2/2002 | Co et al. |
| 6,387,674 B1 | 5/2002 | Trasciatti et al. |
| 6,582,945 B1 | 6/2003 | Raso |
| 6,610,493 B1 | 8/2003 | Citron et al. |
| 6,660,843 B1 | 12/2003 | Feige et al. |
| 6,664,442 B2 | 12/2003 | McConlogue et al. |
| 6,699,658 B1 | 3/2004 | Wittrup et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk |
| 6,761,888 B1 | 7/2004 | Schenk |
| 6,785,434 B2 | 8/2004 | Castoldi et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler et al. |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,919,075 B1 | 7/2005 | Solomon et al. |
| 6,972,127 B2 | 12/2005 | Schenk |
| 6,982,084 B2 | 1/2006 | Schenk |
| 7,014,855 B2 | 3/2006 | Schenk |
| 7,022,500 B1 | 4/2006 | Queen et al. |
| 7,045,531 B1 | 5/2006 | Bush et al. |
| 7,060,270 B2 | 6/2006 | Nicolau et al. |
| 7,067,133 B2 | 6/2006 | Nicolau |
| 7,094,884 B2 | 8/2006 | Scholz et al. |
| 7,122,374 B1 | 10/2006 | Saido et al. |
| 7,135,181 B2 | 11/2006 | Jensen et al. |
| 7,169,389 B2 | 1/2007 | Di Padova et al. |
| 7,179,463 B2 | 2/2007 | Lannfelt et al. |
| 7,179,606 B2 | 2/2007 | Jackowski et al. |
| 7,179,892 B2 | 2/2007 | Basi et al. |
| 7,186,881 B2 | 3/2007 | Games et al. |
| 7,189,703 B2 | 3/2007 | Balin et al. |
| 7,189,819 B2 | 3/2007 | Basi et al. |
| 7,195,761 B2 | 3/2007 | Holtzman et al. |
| 7,195,881 B2 | 3/2007 | Geffard |
| 7,196,163 B2 | 3/2007 | Hazuda et al. |
| 7,226,730 B1 | 6/2007 | De La Monte et al. |
| 7,238,488 B2 | 7/2007 | Maresh et al. |
| 7,238,788 B2 | 7/2007 | Lee |
| 7,247,301 B2 | 7/2007 | Van De et al. |
| 7,256,273 B2 | 8/2007 | Basi et al. |
| 7,270,818 B2 | 9/2007 | Averback |
| 7,279,165 B2 | 10/2007 | Bachmann et al. |
| 7,318,923 B2 | 1/2008 | Tsurushita et al. |
| 7,320,790 B2 | 1/2008 | Hinton et al. |
| 7,320,793 B2 | 1/2008 | Renner et al. |
| 7,335,491 B2 | 2/2008 | Drapeau et al. |
| 7,339,035 B2 | 3/2008 | Yanagisawa et al. |
| 7,342,091 B2 | 3/2008 | Kapurniotu et al. |
| 7,371,365 B2 | 5/2008 | Poduslo et al. |
| 7,375,190 B2 | 5/2008 | Cheng et al. |

(56) References Cited

U.S. PATENT DOCUMENTS

| | | |
|---|---|---|
| 7,413,884 B2 | 8/2008 | Raso |
| 7,427,342 B2 | 9/2008 | Barber |
| 7,625,560 B2 | 12/2009 | Basi et al. |
| 7,772,375 B2 | 8/2010 | Greferath et al. |
| 7,892,544 B2 | 2/2011 | Pfeifer et al. |
| 7,902,328 B2 | 3/2011 | Hillen et al. |
| 2001/0029293 A1 | 10/2001 | Gallatin et al. |
| 2002/0009445 A1 | 1/2002 | Du et al. |
| 2002/0015941 A1 | 2/2002 | Kim et al. |
| 2002/0086014 A1 | 7/2002 | Korman et al. |
| 2002/0086847 A1 | 7/2002 | Chain |
| 2002/0094335 A1 | 7/2002 | Chalifour et al. |
| 2002/0132758 A1 | 9/2002 | Shell |
| 2002/0137134 A1 | 9/2002 | Gerngross |
| 2002/0162129 A1 | 10/2002 | Lannfelt et al. |
| 2002/0182644 A1 | 12/2002 | Diamandis |
| 2002/0182660 A1 | 12/2002 | Fong |
| 2002/0188106 A1 | 12/2002 | Mandelkow et al. |
| 2002/0197258 A1 | 12/2002 | Ghanbari et al. |
| 2003/0065141 A1 | 4/2003 | Carter et al. |
| 2003/0068316 A1 | 4/2003 | Klein et al. |
| 2003/0073655 A1 | 4/2003 | Chain |
| 2003/0077278 A1 | 4/2003 | Gallatin et al. |
| 2003/0077757 A1 | 4/2003 | Andrews |
| 2003/0086938 A1 | 5/2003 | Jensen et al. |
| 2003/0100011 A1 | 5/2003 | Jackowski et al. |
| 2003/0100058 A1 | 5/2003 | Roschke et al. |
| 2003/0108551 A1 | 6/2003 | Nicolau et al. |
| 2003/0114510 A1 | 6/2003 | Ingram et al. |
| 2003/0147882 A1 | 8/2003 | Solomon et al. |
| 2003/0148356 A1 | 8/2003 | Cruts et al. |
| 2003/0157117 A1 | 8/2003 | Rasmussen et al. |
| 2003/0180722 A1 | 9/2003 | Godbole et al. |
| 2003/0185826 A1 | 10/2003 | Tobinick |
| 2003/0185827 A1 | 10/2003 | Rodriguez et al. |
| 2003/0186333 A1 | 10/2003 | Loring et al. |
| 2003/0186374 A1 | 10/2003 | Hufton et al. |
| 2003/0190689 A1 | 10/2003 | Crosby et al. |
| 2003/0194403 A1 | 10/2003 | Van De et al. |
| 2003/0195347 A1 | 10/2003 | Baker et al. |
| 2003/0228307 A1 | 12/2003 | Ramakrishnan et al. |
| 2003/0229907 A1 | 12/2003 | Hsiao et al. |
| 2003/0232758 A1 | 12/2003 | St. George-Hyslop et al. |
| 2004/0013647 A1 | 1/2004 | Solomon et al. |
| 2004/0013680 A1* | 1/2004 | Bush et al. ............... 424/185.1 |
| 2004/0018590 A1 | 1/2004 | Gerngross et al. |
| 2004/0043418 A1 | 3/2004 | Holtzman et al. |
| 2004/0053371 A1 | 3/2004 | Maresh et al. |
| 2004/0058414 A1 | 3/2004 | Queen et al. |
| 2004/0081657 A1 | 4/2004 | Schenk |
| 2004/0116337 A1 | 6/2004 | Kapurniotu et al. |
| 2004/0127471 A1 | 7/2004 | Reisberg |
| 2004/0138296 A1 | 7/2004 | Robertson et al. |
| 2004/0142872 A1 | 7/2004 | Poduslo et al. |
| 2004/0146512 A1 | 7/2004 | Rosenthal et al. |
| 2004/0157267 A1 | 8/2004 | Huang |
| 2004/0157779 A1 | 8/2004 | Schenk |
| 2004/0166119 A1 | 8/2004 | Schenk |
| 2004/0170641 A1 | 9/2004 | Schenk |
| 2004/0175394 A1 | 9/2004 | Schenk |
| 2004/0185039 A1 | 9/2004 | Kohler et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0223970 A1 | 11/2004 | Afar et al. |
| 2004/0228865 A1 | 11/2004 | Schenk |
| 2004/0241164 A1* | 12/2004 | Bales et al. ............... 424/145.1 |
| 2004/0242845 A1 | 12/2004 | Nicolau et al. |
| 2004/0248197 A1 | 12/2004 | Holtzman et al. |
| 2004/0265308 A1 | 12/2004 | Schenk |
| 2004/0265919 A1 | 12/2004 | Vanderstichele et al. |
| 2005/0009110 A1 | 1/2005 | Chang |
| 2005/0014821 A1 | 1/2005 | Tsai et al. |
| 2005/0019330 A1 | 1/2005 | Schenk |
| 2005/0019343 A1 | 1/2005 | Schenk |
| 2005/0031651 A1 | 2/2005 | Gervais et al. |
| 2005/0037026 A1 | 2/2005 | Schenk |
| 2005/0042664 A1 | 2/2005 | Wu et al. |
| 2005/0048584 A1 | 3/2005 | Lamping et al. |
| 2005/0053614 A1 | 3/2005 | Schenk |
| 2005/0057813 A1 | 3/2005 | Hasei et al. |
| 2005/0059591 A1 | 3/2005 | Schenk et al. |
| 2005/0059802 A1 | 3/2005 | Schenk et al. |
| 2005/0090439 A1 | 4/2005 | Chalifour et al. |
| 2005/0112543 A1 | 5/2005 | Bush et al. |
| 2005/0118651 A1 | 6/2005 | Basi et al. |
| 2005/0123544 A1 | 6/2005 | Schenk et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0142131 A1 | 6/2005 | Hinton et al. |
| 2005/0142132 A1 | 6/2005 | Schenk et al. |
| 2005/0147613 A1 | 7/2005 | Raso |
| 2005/0153381 A1 | 7/2005 | Marusich et al. |
| 2005/0163744 A1 | 7/2005 | Rasmussen et al. |
| 2005/0163788 A1 | 7/2005 | Schenk |
| 2005/0169925 A1 | 8/2005 | Bardroff et al. |
| 2005/0175626 A1 | 8/2005 | Delacourte et al. |
| 2005/0249725 A1 | 11/2005 | Schenk et al. |
| 2005/0249727 A1 | 11/2005 | Schenk |
| 2005/0255122 A1 | 11/2005 | Schenk |
| 2005/0272025 A1 | 12/2005 | Suo et al. |
| 2006/0008458 A1 | 1/2006 | Solomon |
| 2006/0029603 A1 | 2/2006 | Ellis et al. |
| 2006/0029611 A1 | 2/2006 | Schenk |
| 2006/0034858 A1 | 2/2006 | Schenk |
| 2006/0039906 A1 | 2/2006 | Holtzman et al. |
| 2006/0057646 A1 | 3/2006 | Wiltfang et al. |
| 2006/0057701 A1 | 3/2006 | Rosenthal et al. |
| 2006/0057702 A1 | 3/2006 | Rosenthal et al. |
| 2006/0062786 A1 | 3/2006 | Salcedo et al. |
| 2006/0073149 A1 | 4/2006 | Bales et al. |
| 2006/0099211 A1 | 5/2006 | Monthe et al. |
| 2006/0104968 A1 | 5/2006 | Bookbinder et al. |
| 2006/0105394 A1 | 5/2006 | Pomara |
| 2006/0110388 A1 | 5/2006 | Davies et al. |
| 2006/0111301 A1 | 5/2006 | Mattner |
| 2006/0127954 A1 | 6/2006 | Mercken et al. |
| 2006/0141541 A1 | 6/2006 | McIntyre |
| 2006/0160161 A1 | 7/2006 | Pavliakova et al. |
| 2006/0165682 A1 | 7/2006 | Basi et al. |
| 2006/0166275 A1 | 7/2006 | Krafft et al. |
| 2006/0166311 A1 | 7/2006 | Okochi et al. |
| 2006/0188505 A1 | 8/2006 | Skurkovich et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0234947 A1 | 10/2006 | Gazit |
| 2006/0240007 A1 | 10/2006 | Sanders |
| 2006/0241038 A1 | 10/2006 | Watanabe et al. |
| 2006/0246075 A1 | 11/2006 | Mercken et al. |
| 2006/0257420 A1 | 11/2006 | Zimmerman |
| 2006/0257882 A1 | 11/2006 | Shimkets et al. |
| 2006/0280733 A1 | 12/2006 | Kayed et al. |
| 2006/0292152 A1 | 12/2006 | Rosenthal et al. |
| 2007/0009931 A1 | 1/2007 | Kirsch |
| 2007/0010435 A1 | 1/2007 | Frangione et al. |
| 2007/0010657 A1 | 1/2007 | Klocke et al. |
| 2007/0015217 A1 | 1/2007 | Durham et al. |
| 2007/0015218 A1 | 1/2007 | Cao et al. |
| 2007/0021345 A1 | 1/2007 | Gazit |
| 2007/0031416 A1 | 2/2007 | Shoji et al. |
| 2007/0036789 A1 | 2/2007 | Chung |
| 2007/0036794 A1 | 2/2007 | Devaux et al. |
| 2007/0042424 A1 | 2/2007 | Ebinuma et al. |
| 2007/0048312 A1 | 3/2007 | Klein et al. |
| 2007/0071675 A1 | 3/2007 | Wu et al. |
| 2007/0072307 A1 | 3/2007 | Godavarti et al. |
| 2007/0081998 A1 | 4/2007 | Kinney et al. |
| 2007/0082350 A1 | 4/2007 | Landfield et al. |
| 2007/0086994 A1 | 4/2007 | Wallach et al. |
| 2007/0098721 A1 | 5/2007 | Hillen et al. |
| 2007/0105092 A1 | 5/2007 | Paul et al. |

(56) References Cited

U.S. PATENT DOCUMENTS

| | | |
|---|---|---|
| 2007/0110750 A1 | 5/2007 | Glabe et al. |
| 2007/0111252 A1 | 5/2007 | Suzuki et al. |
| 2007/0122405 A1 | 5/2007 | Roschke et al. |
| 2007/0128191 A1 | 6/2007 | Barrio |
| 2007/0134247 A9 | 6/2007 | Solomon |
| 2007/0135337 A2 | 6/2007 | Chalifour et al. |
| 2007/0140966 A1 | 6/2007 | Chang et al. |
| 2007/0148167 A1 | 6/2007 | Strohl |
| 2007/0160616 A1 | 7/2007 | Rosenthal et al. |
| 2007/0167522 A1 | 7/2007 | Imawaka et al. |
| 2007/0190046 A1 | 8/2007 | DeMaattos et al. |
| 2007/0196367 A1 | 8/2007 | Dinu |
| 2007/0213512 A1 | 9/2007 | Krafft et al. |
| 2007/0218069 A1 | 9/2007 | Gordon et al. |
| 2007/0218499 A1 | 9/2007 | Lambert et al. |
| 2007/0231331 A1 | 10/2007 | Dewji et al. |
| 2007/0248606 A1 | 10/2007 | Lannfelt et al. |
| 2007/0264276 A1 | 11/2007 | Chalifour et al. |
| 2007/0280953 A1 | 12/2007 | Rosenberg et al. |
| 2007/0292410 A1 | 12/2007 | Cashman et al. |
| 2007/0292895 A1 | 12/2007 | Shi et al. |
| 2008/0009467 A1 | 1/2008 | Henderson |
| 2008/0014194 A1 | 1/2008 | Schenk et al. |
| 2008/0025988 A1 | 1/2008 | Yamaguchi et al. |
| 2008/0029911 A1 | 2/2008 | Jeon et al. |
| 2008/0044356 A1 | 2/2008 | Lesne et al. |
| 2008/0044406 A1 | 2/2008 | Johnson-Wood et al. |
| 2008/0051690 A1 | 2/2008 | Mattner et al. |
| 2008/0057053 A1 | 3/2008 | Stolen |
| 2008/0057593 A1 | 3/2008 | Vanderstichele et al. |
| 2008/0058276 A1 | 3/2008 | Lu et al. |
| 2008/0058330 A1 | 3/2008 | Paris et al. |
| 2008/0089885 A1 | 4/2008 | Smith et al. |
| 2008/0096818 A1 | 4/2008 | Schenk et al. |
| 2008/0107601 A1 | 5/2008 | Lauwereys et al. |
| 2008/0107649 A1 | 5/2008 | Zurbriggen |
| 2008/0113444 A1 | 5/2008 | Pray |
| 2008/0131422 A1 | 6/2008 | Sugimura et al. |
| 2008/0199879 A1 | 8/2008 | Takayama et al. |
| 2008/0220449 A1 | 9/2008 | Vasan et al. |
| 2008/0292639 A1 | 11/2008 | Shen et al. |
| 2008/0299111 A1 | 12/2008 | Delacourte et al. |
| 2009/0018084 A1 | 1/2009 | Krafft et al. |
| 2009/0023159 A1 | 1/2009 | Mendez |
| 2009/0035295 A1 | 2/2009 | Hillen et al. |
| 2009/0035307 A1 | 2/2009 | Barghorn et al. |
| 2009/0074775 A1 | 3/2009 | Holtzman et al. |
| 2009/0155246 A1 | 6/2009 | Gellerfors et al. |
| 2009/0156471 A1 | 6/2009 | Gazit et al. |
| 2009/0162362 A1 | 6/2009 | Sarasa |
| 2009/0162878 A1 | 6/2009 | Kim et al. |
| 2009/0175847 A1 | 7/2009 | Hillen |
| 2009/0191190 A1 | 7/2009 | Barghorn |
| 2009/0214515 A1 | 8/2009 | Holzman et al. |
| 2009/0232801 A1 | 9/2009 | Hillen |
| 2009/0238831 A1 | 9/2009 | Hillen et al. |
| 2010/0173828 A1 | 7/2010 | Hillen |
| 2010/0209346 A1 | 8/2010 | Hillen et al. |
| 2011/0092445 A1 | 4/2011 | Barghorn |
| 2011/0212109 A1 | 9/2011 | Barghorn |
| 2011/0256138 A1 | 10/2011 | Barghorn |
| 2011/0287005 A1 | 11/2011 | Hillen |

FOREIGN PATENT DOCUMENTS

| | | |
|---|---|---|
| CN | 1396183 | 2/2003 |
| CN | 1446581 | 10/2003 |
| CN | 1673369 | 9/2005 |
| CN | 1721437 | 1/2006 |
| CN | 1803842 | 7/2006 |
| CN | 101058608 | 10/2007 |
| CN | 101084909 | 12/2007 |
| CN | 101152576 | 4/2008 |
| DE | 19902550 | 7/2000 |
| DE | 10055703 | 5/2002 |
| DE | 10303974 | 8/2004 |
| DE | 102004039326 | 2/2006 |
| EP | 0045665 | 2/1982 |
| EP | 0050424 | 9/1985 |
| EP | 0285159 | 10/1988 |
| EP | 0341491 | 11/1989 |
| EP | 0084796 | 5/1990 |
| EP | 0391714 | 10/1990 |
| EP | 0411974 | 2/1991 |
| EP | 0415801 | 3/1991 |
| EP | 0237362 | 3/1992 |
| EP | 0201184 | 12/1992 |
| EP | 0229246 | 8/1993 |
| EP | 0368684 | 3/1994 |
| EP | 0239400 | 8/1994 |
| EP | 0613007 | 8/1994 |
| EP | 0623675 | 11/1994 |
| EP | 0557270 | 5/1995 |
| EP | 0519598 | 6/1995 |
| EP | 0440619 | 1/1996 |
| EP | 0304013 | 6/1996 |
| EP | 0589877 | 11/1996 |
| EP | 0436597 | 4/1997 |
| EP | 0258017 | 6/1997 |
| EP | 0783104 | 7/1997 |
| EP | 0444856 | 9/1997 |
| EP | 0816492 | 1/1998 |
| EP | 0592127 | 4/1998 |
| EP | 0274826 | 8/1998 |
| EP | 0527839 | 12/1998 |
| EP | 1038958 | 9/2000 |
| EP | 1094080 | 4/2001 |
| EP | 1130032 | 11/2001 |
| EP | 1172378 | 1/2002 |
| EP | 1176195 | 1/2002 |
| EP | 0877939 | 6/2002 |
| EP | 0683234 | 5/2003 |
| EP | 1308461 | 5/2003 |
| EP | 1408333 | 4/2004 |
| EP | 1420032 | 5/2004 |
| EP | 1270592 | 9/2004 |
| EP | 1467212 | 10/2004 |
| EP | 0592106 | 11/2004 |
| EP | 1200470 | 11/2004 |
| EP | 0519596 | 2/2005 |
| EP | 1538163 | 6/2005 |
| EP | 1632242 | 3/2006 |
| EP | 1092767 | 10/2006 |
| EP | 1717250 | 11/2006 |
| EP | 0998495 | 12/2006 |
| EP | 1731913 | 12/2006 |
| EP | 1049712 | 1/2007 |
| EP | 1741783 | 1/2007 |
| EP | 1346041 | 2/2007 |
| EP | 1752472 | 2/2007 |
| EP | 1592476 | 4/2007 |
| EP | 0970203 | 5/2007 |
| EP | 1787998 | 5/2007 |
| EP | 0948536 | 6/2007 |
| EP | 1160256 | 6/2007 |
| EP | 1379546 | 6/2007 |
| EP | 1792991 | 6/2007 |
| EP | 1842859 | 10/2007 |
| EP | 1861422 | 12/2007 |
| EP | 1878751 | 1/2008 |
| EP | 1434053 | 3/2008 |
| EP | 1521831 | 4/2008 |
| EP | 1778837 | 4/2008 |
| EP | 1911765 | 4/2008 |
| EP | 1781644 | 5/2008 |
| EP | 0911398 | 6/2008 |
| EP | 1976877 | 10/2008 |
| EP | 2009445 | 12/2008 |
| EP | 1623719 | 1/2009 |
| EP | 1681566 | 8/2009 |
| EP | 1766396 | 8/2010 |
| EP | 1720909 | 11/2011 |
| FR | 2740454 | 4/1997 |

(56) References Cited

FOREIGN PATENT DOCUMENTS

| | | |
|---|---|---|
| FR | 2741881 | 6/1997 |
| GB | 1495159 | 12/1977 |
| GB | 2371303 | 7/2002 |
| GR | 1005016 | 10/2005 |
| JP | 63240797 | 10/1988 |
| JP | 4252195 | 9/1992 |
| JP | 4320694 | 11/1992 |
| JP | 7209295 | 8/1995 |
| JP | 7209296 | 8/1995 |
| JP | 07238096 | 9/1995 |
| JP | 7309900 | 11/1995 |
| JP | 8245700 | 9/1996 |
| JP | 9067397 | 3/1997 |
| JP | 10075781 | 3/1998 |
| JP | 10210982 | 8/1998 |
| JP | 2000050885 | 2/2000 |
| JP | 2000354487 | 12/2000 |
| JP | 2001231578 | 8/2001 |
| JP | 2002040023 | 2/2002 |
| JP | 2002253252 | 9/2002 |
| JP | 2004107260 | 4/2004 |
| JP | 2005185281 | 7/2005 |
| JP | 2006166879 | 6/2006 |
| JP | 2006213621 | 8/2006 |
| JP | 2006265189 | 10/2006 |
| JP | 2007077103 | 3/2007 |
| JP | 2007300856 | 11/2007 |
| JP | 2007319127 | 12/2007 |
| JP | 2008096311 | 4/2008 |
| KR | 100806914 | 2/2008 |
| WO | WO 88/03951 | 6/1988 |
| WO | WO 89/06689 | 7/1989 |
| WO | WO 89/07657 | 8/1989 |
| WO | WO 90/02809 | 3/1990 |
| WO | WO 90/05144 | 5/1990 |
| WO | WO 90/12870 | 11/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09967 | 7/1991 |
| WO | WO 91/17271 | 11/1991 |
| WO | WO 92/01047 | 1/1992 |
| WO | WO 92/02551 | 2/1992 |
| WO | WO 92/00969 | 6/1992 |
| WO | WO 92/09690 | 6/1992 |
| WO | WO 92/11018 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/08302 | 4/1993 |
| WO | WO 93/11236 | 10/1993 |
| WO | WO 94/02602 | 3/1994 |
| WO | WO 94/17197 | 8/1994 |
| WO | WO 95/07707 | 3/1995 |
| WO | WO 95/11311 | 4/1995 |
| WO | WO 95/11994 | 5/1995 |
| WO | WO 95/15982 | 6/1995 |
| WO | WO 95/16787 | 6/1995 |
| WO | WO 95/20401 | 8/1995 |
| WO | WO 96/20218 | 7/1996 |
| WO | WO 96/20698 | 7/1996 |
| WO | WO 96/28187 | 9/1996 |
| WO | WO 96/33735 | 10/1996 |
| WO | WO 96/34096 | 10/1996 |
| WO | WO 96/39512 | 12/1996 |
| WO | WO 96/40731 | 12/1996 |
| WO | WO 97/08320 | 3/1997 |
| WO | WO 97/10505 | 3/1997 |
| WO | WO 97/18476 | 5/1997 |
| WO | WO 97/29131 | 8/1997 |
| WO | WO 97/32572 | 9/1997 |
| WO | WO 97/44013 | 11/1997 |
| WO | WO 97/46678 | 12/1997 |
| WO | WO 98/05350 | 2/1998 |
| WO | WO 98/07850 | 2/1998 |
| WO | WO 98/13490 | 4/1998 |
| WO | WO 98/16654 | 4/1998 |
| WO | WO 98/22120 | 5/1998 |
| WO | WO 98/24893 | 6/1998 |
| WO | WO 98/28445 | 7/1998 |
| WO | WO 98/31346 | 7/1998 |
| WO | WO 98/31700 | 7/1998 |
| WO | WO 98/33815 | 8/1998 |
| WO | WO 98/41201 | 9/1998 |
| WO | WO 98/47343 | 10/1998 |
| WO | WO 98/49286 | 11/1998 |
| WO | WO 98/50433 | 11/1998 |
| WO | WO 98/51793 | 11/1998 |
| WO | WO 99/05175 | 2/1999 |
| WO | WO 99/09150 | 2/1999 |
| WO | WO 99/12870 | 3/1999 |
| WO | WO 99/13908 | 3/1999 |
| WO | WO 99/15154 | 4/1999 |
| WO | WO 99/20253 | 4/1999 |
| WO | WO 99/22024 | 5/1999 |
| WO | WO 99/25044 | 5/1999 |
| WO | WO 99/27944 | 6/1999 |
| WO | WO 99/27949 | 6/1999 |
| WO | WO 91/10737 | 7/1999 |
| WO | WO 91/10741 | 7/1999 |
| WO | WO 99/33815 | 7/1999 |
| WO | WO 99/36569 | 7/1999 |
| WO | WO 99/40909 | 8/1999 |
| WO | WO 99/45031 | 9/1999 |
| WO | WO 99/45962 | 9/1999 |
| WO | WO 99/53049 | 10/1999 |
| WO | WO 99/58157 | 11/1999 |
| WO | WO 99/58564 | 11/1999 |
| WO | WO 99/59571 | 11/1999 |
| WO | WO 99/62505 | 12/1999 |
| WO | WO 99/66903 | 12/1999 |
| WO | WO 00/009560 | 2/2000 |
| WO | WO 00/017345 | 3/2000 |
| WO | WO 00/018805 | 4/2000 |
| WO | WO 00/029446 | 5/2000 |
| WO | WO 00/032805 | 6/2000 |
| WO | WO 00/035939 | 6/2000 |
| WO | WO 00/037504 | 6/2000 |
| WO | WO 00/056772 | 9/2000 |
| WO | WO 00/058344 | 10/2000 |
| WO | WO 00/072870 | 12/2000 |
| WO | WO 00/072876 | 12/2000 |
| WO | WO 00/072880 | 12/2000 |
| WO | WO 00/075328 | 12/2000 |
| WO | WO 00/077178 | 12/2000 |
| WO | WO 00/078807 | 12/2000 |
| WO | WO 01/010900 | 2/2001 |
| WO | WO 01/16364 | 3/2001 |
| WO | WO 01/018169 | 3/2001 |
| WO | WO 01/032712 | 5/2001 |
| WO | WO 01/039796 | 6/2001 |
| WO | WO 01/042306 | 6/2001 |
| WO | WO 01/062284 | 8/2001 |
| WO | WO 01/062801 | 8/2001 |
| WO | WO 01/068860 | 9/2001 |
| WO | WO 01/083519 | 11/2001 |
| WO | WO 01/083525 | 11/2001 |
| WO | WO 01/85093 | 11/2001 |
| WO | WO 01/090182 | 11/2001 |
| WO | WO 01/098361 | 12/2001 |
| WO | WO 02/000245 | 1/2002 |
| WO | WO 02/003911 | 1/2002 |
| WO | WO 02/021141 | 3/2002 |
| WO | WO 02/030980 | 4/2002 |
| WO | WO 02/034777 | 5/2002 |
| WO | WO 02/036614 | 5/2002 |
| WO | 02/046237 | 6/2002 |
| WO | WO 02/055552 | 7/2002 |
| WO | WO 02/059155 | 8/2002 |
| WO | WO 02/062851 | 8/2002 |

(56) References Cited

FOREIGN PATENT DOCUMENTS

| | | |
|---|---|---|
| WO | WO 02/074240 | 9/2002 |
| WO | WO 02/081505 | 10/2002 |
| WO | WO 02/085922 | 10/2002 |
| WO | WO 02/088306 | 11/2002 |
| WO | WO 02/088307 | 11/2002 |
| WO | WO 02/094870 | 11/2002 |
| WO | WO 02/094985 | 11/2002 |
| WO | WO 02/096350 | 12/2002 |
| WO | WO 02/096937 | 12/2002 |
| WO | WO 03/000714 | 1/2003 |
| WO | WO 03/008626 | 1/2003 |
| WO | WO 03/014162 | 2/2003 |
| WO | WO 03/014329 | 2/2003 |
| WO | WO 03/015617 | 2/2003 |
| WO | WO 03/015691 | 2/2003 |
| WO | WO 03/015812 | 2/2003 |
| WO | WO 03/016466 | 2/2003 |
| WO | WO 03/016467 | 2/2003 |
| WO | WO 03/020212 | 3/2003 |
| WO | WO 03/028668 | 4/2003 |
| WO | WO 03/031475 | 4/2003 |
| WO | WO 03/035835 | 5/2003 |
| WO | WO 03/039467 | 5/2003 |
| WO | WO 03/045128 | 6/2003 |
| WO | WO 03/046012 | 6/2003 |
| WO | WO 03/047499 | 6/2003 |
| WO | WO 03/051374 | 6/2003 |
| WO | WO 03/070760 | 8/2003 |
| WO | WO 03/074081 | 8/2003 |
| WO | WO 03/074004 | 9/2003 |
| WO | WO 03/074569 | 9/2003 |
| WO | WO 03/076455 | 9/2003 |
| WO | WO 03/077858 | 9/2003 |
| WO | 03/080672 | 10/2003 |
| WO | WO 03/089460 | 10/2003 |
| WO | WO 03/090772 | 11/2003 |
| WO | WO 03/091734 | 11/2003 |
| WO | WO 03/095429 | 11/2003 |
| WO | 03/104437 | 12/2003 |
| WO | WO 03/100419 | 12/2003 |
| WO | WO 03/105658 | 12/2003 |
| WO | WO 2004/001422 | 12/2003 |
| WO | WO 2004/003019 | 1/2004 |
| WO | WO 2004/003563 | 1/2004 |
| WO | WO 2004/006861 | 1/2004 |
| WO | WO 2004/009776 | 1/2004 |
| WO | WO 2004/011674 | 2/2004 |
| WO | WO 2004/011943 | 2/2004 |
| WO | WO 2004/013172 | 2/2004 |
| WO | WO 2004/014296 | 2/2004 |
| WO | WO 2004/014367 | 2/2004 |
| WO | WO 2004/016282 | 2/2004 |
| WO | WO 2004/016655 | 2/2004 |
| WO | WO 2004/018997 | 3/2004 |
| WO | WO 2004/019045 | 3/2004 |
| WO | WO 2004/024090 | 3/2004 |
| WO | WO 2004/029093 | 4/2004 |
| WO | WO 2004/029630 | 4/2004 |
| WO | WO 2004/031241 | 4/2004 |
| WO | WO 2004/031400 | 4/2004 |
| WO | WO 2004/032868 | 4/2004 |
| WO | WO 2004/033397 | 4/2004 |
| WO | WO 2004/050707 | 4/2004 |
| WO | WO 2004/038411 | 5/2004 |
| WO | WO 2004/041067 | 5/2004 |
| WO | WO 2004/043989 | 5/2004 |
| WO | WO 2004/044204 | 5/2004 |
| WO | WO 2004/045525 | 6/2004 |
| WO | WO 2004/050850 | 6/2004 |
| WO | WO 2004/050876 | 6/2004 |
| WO | WO 2004/056318 | 7/2004 |
| WO | WO 2004/058239 | 7/2004 |
| WO | WO 2004/058258 | 7/2004 |
| WO | WO 2004/058820 | 7/2004 |
| WO | WO 2004/062556 | 7/2004 |
| WO | 2004/068931 | 8/2004 |
| WO | WO 2004/065419 | 8/2004 |
| WO | WO 2004/065569 | 8/2004 |
| WO | WO 2004/067561 | 8/2004 |
| WO | WO 2004/069182 | 8/2004 |
| WO | WO 2004/071408 | 8/2004 |
| WO | WO 2004/072286 | 8/2004 |
| WO | WO 2004/074837 | 9/2004 |
| WO | WO 2004/078140 | 9/2004 |
| WO | WO 2004/085712 | 10/2004 |
| WO | WO 2004/087733 | 10/2004 |
| WO | WO 2004/087735 | 10/2004 |
| WO | WO 2004/090544 | 10/2004 |
| WO | WO 2004/095031 | 11/2004 |
| WO | WO 2004/098631 | 11/2004 |
| WO | WO 2004/104597 | 12/2004 |
| WO | WO 2004/108895 | 12/2004 |
| WO | WO 2004/111250 | 12/2004 |
| WO | WO 2005/000897 | 1/2005 |
| WO | WO 2005/005638 | 1/2005 |
| WO | WO 2005/011599 | 2/2005 |
| WO | WO 2005/012330 | 2/2005 |
| WO | WO 2005/014618 | 2/2005 |
| WO | WO 2005/016236 | 2/2005 |
| WO | WO 2005/018424 | 3/2005 |
| WO | WO 2005/018536 | 3/2005 |
| WO | WO 2005/025516 | 3/2005 |
| WO | WO 2005/025592 | 3/2005 |
| WO | WO 2005/025616 | 3/2005 |
| WO | WO 2005/026360 | 3/2005 |
| WO | WO 2005/027965 | 3/2005 |
| WO | WO 2005/028511 | 3/2005 |
| WO | WO 2005/033142 | 4/2005 |
| WO | WO 2005/033145 | 4/2005 |
| WO | WO 2005/037209 | 4/2005 |
| WO | WO 2005/040212 | 5/2005 |
| WO | WO 2005/041650 | 5/2005 |
| WO | WO 2005/044306 | 5/2005 |
| WO | WO 2005/046605 | 5/2005 |
| WO | WO 2005/047484 | 5/2005 |
| WO | WO 2005/047860 | 5/2005 |
| WO | WO 2005/051998 | 6/2005 |
| WO | WO 2005/052002 | 6/2005 |
| WO | WO 2005/053604 | 6/2005 |
| WO | WO 2005/058815 | 6/2005 |
| WO | WO 2005/058940 | 6/2005 |
| WO | WO 2005/120571 | 7/2005 |
| WO | WO 2005/070965 | 8/2005 |
| WO | WO 2005/072777 | 8/2005 |
| WO | WO 2005/080986 | 9/2005 |
| WO | WO 2005/081872 | 9/2005 |
| WO | WO 2005/090971 | 9/2005 |
| WO | WO 2005/095457 | 10/2005 |
| WO | WO 2005/096730 | 10/2005 |
| WO | WO 2005/100584 | 10/2005 |
| WO | WO 2005/105841 | 11/2005 |
| WO | WO 2005/105847 | 11/2005 |
| WO | WO 2005/105998 | 11/2005 |
| WO | WO 2005/108378 | 11/2005 |
| WO | WO 2005/110056 | 11/2005 |
| WO | WO 2005/123775 | 12/2005 |
| WO | WO 2005/123776 | 12/2005 |
| WO | WO 2006/005588 | 1/2006 |
| WO | WO 2006/005707 | 1/2006 |
| WO | WO 2006/014478 | 2/2006 |
| WO | WO 2006/014638 | 2/2006 |
| WO | WO 2006/015976 | 2/2006 |
| WO | WO 2006/016644 | 2/2006 |
| WO | WO 2006/033688 | 3/2006 |
| WO | WO 2006/036291 | 4/2006 |
| WO | WO 2006/037604 | 4/2006 |
| WO | WO 2006/038729 | 4/2006 |
| WO | WO 2006/039327 | 4/2006 |
| WO | WO 2006/039470 | 4/2006 |
| WO | WO 2006/040153 | 4/2006 |
| WO | WO 2006/041934 | 4/2006 |
| WO | WO 2006/047254 | 5/2006 |
| WO | WO 2006/047670 | 5/2006 |
| WO | WO 2006/050041 | 5/2006 |

(56) References Cited

FOREIGN PATENT DOCUMENTS

| | | |
|---|---|---|
| WO | WO 2006/050667 | 5/2006 |
| WO | WO 2006/052924 | 5/2006 |
| WO | WO 2006/053428 | 5/2006 |
| WO | WO 2006/055178 | 5/2006 |
| WO | WO 2006/066049 | 6/2006 |
| WO | WO 2006/066089 | 6/2006 |
| WO | WO 2006/066118 | 6/2006 |
| WO | WO 2006/066171 | 6/2006 |
| WO | WO 2006/066233 | 6/2006 |
| WO | WO 2006/067792 | 6/2006 |
| WO | WO 2006/069081 | 6/2006 |
| WO | WO 2006/069202 | 6/2006 |
| WO | WO 2006/081171 | 8/2006 |
| WO | WO 2006/083533 | 8/2006 |
| WO | WO 2006/083689 | 8/2006 |
| WO | WO 2006/087550 | 8/2006 |
| WO | WO 2006/094192 | 9/2006 |
| WO | WO 2006/094724 | 9/2006 |
| WO | WO 2006/095041 | 9/2006 |
| WO | WO 2006/096529 | 9/2006 |
| WO | WO 2006/096653 | 9/2006 |
| WO | WO 2006/099543 | 9/2006 |
| WO | WO 2006/100679 | 9/2006 |
| WO | WO 2006/103116 | 10/2006 |
| WO | WO 2006/110748 | 10/2006 |
| WO | WO 2006/116369 | 11/2006 |
| WO | WO 2006/118959 | 11/2006 |
| WO | WO 2006/119449 | 11/2006 |
| WO | WO 2006/121656 | 11/2006 |
| WO | WO 2006/125830 | 11/2006 |
| WO | WO 2006/128163 | 11/2006 |
| WO | WO 2006/133164 | 12/2006 |
| WO | WO 2006/137354 | 12/2006 |
| WO | WO 2007/005358 | 1/2007 |
| WO | WO 2007/005359 | 1/2007 |
| WO | WO 2007/008547 | 1/2007 |
| WO | WO 2007/011639 | 1/2007 |
| WO | WO 2007/011834 | 1/2007 |
| WO | WO 2007/017686 | 2/2007 |
| WO | WO 2007/019620 | 2/2007 |
| WO | WO 2007/021886 | 2/2007 |
| WO | WO 2007/022416 | 2/2007 |
| WO | WO 2007/040437 | 4/2007 |
| WO | WO 2007/042261 | 4/2007 |
| WO | WO 2007/047967 | 4/2007 |
| WO | WO 2007/047995 | 4/2007 |
| WO | WO 2007/050359 | 5/2007 |
| WO | WO 2007/053661 | 5/2007 |
| WO | WO 2007/059135 | 5/2007 |
| WO | WO 2007/059203 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/067512 | 6/2007 |
| WO | WO 2007/068411 | 6/2007 |
| WO | WO 2007/068429 | 6/2007 |
| WO | WO 2007/082750 | 7/2007 |
| WO | WO 2007/068412 | 8/2007 |
| WO | WO 2007/088399 | 8/2007 |
| WO | WO 2007/088712 | 8/2007 |
| WO | WO 2007/090872 | 8/2007 |
| WO | WO 2007/092861 | 8/2007 |
| WO | WO 2007/096076 | 8/2007 |
| WO | WO 2007/097251 | 8/2007 |
| WO | WO 2007/098417 | 8/2007 |
| WO | WO 2007/103788 | 9/2007 |
| WO | WO 2007/106617 | 9/2007 |
| WO | WO 2007/108756 | 9/2007 |
| WO | WO 2007/109107 | 9/2007 |
| WO | WO 2007/109749 | 9/2007 |
| WO | WO 2007/112288 | 10/2007 |
| WO | WO 2007/113172 | 10/2007 |
| WO | WO 2007/118984 | 10/2007 |
| WO | WO 2007/119685 | 10/2007 |
| WO | WO 2007/123345 | 11/2007 |
| WO | WO 2007/125351 | 11/2007 |
| WO | WO 2007/127393 | 11/2007 |
| WO | WO 2007/127448 | 11/2007 |
| WO | WO 2007/129457 | 11/2007 |
| WO | WO 2007/144198 | 12/2007 |
| WO | WO 2007/149032 | 12/2007 |
| WO | WO 2008/002893 | 1/2008 |
| WO | WO 2008/008939 | 1/2008 |
| WO | WO 2008/011348 | 1/2008 |
| WO | WO 2008/012101 | 1/2008 |
| WO | WO 2008/015384 | 2/2008 |
| WO | WO 2008/021296 | 2/2008 |
| WO | WO 2008/022349 | 2/2008 |
| WO | WO 2008/027526 | 3/2008 |
| WO | WO 2008/028939 | 3/2008 |
| WO | WO 2008/030251 | 3/2008 |
| WO | WO 2008/030973 | 3/2008 |
| WO | WO 2008/031911 | 3/2008 |
| WO | Wo 2008/045962 | 4/2008 |
| WO | WO 2008/047111 | 4/2008 |
| WO | WO 2008/051017 | 5/2008 |
| WO | WO 2008/051326 | 5/2008 |
| WO | WO 2008/057240 | 5/2008 |
| WO | WO 2008/060364 | 5/2008 |
| WO | WO 2008/061795 | 5/2008 |
| WO | WO 2008/064244 | 5/2008 |
| WO | WO 2008/067464 | 6/2008 |
| WO | WO 2008/070229 | 6/2008 |
| WO | WO 2008/071394 | 6/2008 |
| WO | WO 2008/084402 | 7/2008 |
| WO | WO 2008/104385 | 9/2008 |
| WO | WO 2008/104386 | 9/2008 |
| WO | WO 2008/107677 | 9/2008 |
| WO | WO 2008/110885 | 9/2008 |
| WO | WO 2008/122441 | 10/2008 |
| WO | WO 2008/124940 | 10/2008 |
| WO | WO 2008/129023 | 10/2008 |
| WO | WO 2008/130449 | 10/2008 |
| WO | WO 2008/131298 | 10/2008 |
| WO | WO 2008/134034 | 11/2008 |
| WO | WO 2008/143708 | 11/2008 |
| WO | 2008/150949 | 12/2008 |
| WO | WO 2008/150467 | 12/2008 |
| WO | WO 2008/150946 | 12/2008 |
| WO | WO 2008/156621 | 12/2008 |
| WO | WO 2008/156622 | 12/2008 |
| WO | WO 2009/008890 | 1/2009 |
| WO | WO 2009/008891 | 1/2009 |
| WO | WO 2009/009768 | 1/2009 |
| WO | WO 2009/044160 | 4/2009 |
| WO | WO 2009/048537 | 4/2009 |
| WO | WO 2009/048538 | 4/2009 |
| WO | WO 2009/048539 | 4/2009 |
| WO | WO 2010/097012 | 9/2010 |

OTHER PUBLICATIONS

Gong, Y. et al., "Abeta-derived diffusible ligands in Alzheimer's disease brain as therapeutic antibody targets," Abstracts of the Annual Meeting of the Society of Neuroscience (2002) 1 page.

Gong, Y., "Alzheimer's disease-affected brain: presence of oligomeric a ligands (ADDLs) suggests a molecular basis for reversible memory loss," Proc. Natl. Acad. Sci. (2003) 100(18):10417-10422.

Hillen, H. et al., "Generation and therapeutic efficacy of highly oligomer-specific beta-amyloid antibodies," J. Neurosci. (2010) 30(31):10369-10379.

Kayed, R. et al., "Common structure of soluble amyloid oligomers implies common mechanism of pathogenesis," Science (2003) 300(18):486-489.

Klein, W., "A beta toxicity in Alzheimers disease; globular oligomers (ADDLs) as new vaccine and drug targets," Neurochem. Intl. (2002) 41(5):345-352.

Lambert, M.P. et al., "Vaccination with soluble AB oilgerm generates toxicity-neutralizing antibodies," J. Neurochem. (2001) 79(3):595-605.

(56) References Cited

OTHER PUBLICATIONS

Stine, W.B. et al., "Antibodies specific for toxic Abeta oligomers," Abst. Viewer/Itinerary Planner, Soc. Of Neurosci. (2003) 1.
Qiu, W., "Facile synthesis of hydrocarbon-stapled peptides," Anaspec poster at 20th American Peptide Society Annual Meeting (2008).
Aisen, P.S. et al., "The development of anti-amyloid etherapy for Alzheimer's disease: from secretase modulators to polymerisation inhibitors," CNS Drugs (2005) 19(12):989-996.
Albert, S.E. et al., "Time-dependent induction of protective anti-influenza immune responses in human peripheral blood lymphocyte/SCID mice," J. Immunol. (1997) 153(3):1393-1403.
Almquist, R.G. et al., "Synthesis and biological activity of a ketomethylene analogue of a tripeptide inhibitor of angiotensin converting enzyme," J. Med. Chem. (1980) 23:1392-1398.
Altschul, S.F. et la., "Gapped BLAST and PSI_BLAST: a new generation of protein database search programs," Nucl. Acids Res. (1997) 25(17):3389-3402.
Ames, R.S. et al., "Conversion of murine Fabs isolated from a combinatorial phage display library to full length immunoglobulins," J. Immunol. Meth. (1995) 184:177-186.
Arai, K. et al., "An ELISA to determine the biodistribution of human monoclonal antibody in tumor-xenografted SCID mice," J. Immunol. Meth. (1998) 217:79-85.
Ardaillou, R., "An Ang II antagonist improves the Alzheimer's disease of the mouse," Medecine/Sciences (2008) 24(1):41.
Arispe, N. et al., "Alzheimer disease amyloid beta protein forms calcium channels in bilayer membranes: blockage by tromethamine and aluminum," Proc. Natl. Acad. Sci. (1993) 90:567-571.
Armstrong, J. et al., "Familial Alzheimer disease associated with A713T mutation in APP," Neurosci. Letters (2004) 370;241-243.
Asakura, K. et al., "Alpha-eudesmol, a P/Q-type Ca2+ channel blocker, inhibits neurogenic vasodilatation and extravasation following electrical stimulation of trigeminal gangion," Brain Res. (2000) 873:94-101, abstract.
Asakura, K. et al., "P/Q-type Ca2+ channel blocker game-agatoxin IVA protects against brain injury after focal ischemia in rats," Brain Res. (1997) 776:140-145, abstract.
Askanas, V. et al., "Inclusion-body myositis: a myodegenerative conformational disorder associated with Abeta, protein misfolding, and proteasome inhibition," Neurology (2006) 66(2) Supp 1:S39-48.
Askanas, V. et al., "Molecular pathology and pathogenesis of inclusion-body myositis," Microscopy Res. Technique (2005) 67:114-120.
Askanas, V. et al., "Proposed pathogenetic cascade of inclusion-body myositis: importance of amyloid-beta, misfolded proteins, predisposing genes, and aging," Curr. Opin. Rheumatol. (2003) 15(6):737-744.
Atherton et al., "The fluorenylmethoxycarbonyl amino protecting group," the Peptides: Analysis, Synthesis, Biology (1987) 9:1-38, Academic Press.
Ausubel, et al., Current Protocols in Molecular Biology (1993) Table of Contents.
Ausubel, F. et al., Short Protocols in molecular biology, 3rd Edition (1995), Table of Contents.
Ausubel, F.M. et al., Current Protocols in Molecular Biology (1989).
Author Guidelines, Journal of Neurochemistry, Version 13, Jun. 2012, 14 pages.
Auvynet, C. et al., "Structural requirements for antimicrobial versus chemoattractant activities for dermaseptin S9," FEBS J. (2008) 2754134-4151.
Awasthi et al., "Amyloid-beta causes apoptosis of newronal cells via caspase cascade, which can be prevented by amyloid-beta-derived short peptides," Exp. Neurology (2005) 196(2):282-289.
Azzazy, H.M.E. et al., "Phage display technology: clinical applications and recent innovations," Clin. Biochem. (2002) 35:425-445.
Babcook, J.S. et al., "A novel strategy for generating monoclonal antibodies from single, isolated lymphocytes producing antibodies of defined specificities," Proc. Natl. Acad. Sci. (1996) 93:7843-7848.

Bagriantsev, S. et al., "Modulation of Abeta Sub 42 low-n. oligomerization using a novel yeast reporter system," Bmc Biol. (2006) 4:32, 12 pages.
Banker, G.A. et al., "Rat hippocampal neurons in dispersed cell culture," Brain Res. (1977) 126(3):397-425.
Barany, G. et al., "Solid-phase peptide synthesis," in the Peptides: Analysis, Synthesis, Biology, (1980), Academic Press, Gross editor, vol. 2, p. 1-284.
Barbas, III, C.F. et al., "Assembly of combinatorial antibody libraries on phage surfaces: the gene III site," proc. Natl. Acad. Sci. USA (1991) 88:7978-7982.
Barrow, C.J. et al., "Solution conformations and aggregational properties of synthetic amyloid beta-peptides of Alzheimer's disease. Analysis of circular dichroism spectra," J. Mol. Biol. (1992) 225(4):1075-1093.
Bartolini, M. et al., "Insight into the kinetic of amyloid beta (1-42) peptide self-aggregation: elucidation of inhibitors' mechanism of action," Chembiochem. (2007) 8(17):2152-61.
Bateman, D. et al., "Specific binding of Alzheimer amyloid peptides to the cell surface implicates the presence of a membrane receptor," Neurobiol. Of Aging (2004) 9th International Conf. on Alzheimers Disease and Related Disorders, Philadelphia, PA, Jul. 17-22, 2004.
Bateman, R.J. et al., "Human amyloid-beta synthesis and clearance rates as measured in cerebrospinal fluid in vivo," Nature Med. (2006) 12(7):856-861.
Bates, K.A. et al., "Clearance mechanisms of Alzheimer's amyloid-Beta peptide: implications for therapeutic design and diagnostic tests," Mol. Psych. (2009) 14(5):469-486.
Bayer, T.A. et al., "Review on the APP/PS1K1 mouse model: intraneuronal A beta accumulation triggers axonopathy, neuron loss and working memory impairment," Genes Brain Behav. (2008) 7:6-11.
Bedzyk, W.D. et al., "Active site structure and antigen binding properties of idiotypically cross-reactive anti-fluorescein monoclonal antibodies," J. Biol. Chem. (1990) 265(1):133-138.
Bell, K.A. et al., MAPK recruitment by beta-amyloid in organotypic hippocampal slice cultures depends on physical state and exposure time, J. Neurochem. (2004) 91(2):349-361.
Belokon, Y.N. et al., "Improved procedures for the synthesis of (S)-24N-(N'-benzyl-prolyl)amino]benzophenoe (BPB) and Ni(II) complexes of Schiff s bases derived from Bpb and amino acids," Tetrahedron: Asymmetry (1998) 9:4249-4252.
Bennett et al., "Immunization therapy for Alzheimer disease?" Neurology (2005) 64:10-12.
Berman, D.E. et al., "Oligomeric amyloid-beta peptide disrupts phosphatidylinositol-4,5-bisphosphate metabolism," Nat. Neurosci. (2008) 11(5):547-554.
Bernstein, S.L. et al., "Amyloid beta-protein: monomer structure and early aggregation states of Abeta42 and its pro Sup 19 alloform," J. Am. Chem. Soc. (2005) 127(7):2075-2084.
Bernstein, S.L. et al., "Amyloid-beta protein oligomerization and the importance of tetramers and dodecamers in the aetiology of Alzheimer's disease," Nature Chem. (2009) 1:326-331.
Better, M. et al., "Escherichia coli secretion of an active chimeric antibody fragment," Science (1988) 240:10411043.
Bezprozvanny, I. et al., "Neuronal calcium mishandling and the pathogenesis of Alzheimer's disease," Trends Neurosci. (2008) 31(9):454-463.
Bharadwaj, P. e al., "A new method to measure cellular toxicity of non-fibrillar and fibrillar Alzheimer's Abeta using yeast," J. Alzheimer's Disease (2008) 13(2):147-150.
Bhaskar, K. et al., "The P13K-Akt-mTOR pathway regulates a oligomer induced neuronal cell cycle events," Mol. Neurodegeneration (2009) 4:1.
Bieniarz, C. et al., "Extended length heterobifunctional coupling agents for protein conjugations," Bioconjug. Chem. (1996) 7(1):88-95.
Bird, R.E. et al., "Single-chain antigen-binding proteins," Science (1988) 242:423-426.
Birren, B. et al., Genome Analysis—a Laboratory Manual, vols. 1 & 2, Table of Contents (1998).

(56) References Cited

OTHER PUBLICATIONS

Bitan, G. et al., "A molecular switch in amyloid assembly: met35 and amyloid beta-protein oligomerization," J. Am. Chem. Soc. (2003) 125:15359-15365.
Bitan, G. et al., "Amyloid beta-protein (Abeta) assembly: Abeta40 and Abeta42 oligomerize through distinct pathways," Proc. Natl. Acad. Sci. USA (2003) 100(1):330-335.
Bitan, G. et al., "Primary-quaternary structure relationships controlling early A beta oligomerizationpeptide revolution: genomics, proteomics and therapeutics," 18th American Peptide Symposium, Boston, MA Jul. 19-23, 2003, 765-767.
Bitan, G. et al., "Towards inhibition of amyloid beta-protein oligomerization," Biopolymers (2005) 80573, 19th American Peptide Symposium, San Diego, CA Jun. 18-23, 2005.
Bobich, J.A. et al., "Incubation of nerve endings with a physiological concentration of Abeta SUB 1-42 activates CaV2.2(N-type)-voltage operated calcium channels and acutely increases glutamate and noradrenaline release," J. Alzheimer's Dis. (2004) 6(3):243-255.
Bocher, W.O. et al., "Antigen-specific B and T cells in human/ouse radiation chimera following immunization in vivo," Immunol. (1999) 96:634-641.
Bombil, F. et al., "A promising model of primaray human immunization in human-scid mouse," Immuolbiol. (1996) 195:360-375.
Boridy, S. et al., "The binding of pullalan modified cholesteryl nanogels to Abeta oligomers and their suppression of cytotoxicity," Biomaterials (2009) 30(29):5583-5591.
Boss, M.A. et al., "Genetically engineered antibodies," Immunol. (1985) 6(1):12-13.
Boutaud, O. et al., "PGH SUB 2-derived levuglandin adducts increase the neurotoxicity of amyloid beta 1-42," J. Neurochem. (2006) 96(4):917-923.
Boutaud, O. et al., "Prostaglandin H2 (PGH2) accelerates formation of amyloid beta1-42 oligomers," J. Neurochem. (2002) 82:1003-1006.
Boyd-Kimball, D. et al., "Neurotoxicity and oxidative stress in D1M-substituted Alzheimer's Abeta(1-42): relevance to N-terminal methionine chemistry in small model peptides," Peptides (2005) 26:665-673.
Bravo, R. et al., "Sulfated polysaccharides promote the assembly of amyloid beta 1-42 peptide into stable fibrils of reduced cytotocity," J. Biol. Chem. (2008) 283:32471-32483.
Brettschneider, S. et al., "Decreased serum amyloid Beta1 -42 autoantibody levels in Alzheimer's disease, determined by a newly developed immuno-precipitation assay with radiolabeled amyloid beta1 -42 peptide," Biol. Psychiatry (2005) 57:813-816.
Brinkley, M.A., "A survey of methods for preparing protein conjugates with dyes, haptens and crosslinking reagents," Bioconjugate Chem. (1992) 3:2-13.
Brinkman, U. et al., "Phage display of disulfide-stabilized Fv fragments," J. Immunol. Meth. (1995) 182:41-50.
Britschgi, M. et al., "Neuroprotective natural antibodies to assemblies of amyloidogenic peptides decrease with normal aging and advancing Alzheimer's disease," Proc. Natl. Acad. Sci. USA (2009) 106(29):12145-12150.
Brorson et al., "Mutational analysis of avidity and fine specificity of anti-levan antibodies," J. Immunol. (1999) 163:6694-6701.
Brown, J.P. et al., "Protein antigens of normal and malignant human cells identified by immunoprecipitation with monoclonal antibodies," J. Biol. Chem. (1980) 255(11):4980-4983.
Brown, J.P. et al., "Structural characterization of human melanoma-associated antigen p97 with monoclonal antibodies," J. Immunol. (1981) 127(2):539-546.
Brummell et al., "Probing the combining site of an anti-carbohydrate antibody by saturation-mutagenesis: role of the heavy-chain CDR3 residues," Biochem. (1993) 32:1180-1187.
Brunger et al., "Crystallography and Nmr system: a new software suite for macromolecular structure determination," Acta Crystallogr. (1998) D54(Pt5):905-921.
Brutlag, D. "Computational Molecular Biology—Multiple Sequence Alignment," (2007).
Buchwald, H. et al., "Long-term continuous intravenous heparin administration by an implantable infusion pump in ambulatory patients with recurrent venous thrombosis," Surgery (1980) 88:507-516.
Buraei, Z. et al., "Roscovitine differentially affects CaV2 and Kv channels by binding to the open state," Neuropharmacology (2007) 52:883-894.
Burks et al., "In vitro scanning saturation mutagenesis of an antibody binding pocket," Proc. Natl. Acad. Sci. USA (1997) 94:412-417.
Burton, D.R. et al., "Human antibodies from combinatorial libraries," Adv. In Immunol. (1994) 57:191-208.
Butler, D. et al., "Cellular responses to protein accumulation involve autophagy and lysosomal enzyme activation," Rejuvenation Res. (2005) 8(4):227-237.
Carlsson, J. et al., "Protein thiolation and reversible protein-protein conjugation. N-succinimidyl 3-(2-pyridyldithio) propionate, a new heterobifunctional reagent," Biochem. J. (1978) 173(3):723-737.
Carter, D.A. et al., "More missense in amyloid gene," Nat. Genet. (1992) 2:255-256.
Carter, P. et al., "Humanization of an anti-p185HER2 antibody for human cancer therapy," Proc. Natl. Acad.Sci. (1992) 89:4285-4289.
Casset et al., "A peptide mimetic of an anti-CD4 monoclonal antibody by rational design," Biochem. Biophys. Res. Comm (2003) 307:198-205.
Catterall, W.A. et al., "International Union of Pharmacology. XLVIII. Nomenclature and structure-function relationships of voltage-gated calcium channels," Pharm. Rev. (2005) 57(4):411-425.
Cecchini, C. et al., "Increased susceptibility to amyloid toxicity in familial Alzheimer's fibroblasts," Neurobiol. Aging (2007) 28(6):863-876.
Cecchini, M. et al., "A molecular dynamics approach to the structural characterization of amyloid aggregation," J. Mol. Biol. (2006) 357(4):1306-1321.
Chacon, M.A. et al., "Frizzled-1 is involved in he neuroprotective effect of Wnt3a against Abeta oligomers," J. Cell. Physiol. (2008) 217(1):215-227.
Chaiken, I.M., "Semisynthetic peptides and proteins," CRC Crit. Rev. Biochem. (1981) 11(3):255-301.
Chamat, S. et al., "Human monoclonal antibodies isolated from spontaneous Epstein-Barr virus-transformed tumors of Hu-SPL-SCID mice and specific for fusion protein display broad neutralizing activity toward respiratory syncytial virus," J. Infect. Dis. (1999) 180:268-277.
Chander, H. et al., "Binding of trypsin to fibrililar amyloid beta-protein," Brain Res. (2006) 1082(1):173-181.
Chang, L. et al., "Femtomole immunodetection of synthetic and endogenous amyloid-beta oligomers and its application to Alzheimer's disease drug candidate screening," J. Mol. Neurosci. (2003) 20(3):305-313.
Chanki, H. et al., "Ex situ atomic force microscopy analysis of beta-amyloid self-assembly and deposition on a synthetic template," Langmuir (2006) 16(22):6977-6985.
Chen et al., "Selection and analysis of an optimized anti-VEGF antibody: crystal structure of an affinity-matured Fab in complex with antigen," J. Mol. Biol. (1999) 293:865-881.
Chen, K. et al., "Cooperation between NOD2 and toll-like receptor 2 ligands in the up-regulation of mouse mFPR2, a G-protein-coupled Aalpha SUB 42 peptide receptor, in microglial cells," J. Leukocyte Biol. (2008) 83(6): 1467-1475.
Chen, Y-R. et al., "Distinct early folding and aggregation properties of Alzheimer amyloid-beta peptides A beta 40 and A beta 42—stable trimer or tetramer formation by A beta 42," J. Biol. Chem. (2006) 281:24414-24422.
Chiang, H-C. et al., "Distinctive roles of different beta-amyloid 42 aggregates in modulation of synaptic functions," FASEB Journal (2009) 23(6):1969-1977.
Chiang, P.K. et al., "The many faces of amyloid beta in Alzheimer's disease," Curr. Mol. Med. (2008) 8(6):580584.
Chiarini, a. et al., "Calcium-sensing receptor (CaSR) in human brain's pathophysiology: roles in late-onset Alzheimer's disease (LOAD)," Curr. Pharma. Biotech. (2009) 10(3):317-326.

(56) References Cited

OTHER PUBLICATIONS

Choo-Smith, LP et al., "The interaction between Alzheimer amyloid beta (1-40) peptide and ganglioside Gmicontaining membranes," FEBS Lett. (1997) 402:95-98.

Chothia, C. et al., "Canonical structures for the hypervariable regions of immunoglobulins," J. Mol. Biol. (1987) 196:901-917.

Chothia, C. et al., "Conformations of immunoglobulin hypervariable regions," Nature (1989) 342:877-883.

Chothia, C. et al., "Structural repertoire of the human VH segments," J. Mol. Biol. (1992) 227:799-817.

Chrisey, L. et al., "Covalent attachment of synthetic DNA to self-assembled monolayer films," Nucl. Acids. Res. (1996) 24(15):3031-3039.

Christensen, D.D., "Changing the course of Alzheimer's disease: anti-amyloid disease-modifying treatments on the horizon," Primary Care Companion J. Clin. Psych. (2007) 9(1):32-41.

Chromy, B.A. et al., "Stability of small oligomers of Abetal -42( ADDLs)," Society for Neuroscience Abstracts (1999) Abstract No. 252129, 29th Annual Meeting of the Society for Neuroscience, Miami Beach, FL, Oct. 23-28, 1999.

Chung, H. et al., "Degradation of beta-amyloid peptide by microglia," Society for Neuroscience Abstracts (2000) 26 Abstract No. 858.10, 30th Annual Meeting of the Society of Neuroscience, New Orleans, LA, Nov. 4-9, 2000.

Ciccotosto, G.B. et al., "Methionine oxidation: implications for the mechanism of toxicity of the beta-amyloid peptide from Alzheimer's disease," Lett. Peptide Sci. (2003) 10(5-6):413-417.

Clackson, T. et al., "Making antibody fragments using phage display libraries," Nature (1991) 352:624-628.

Clark, M.S., Plant Molecular Biology—A Laboratory Manual, Table of Contents (1997).

Cleary, J.P. et al., "Cognitive effects of oligomeric and fibril Abeta in rats," Soc. For Neuroscience Abstract Viewer and Itinerary Planner (2002) Abstract No. 882.2, 32nd Annual meeting of the Society for Neuroscience, Orlando, FL, Nov. 2-7, 2002.

Cleek, R.L. et al., "Biodegradable polymeric carriers for a bFGF antibody for cardiovascular application," Proc. Intl. Symp. Control. Re. Bioact. Mater. (1997) 24:853-854.

Co, M.S. et al., "Genetically engineered deglycosylation of the variable domain increases the affinity of an anti-Cd33 monoclonal antibody," Molec. Immunol. (1993) 30(15):1361-1367.

Cole, G.M. et al., "Alzheimer's amyloid story finds its star," Trends Mol. Med. (2006) 12(9):395-396.

Cole, G.M. et al., "Cat and mouse," Neuron (2006) 51(6):671-672.

Cole, G.M. et al., "Docosahexaenoic acid protecs from amyloid and dendritic pathology in an Alzheimer's disease mouse model," Nutrition and Health (2006) 18(3):249-259.

Cole, M.S. et al., "Human IgG2 variants of chimmeric anti-CD3 are nonmitogenic to T cells," J. Immunol. (1997) 159(7):3613-3621.

Colman, P.M., "Effects of amino acid sequence changes on antibody-antigen interactions," Research in Immunol (1994) 145:33-36.

Colombo, R. et al., "Ce can identify small molecules that selectively target soluble oligomers of amyloid beta protein and display antifibrillogenic activity," Electrophoresis (2009) 30(8):1418-1429.

Costantini, C. et al., "The expression of p75 neurotrophin receptor protects against the neurotoxicity of soluble oligomers of beta-amyloid," Exp. Cell Res. (2005) 311(1):126-134.

Craft, J.M. et al., "Enhanced susceptibility of S-100B transgenic mice to neuroinflammation and neuronal dysfuntion induced by intracerebroventricular infusion of human beta-amyloid," Glia (2005) 51(3):209-216.

Crouch, P.J. et al., "Soluble oligomeric amyloid beta 1-42 specifically inhibits cytochrome c oxidase of human mitochondria," Mitochondrial Medicine (2004) Pittsburg, PA, Aug. 4-7, 2004), Mitochondrion (2004) 471-472.

Crouse, N.R. et al., "Oligomeric amyloid-beta(1-42) induces THP-1 human monocyte adhesion and maturation," Brain Res. (2009) 1254:109-119.

Dahlgren, K.N. et al., "Oligomeric and fibrillar species of amyloid-beta peptides differentially affect neuronal viability," J. Biol. Chem. (2002) 277(35):32046-32053.

Das, U. et al., "Interface peptide of Alzheimer's amyloid beta: application in purification," Biochem. Biophys. Res. Commun (2007) 362(2):538-542.

Dasilva, K.A. et al., "Reduced oligomeric and vascular amyloid-beta following immunization of TgCRND8 mice with an Alzheimer's DNA vaccine," Vaccine (2009) 27136-1376.

De Felice, F.G. et al., "Alzheimer's disease-type neuronal tau hyperphosphorylation induced by Abeta oligomers," Neurobiol. Aging (2008) 29(9):1334-1347.

De Pascalis, R. et al., "Grafting of 'abbreviated' complementarity-determining regions containing specificity-determining residues essential for ligand contact to engineer a less immunogenic humanized monoclonal antibody," J. Immunol. (2002) 169:3076-3084.

Dealmeida, E.R.P. et al., "Transgenic expression of two marker genes under the control of an arabidopsis rbcS promoter: sequences encoding the Rubisco transit peptide increase expression levels," Mol Gen. Genet. (1989) 218:78-86.

deChaves, P.E. et al., "Lipid rafts in amyloid beta endocytosis and amyloid beta-induced apoptosis," J. Neurochem. (2009) 110(2):146, S20-23.

DeMattos et al., "P4-358 in vitro and in vivo characterization of beta-amyloid antibodies binding to cerebral amyloid angiopathy (CAA) and the selective exacerbation of CAA-associated microhemorrhage," Neurobiol. Aging (2004) 25(S2):S577.

DeMattos, R.B. et al., "Peripheral anti-Abeta antibody alters CNS and plasma Abeta clearance and decreases brain Abeta burden in a mouse model of Alzheimer's disease," Proc. Natl. Acad. Sci. USA (2001) 98(15):88508855.

Demeester, N. et al., "Comparison of the aggregation properties, secondary structure and apoptotic effects of wild-type, Flemish and Dutch N-terminally truncated amyloid beta peptides," Euro. J. Neurosci. (2001) 13(11):2015-2024.

Demuro, A. et al., "Calcium dysregulation and membrane disruption as a ubiquitous neurotoxic mechanism of soluble amyloid oligomers," J. Biol. Chem. (2005) 280(17):17294-17300.

Denkewalter et al., "Fortschritte der arzneimittelforschung progress in drug research progres des receherches pharmaceutiques," (1996) 10:224-285.

Dewachter, I. et al., "Neuronal deficiency of presenillin 1 inhibits amyloid plaque formation and corrects hippocampal long-term potentiation but not a cognitive defect of amyloid precursor protein [V7171] transgeneic mice," J. Neurosci. (2002) 22(9):3445-3453.

Dickson, D.W. et al., "Correlations of synaptic and pathological markers with cognition of the elderly," Neurobiol. Aging (1995) 16(3):285-304.

Dillen, K. et al., "A two decade contribution of molecular cell biology to the centennial of Alzheimer's disease: are we progressing toward therapy?" Int. Rev. Cytol. (2006) 254:215-300.

Dingledine, R. et al., Brain slices, Plenum Press (1984) Table of Contents.

Donnet et al., "Plasma treatment effect on the surface energy of carbon and carbon fibers," Carbon (1986) 24(6):757-770.

Du, Y. et al., "Reduced levels of amyloid beta-peptide antibody in Alzheimer disease," Neurology (2001) 57:801805.

Dufner, P. et al., "Harnessing phage and ribosome display for antibody optimisation," Trends Biotech. (2006) 24(11):523-529.

During, M.J. et al., "Controlled release of dopamine from a polymeric brain implant: in vivo characterization," Ann. Neurol. (1989) 25:351-356.

Durocher, Y. et al., "High-level and high-throughput recombinant protein prouction by transient transfection of suspension-growing human 293-EBNA1 cells," Nucl. Acid. Res. (2002) 30(2):e9-11.

Eckenhoff, R.G. et al., "Anesthetics and neurodegenerative disorders: a molecular basis for concern?" Anesthesiology Abstracts of Scientific Papers Annual Meeting, 2003, Abstract No. A-848, 2003 Annual Meeting of the American Society of Anesthesiologists, San Francisco, CA, Oct. 11-15, 2003.

Eckert, A. et al., "Oligomeric and fibrillar species of beta-amyloid (A beta 42) both impair mitochondrial function in P301L tau transgenic mice," J. Mol. Med. (2008) 86(11):1255-67.

(56) References Cited

OTHER PUBLICATIONS

Eisenberg et al., "Analysis of membrane and surface protein sequences with the hydrophobic moment plot," J. Mol. Biol. (1984) 179(1):125-142.
Englund, H. et al., Oligomerization partially explains the lowering of A beta 42 in Alzheimer's disease cerebrospinal fluid, Neurodegenerative Dis. (2009) 6:139-147.
Eren, R. et al., "Human monoclonal antibodies specific to hepatitis B virus generated in a human/mouse radiation chimera: the Trimera system," Immunol. (1998) 93:154-161.
Esteras-Chopo, A. et al., "New strategy for the generation of specific D-peptide amyloid inhibitors," J. Mol. Biol. (2008) 377:1372-1381.
Evans et al., "Design of a nonpeptidal ligands for a peptide receptor: cholecystokinin antagonists," J. Med. Chem. (1987) 30:1229.
Evans, C.G. et al., "Heat shock proteins 70 and 90 inhibit early stages of amyloid beta-(1-42) aggregation in vitro," J. Biol. Chem. (2006) 281:33182-33191.
Evans, N. A. et al., "Abeta Sub 1-42 reduces synapse number and inhibits neurite outgrowth in primary cortical and hippocampal neurons: a quantitative analysis," J. Neurosci. Methods (2008) 175(1):96-103.
Evin, G., "gamma-secretase modulators: hopes and setbacks for the future of Alzheimer's treatment," Expert Rev. Neurother. (2008) 8(11):1611-1613.
Fauchere, "Elements for the rational design of peptide drugs," Adv. Drug Res. (1986) 15:29-69.
Feld, M. et al., "Effect on memory of acute administration of naturally secreted fibrils and synthetic amyloid-beta peptides in an invertebrate model," Neurobiol. Learn. Mem. (2008) 89(4):407-418.
Ferrao-Gonzales, A et al., "Controlling beta-amyloid oligomerization by the use of naphthalene sulfonates: trapping low molecular weight oligomeric species," J. Biol. Chem. (2005) 280(41):34747-34754.
Fishwild, D.M. et al., "High-avidity human IgGx monoclonal antibodies from a novel strain of minilocus transgenic mice," Nature Biotech. (1996) 14:845-851.
Flink, M.T. et al., "Ca2+ channels as targets of neurolgoical disease: Lambert-Eaton Syndrome and other Ca2+ channelopathies," J. Bioeng. Biomembr. (2003) 35(6):697-718.
Foote, J. et al., "Antibody framework residues affecting the conformation of the hypervariable loops," J. Mol. Biol. (1992) 224:487-499.
Forsell, C. et al., "Amyloid precursor protein mutation at codon 713 (Ala→Val) does not cause schizophrenia: non-pathogenic variant found at codon 705 (silent)," Neurosci. Lett. (1995) 184:90-93.
Fradinger, E.A. et al., "C-terminal peptides coassemble into Abeta42 oligomers and protect neurons against Abeta42-induced neurotoxicity," Proc. Natl. Acad. Sci. USA 2008) 105(37):14175-14180.
Fuchs, P. et al., "Targeting recombinant antibodies to the surface of escherichia coli: fusion to a peptidoglycan associated lipoprotein," BioTech. (1991) 9:1369-1372.
Funke, S.A. et al., "Detection of amyloid-beta aggregates in body fluids: a suitable method for early diagnosis of Alzheimer's disease?" Current Alzheimer's Research (2009) 6(3):285-289.
Galfre, G. et al., "Antibodies to major histocompatibility antigens produced by hybrid cell lines," Nature (1977) 266(5602):550-552.
Gallo, M.L. et al., "The human immunoglobulin loci introduced into mice: V(D) and J gene segment usage similar to that of adult humans," Eur. J. Immunol. (2000) 30:534-540.
Garrard, L.J. et al., "Fab assembly and enrichment in a monovalent phage display system," BioTech. (1991) 9:1373-1377.
Garzon, D.J. et al., "Oligomeric amyloid decreases basal levels of brain-derived neurotrophic factor (BDNF) mRNA via specific downregulation of BDNF transcripts IV and V in differentiated human neuroblastoma cells," J. Neurosci. (2007) 27(10):2628-2635.
Gavilondo, J.V. et al., "Antibody engineering at the millennium," BioTechniques (2002) 29:128-145.
Gefter, M.L. et al., "A simple method for polyethylene glycol-promoted hybridization of mouse myeloma cells," Somatic Cell Genetics (1997) 3(2):231-236.

Gervais, F. et al., "Targeting soluble Abeta peptide with tramiprosate for the treatment of brain amyloidosis," Neurobiol. Aging (2007) 28(4):537-547.
Ghiso, J. et al., "Systemic catabolism of Alzheimer's Abeta40 and Abeta42," J. Biol. Chem. (2004) 279:4589745908.
Ghosal, K. et al., "Alzheimer's disease-like pathological features in transgenic mice expressing the APP intracellular domain," Proc. Natl. Acad. Sci. (2009) 106(43):18367-18372.
Giacobini, E. et al., "One hundred years after the discovery of Alzheimer's disease. A turning point for therapy? the multifaceted aspects of Alzheimer's disease: from social to molecular problems," J. Alzheimer's Disease (2007) 12(1):37-52.
Gibbs, M.E. et al., "Rescue of Abeta Sub 1-42-induced memory impairment in day-old chick by facilitation of astrocytic oxidative metabolism: implications for Alzheimer's disease," J. Neurochem. (2009) 109 Suppl. 1:230-236.
Giege, R. et al., "An introduction to the crystallogenesis of biological macromolecules," Crystallization of Nucleic Acids & Proteins, a Practical Approach, 2nd Edition: 1-16 (1999).
Giliberto, L. et al., "Mutant presenilin 1 increases the expression and activity of BACE1," J. Biol. Chem. (2009) 284(14):9027-9038.
Gillies, S.D. et al., "High-level expression of chimeric antibodies using adapted cDNA variable region cassettes," J. Immunol. Meth. (1989) 125:191-202.
Giuffrida, M.L. et al., "A beta(25-35) and its C- and/or N-blocked derivatives: copper driven structural features and neurotoxicity," J. Neursci. Res. (2007) 85:623-633.
Giuffrida, M.L. et al., "Beta-amyloid monomers are neuroprotective," J. Neurosci. (2009) 29(34):10582-10587.
Goeddel, D., "Systems for heterologous gene expression," Meth. In Enzymol. (1990) 185:3-7.
Goldspiel, B.R. et al., "Human gene therapy," Clin. Pharm. (1993) 12:488-505.
Gonzalo-Ruiz, a. et al., "Oligomers of beta-amyloid (1-42) peptide induce co-localization of AB and TAU proteins associated with calpain activity," J. Neurochem. (2009) 110:57-58.
Goodson, J.M., "Dental applications" in Medical Applications of Controlled Release, (1984) vol. II, Chapter 6, 115-138.
Gowing, E. et al., "Chemical characterization of a beta 17-42 peptide, a component of diffuse amyloid deposits of Alzheimer disease," J. Biol. Chem. (1994) 269:10987-10988.
Grabarek, Z. et al., "Zero-length crosslinking procedure with the use of active esters," Anal. Biochem. (1990) 185(1):131-135.
Grabowski, T.J. et al., "Novel amyloid precursor protein mutation in an Iowa family with dementia and severe cerebral amyloid angiopathy," Ann. Neurol. (2001) 49(6):697-705.
Grace, S.Y. et al., "Abeta induces oxidative-degradative stress through NADPH oxidase and phopholipase A2," J. Neurochem. (2009) 110222, 22nd Biennial Meeting of the International Society of Neurochemistry, South Korea, Aug. 23-29, 2009.
Gram, H. et al., "In vitro selection and affinity maturation of antibodies from a naïve combinatorial immunoglobulin library," Proc. Natl. Acad. Sci. USA (1992) 89:3576-3580.
Grange, P.De La. et al., "FAST DB: a website resource for the study of the expression regulation of human gene products," Nucl. Acids Res. (2005) 33(13):4276-4284.
Green, L.L. et al., "Antigen-specific human monoclonal antibodies from mice engineered with human Ig heavy and light chain YACs," Nature Genetics (1994) 7(1):13-21.
Green, L.L. et al., "Regulation of B cell development by variable gene complexity in mice reconsituted with human immunoglobulin yeast artificial chromosomes," J. Exp. Med. (1998) 188(3):483-495.
Green, L.L., "Antibody engineering via genetic engineering of the mouse: XenoMouse strains are a vehicle for the facile generation of therapeutic human monoclonal antibodies," J. Immunol. Meth. (1999) 231:11-23.
Griffiths, a.D. et al., "Human anti-self antibodies with high specificity from phage display libraries," the Embo Journal (1993) 12(2):725-734.
Guo, L. et al., "Apoe down regulates pro-inflammatory responses induced by oligomeric Abeta in activated glia," Soc. For Neurosci.

(56) References Cited

OTHER PUBLICATIONS

Abstract Viewer and Itinerary Planner (2002), Abstract No. 883.12, 32nd Annual meeting of the Society for Neuroscience, Orlando, FL, Nov. 2-7, 2002.
Ha, C. et al., "Ex situ atomic force microscopy analysis of beta-amyloid self-assembly and deposition on a synthetic template," Langmuir (2006) 22:6977-6985.
Ha, C. et al., "Metal ions differntially influence the aggregation and deposition of Alzheimer's beta-amyloid on a solid template," Biochem. (2007) 46(20):6118-6125.
Ha, H.J. et al., "Development of herbal medicine for Alzheimer's disease from RHEI rhizoma," J. Neurochem. (2009) 110114.
Haas S, C. et al., "Soluble protein oligomers in neurodegeneration: lessons from the Alzheimer's amyloid beta-peptide," Nat. Rev. Mol. Cell Biol. (2007) 8(2):101-112.
Hachiya, N. S. et al., "Oligomeric Aip2p/Dld2p modifies the protein conformation of both properly folded and misfolded substrates in vitro," Biochem. Biophys. Res. Comm (2004) 323(1):339-344.
Hagemeyer, C.E. et al., "Single-chain antibodies as diagnostic tools and therapeutic agents," Thromb. Haemost. (2009) 101:1012-1019.
Halladay, M.W. et al., "Synthesis of hydroxyethelene and ketomethylene dipeptide isosteres," Tetrahedron Lett. (1983) 24:4401-4404.
Hann, M.M., "On the double bond isostere of the peptide bond: preparation of an enkephalin analogue," J. Chem. Soc. Perkin Transactions (1982) 1:307-314.
Harding, F.A. et al., "Class switching in human immunoglobulin transgenic mice," Ann. N. Y. Acad. Sci. (1995) 764:536-546.
Hardy, J. et al., "The amyloid hypothesis of Alzheimer's disease: progress and problems on the road to therapeutics," Science (2002) 297:353-356.
Harris-White, M.E. et al., "Effects of low dose, low Mw soluble amyloid oligomers on spatial memory performance," Society for Neurosci. Abstr. Viewer and Itin. Plann. (2003) Abstract No. 240.11, 33rd Annual Meeting of the Society of Neuroscience, Nov. 8-12, 2003, New Orleans.
Hartley, D.M. et al., "Transglutaminase induces protofibril-like amyloid beta-protein assemblies that are protease-resistant and inhibit long-term potentiation," J. Biol. Chem. (2008) 283(24):16790-16800.
Hashida, S. et al., "More useful maleimide compounds for the conjugation of Fab to horseradish peroxidase through thiol groups in the hinge," J. Appl. Biochem. (1984) 6:56-63.
Hashimoto, M. et al., "Role of protein aggregation in mitochondrial dysfunction and neurodegeneration in Alzheimer's and Parkinson's disease," Neuromol. Med. (2003) 4(1-2):21-36.
Hawkins, R.E., "Selection of phage antibodies by binding affinity—imicking affinity maturation," J. Mol. Biol. (1992) 226:889-896.
Hay, B.N. et al., "Bacteriophage cloning and escherichia coli expression of a human IgM fab," Hum. Antibod. Hybridomas (1992) 3:81-85.
Hayes, G.M. et al., "Production of beta-amyloid by primary human foetal mixed brain cell cultures and its modulation by exogeneous soluble beta-amyloid," Neurosci. (2002) 113(3):641-646.
Head, E. et al., "A two-year study with fibrillar beta-amyloid (Abeta) immunization in aged canines: effects on cognitive function and brain Abeta," J. Neurosci. (2008) 28(14):3555-3566.
Head, E. et al., "The efffects of immunization with fibrillar or oligomeric Abeta in the brain and CSF of aged canines: a pilot study," Society for Neuroscience Abstract Viewer and Itinerary Planner (2003) Abstract No. 525.24, 33rd Annual Meeting of the Society of Neuroscience, New Orleans, LA, Nov. 8-12, 2003.
Heard, C. et al., "Two neutralizing human anti-Rsv antibodies: cloning, expression, and characterization," Molec. Med. (1999) 5:35-45.
Heinitz, K. et al., "Toxicity mediated by soluble oligomers of beta-amyloid(1-42) on cholinergic SN56.B5.G4 cells," J. Neurochem. 92006) 98(6):1930-1945.
Helisalmi, S. et al., "Screening for amyloid beta precursor protein codon 665, 670/671 and 717 mutations in Finnish patients with Alzheimer's disease," Neurosci. Lett. (1996) 205:68-70.

Herz, U. et al., "The humanized (Hu-PBMC) SCID mouse as an in vivo model for human IgE production and allergic inflammation of the skin," Int. Arch Allergy Immunol. (1997) 113(1-3):150-152.
Hess et al., "cooperation of glycolytic enzymes," J. Adv. Enzyme Reg. (1968) 7:149-167.
Hieter, P.A. et al., "Evolution of human immunoglobulin kJ region genes," J. Biol. Chem. (1982) 257(3):15161522.
Higgins, D.G. et al., "Fast and sensitive multiple sequence alignments on a microcomputer," Cabios Comm (1989) 5(2):151-153.
Higuchi, R., "Using PCR to engineer DNA," PCR Technol: Princ. & Appl. For DNA Amplification (1989) 61-70.
Hilbich, C. et al., "Aggregation and secondary structure of synthetic amyloid betaA4 peptides of Alzheimer's disease," J. Mol. Biol. (1991) 218:149-163.
Hirko, A.C. et al., "Peripheral transgene expression of plasma gelsolin reduces amyloid in transgenic mouse models of Alzheimer's disease," Mol. Ther. (2007) 15(9):1623-9.
Hock, C. et al., "Clinical observations with AN-1792 using TAPIR analyses," Neurodegenerative Dis. (2006) 2(5):273-276.
Holliger, P. et al., ""Diabodies" small bivalent and bispecific antibody fragments," Proc. Natl. Acad. Sci. (1993) 90:6444-6448.
Holm et al., "Functional mapping and single chain construction of the anti-cytokeratin 8 monoclonal antibody TS1," Mol. Immunol. (2007) 44:1075-1084.
Hong, H-S. et al., "Combining the rapid MTT formazan exocytosis assay and the MC65 protection assay led to the discovery of carbozole analogs as small molecule inhibitors of Abeta oligomer-induced cytotoxicity," Brain Res. (2007) 1130(1):223-234.
Hong, H-S. et al , "Inhibition of Alzheimer's amyloid toxocity with a tricyclic pyrone molecule in vitro and in vivo," J. Neurochem. (2009) 108(4):1097-1108.
Hoogenboom, H.R. et al., "Multi-subunit proteins on the surface of silamentous phage: methodologies for displaying antibody (Fab) heavy and light chains," Nucl. Acids Res. (1991) 19(15):4133-4137.
Hoogenboom, H.R. et al., "Natural and designer binding sites made by phage display technology," Immunol. Today (2000) 21(8):371-378.
Hoogenboom, H.R., "Designing and optimizing library selection strategies for generating high-affinity antibodies," Tibtech (1997) 15:62-70.
Hoozemans, J.J.M. et al., "Always around, never the same: pathways of amyloid beta induced neurodegeneration throughout the pathogenic cascade of Alzheimer's disease," Curr. Med. Chem. (2006) 13(22):2599-2605.
Hos Sain, S. et al., "Mechanism of docosahexaenoic acid-induced inhibition of in vitro Abetal -42 fibrillation and Abetal-42-induced toxicity in Sh-S5Y5 cells," J. Neurochem. (2009) 111(2):568-579.
Howard III, M.A. et al., "Intracerebral drug delivery in rats with lesion-induced memory deficits," J. Neurosurg. (1989) 71:105-112.
Howlett, D.R. et al., "The pathology of APP transgenic mice: a model of Alzheimer's disease or simply overexpression of APP?" Histol. Histopathol. (2009) 24(1):83-100.
Hoyer, W. et al., "Stabilization of a beta-hairpin in monomeric Alzheimer's amyloid-beta peptide inhibits amyloid formation," Natl. Acad. Sci. Proc. Natl. Acad. Sci. (2008) 105(13):5099-5104.
Hruby, V.J., "Conformational restrictions of biologically active peptides via amino acid side chain groups," Life Sci. (1982) 31:189-199.
Hsiao et al., "Correlative memory deficits, abeta elevation, and amyloid plaques in transgenic mice," Science (1996) 274(5284):99-102.
Huang, C. et al., "Isoproterenol potentiates synaptic transmission primarily by enhancing presynaptic calcium influx via P- and/or Q-type calcium channels in the rat amygdala," J. Neurosci. (1996) 16(3):1026-1033.
Huang, C.C. et al., "Selective enhancement of P-type calcium currents by isoproterenol in the rat amygdata," J. Neurosci. (1998) 18(6):2276-2282.
Huang, X. et al., "Metal - dependence of Abeta oligomerization," Soc. For Neurosci. Abstract Viewer and Itinerary Planner (2002), Abstract No. 19.1, 32nd Annual meeting of the Society for Neuroscience, Orlando, FL, Nov. 2-7, 2002.

(56) References Cited

OTHER PUBLICATIONS

Huse, W.D. et al., "Generation of a large combinatorial library of the immunoglobulin repertoire in phage lambda," Science (1989) 246:1275-1281.

Huston, J.S. et al., "Protein engineering of antibody binding sites: recovery of specific activity in all anti-digoxin single-chain Fv analogue produced in *Escherichia coli*," PNAS (1988) 85:5879-5883.

Huston, J.S. et al., "Protein engineering of single-chain Fv analogs and fusion proteins," Meth. In Enzymol. (1991) 203:46-88.

Hutchins, W.A. et al., "Human immune response to a peptide mimic of neisseria meningitis serogroup C in huPBMC-SCID mice," Hybridoma (1999) 18(2):121-129.

Hyman et al., "Autoantibodies to Amyloid-beta and Alzheimer's disease," Ann. Neurol. (2001) 49:808-810.

Iijima, K. et al., "A beta 42 mutants with different aggregation profiles induce distinct pathologies in drosophila," PLoS One (2008) 3 Article No. E1703.

Ilan, E. et al., "The hepatitis B virus-trimera mouse: a model for human HBV infection and evaluation of anti-HBV therapeutic agents," Hepatology (1999) 29:553-562.

Ingelbrecht, I.L.W. et al., "Different 3' end regions strongly influence the level of gene expression in plant cells," The Plant Cell (1989) 1:671-780.

Jang et al., "The structural basis for DNA binding by an anti-DNA autoantibody," Molec. Immunol. (1998) 35:1207-1217.

Janssen, J.C. et al., "Early onset familial Alzheimer's disease: mutation frequency in 31 families," Neurology (2003) 60(2):235-239.

Jefferis, R., "Glycosylation of recombinant antibody therapeutics," Biotechnol. Prog. (2005) 21:11-16.

Jennings-White, C. et al., "Synthesis of ketomethylene analogogs of dipeptides," Tetrahedr. Lett. (1982) 23(25):2533-2534.

Jensen, M.T. et al., "Lifelong immunization with human beta-amyloid (1-42) protects Alzheimer's transgenic mice against cognitive impairment throughout aging," Neurosci. (2005) 130:667-684.

Jiang, S. et al., "Recent progress of synthetic studies to peptide and peptidomimetic cyclization," Curr. Org. Chem. (2008) 12(17):1502-1542.

Joerchel, S. et al., "Oligomeric beta-amyloid(1-42) induces the expression of Alzheimer disease-relevant proteins in cholinergic SN56.B5.G4 cells as revealed by proteomic analysis," Int. J. Developm. Neurosci. (2008) 26(3-4):301-308.

Johansson, A.S. et al., "Attenuated amyloid-beta aggregation and neurotoxicity owing to methionine oxidation," NeuroReport (2007) 18(6):559-563.

Johansson, A.S. et al., "Dramatic changes in fibrillization rate and oligomer/protofibrillar formation of beta-amyloid peptide with oxidized methionine: implications for novel therapeutic approaches in Alzheimer's disease," Soc. For Neurosci. Abstract Viewer and Itinerary Planner (2002), Abstract No. 123.8, 32nd Annual meeting of the Society for Neuroscience, Orlando, FL, Nov. 2-7, 2002.

Johansson, A-S. et al., "Docosahexaenoic acid stabilizes soluble amyloid-beta protofibrils and sustains amyloid-beta-induced neurotoxicity in vitro," FEBS J. (2007) 274(14):990-1000.

Johansson, A-S. et al., "Physiochemical characterization of the Alzheimer's disease-related peptides Abetal-42Arctic and Abetal-42wt," FEBS Journal (2006) 273(12):2618-2630.

Johnsson, B. et al., "Comparison of methods for immobilozation to carboxymethyl dextran sensor surfaces by analysis of the specific activity of monoclonal antibodies," J. Mol. Rec. (1995) 8:125-131.

Johnsson, B. et al, "Immobilizataion of progeins to a carboxymethyldextran-modified gold surface for biospecific interaction analysis in surface plasmon resonance sensors," Anal. Biochem. (1991) 198:268-277.

Joliot, A. et al., "Antennapedia homeobox peptide regulates neural morphogenesis," Proc. Natl. Acad. Sci. USA (1991) 88:1864-1868.

Jones, C.T. et al., "Mutation in codon 713 of the beta-amyloid precursor protein gene presenting with schizophrenia," Nat. Genet. (1992) 1(4):306-309.

Jones, J.D.G. et al., "High level expression of introduced chimaeric genes in regenerated transformed plants," EMBO J. (1985) 4(10):2411-2418.

Jonsson, U. et al., "Introducing a biosensor based technology for real-time biospecific interaction analysis," Ann. Biol. Clin. (1993) 51:19-26.

Jonsson, U. et al., "Real-time biospecific interaction analysis using surface plasmon resonance and a sensor chip technology," BioTechniques (1991) 11(5):620-627.

Jungbauer, L.M. et al., "Preparation of fluorescently-labeled amyloid-beta peptide assemblies: the effect of luorophore conjugation on structure and function," J. Mol. Recogn. (2009) 22(5):403-413.

Kabat, E.A. et al., "Attempts to locate complementarity-determining residues in the variable positions of light and heavy chains," Ann. NY Acad. Sci. (1971) 190:382-391.

Kabat, E.A. et al., Sequences of Proteins of Immunological Interest, 5th Edition, NIH Publ. #91/3242 (1981), Table of Contents.

Kaiser et al., "Peptide and protein synthesis by segment synthesis-condensation," Science (1989) 243:187.

Kakio, A. et al., "Interactions of amyloid beta-protein with various gangliosides in raft-like membranes: importance of GM1 ganglioside-bound form as an endogenous seed fr Alzheimer amyloid," Biochem. (2002) 41:7385-7390.

Kamino, K. et al., "Linkage and mutational analysis of familial Alzheimer disease kindreds for the APP gene region," Am. J. Hum. Genet. (1992) 51(5):998-1014.

Kanemitsu, H. et al., "Human neprilysin is capable of degrading amyloid beta peptide not only in the monomeric form but also the pathologica oligomeric form," Neursci. Lett. (2003) 350:113-116.

Kaufman, R.J. et al., "Amplification and expression of sequences contrasfected with a modular dihydrofolate reductase complementary DNA gene," Mol. Biol. (1982) 159:601-621.

Kawarabayashi, T. et al., "Age-dependent changes in brain, CSF, and plasma amyloid beta protein in the Tg2576 transgenic mouse model of Alzheimer's disease," J. Neurosci. (2001) 21(3):372-381.

Kawarabayashi, T. et al., "Dimeric amyloid beta protein rapidly accumulates in lipid rafts followed by apolipoprotein E and phosphorylated Tau accumulation in the Tg2576 mouse model of Alzheimer's disease," J. Neurosci. (2004) 24(15):3801-3809.

Kellermann, S-A. et al., "Antibody discovery: the use of transgenic mice to generate human monoclonal antibodies for therapeutics," Curr. Opin. In Biotechnol. (2002) 13:593-597.

Kenneth, R.H. In Monoclonal Antibodies: A New Dimension in Biological Analyses, Plenum Publishing Corp. New York, New York (1980).

Kent, S.B.H., "Chemical synthesis of peptides and proteins," Ann. Rev. Biochem. (1988) 57:957-989.

Keowkase, R. et al., "Mechanism of Cns drugs and their combinations for Alzheimer's disease," Central Nervous System Agents in Medicinal Chemistry (2008) 8(4):241-248.

Kettleborough, C.A. et al., "Isolation of tumor cell-specific single-chain Fv from immunized mice using phage-antibody libraries and the re-construction of whole antibodies from these antibody fragments," Eur. J. Immunol. (1994) 24:952-958.

Kim, N.D. et al., "Putative therapeutic agents for the learning and memory deficits of people with Down syndrome," Bioorg. Med. Chem. Lett. (2006) 16(14):3772-3776.

Kim, Y.S. et al., "Biological tuning of synthetic tactics in solid-phase synthesis: application to Abeta(1-42)" J. Org. Chem. (2004) 69(22):7776-7778.

Kipriyanov, S.M. et al., "Recombinant single-chain Fv fragments carrying C-terminal cysteine residues: production of bivalent and biotinylated miniantibodies," Mol. Immun (1994) 31(14):1047-1058.

Kipriyanov, S.M. et al., "Single-chain antibody streptavidin fusions: tetrameric bifunctional scFv-complexes with biotin binding activity and enhanced affinity to antigen," Hum. Antibod. Hybridomas (1995) 6(3):93-101.

Kirkitadze, M.d. et al., "Identification and characterization of key kinetic intermediates in amyloid B-protein fibrillogenesis," J. Mol. Biol. (2001) 312:1103-1119.

(56) References Cited

OTHER PUBLICATIONS

Kitamura, Y. et al., "Stress proteins and regulation of microglial amyloid-beta phagocytosis," Folia Pharmacologica Japonica (2004) 124(6):407-413.
Kitchin, K. et al., "Cloning, expression, and purification of an anti-desipramine single chain antibody in NS/0 myeloma cells," J. Pharm. Sci. (1995) 84(10):1184-1189.
Klafki, H-W. et al., "Electrophoretic separation of beta-A4 peptides (1-40) and 1-42)," Anal. Biochem. (1996) 237:24-29.
Klyubin, I. et al., "Amyloid beta-protein (abeta) bearing the arctic mutation is a more potent inhibitor of LTP than wild type Abeta," Society for Neuroscience Abstract Viewer and Itinerary Planner (2003), 2003 Abstract No. 904.13, 33rd Annual Meeting of the Society of Neuroscience, New Orleans, LA, Nov. 8-12, 2003.
Knappik, a. et al., "Fully synthetic human combinatorial antibody libraries (hUCAL) based on modular consensus frameworks and CDRs randomized with trinucleotides," J. Mol. Biol. (2000) 296:57-86.
Knowles, J.K. et al., "The p75 neurotrophin receptor promotes amyloid-beta(1-42)-induced neuritic dystrophy in vitro and in vivo," J. Neurosci. (2009) 29:10627-10637.
Kobayashi et al., "Tryptophan H33 plays an important role in Pyrimidine (6-4) pyrimidone photo product binding by a high-affinity antibody," Protein Eng. (1999) 12:879-884.
Koh, S-H. et al., "Amyloid-beta-induced neurotoxicity is reduced by inhibition of glycogen synthase kinase-3," Brain Res. (2008) 1188:254-262.
Kohler, "Continuous cultues of fused cells secreting antibody of predefined specificity," Nature (1975) 256:495497.
Kokubo, H. et al., "Oligomeric proteins ultrastructurally localize to cell processes, especially to axon terminals with higher density, but not to lipid rafts in Tg2576 mouse brain," Brain Res. (2005) 1045(1-2):224-228.
Kontermann, Antibody Engineering, Springer-Verlag, Berlin, Table of Contents (2001).
Kooistra, J. et al., "A new function of human htra2 as an amyloid-beta oligomerization inhibitor," J. Alzheimer's Disease (2009) 17(2):281-294.
Kortekaas, P. et al., "Development of HVA and LVA calcium currents in pyramidal CA1 neurons in the hippocampus of the rat," Dev. Brain Res. (1997) 101(1-2):139-147.
Kranenburg, O. et al., "beta-Amyloid (Abeta) cuases detachment of N1E-115 neuroblastoma cells by acting as a scaffold for cell-associated plasminogen activity," Mol. Cell. Neurosci. (2005) 28(3):496-508.
Kriegler, M., Gene Transfer and Expression—A Laboratory Manual (1990) Table of Contents.
Kumar et al., "Molecular cloning and expression of the Fabs of human autoantibodies in *Escherichia coli*," J. Biol. Chem. (2000) 275:35129-35136.
Kumar, a. et al., "Neuropathology and therapeutic management of Alzheimer's disease—an update," Drugs of the Future (2008) 33(5):433-446.
Kumar-Singh, S. et al., "Dense-core senile plaques in the Flemish variant of Alzheimer's disease are vasocentric," Am. J. Pathol. (2002) 161(2):507-520.
Kuo, Y-M. et al., "Water-soluble Abeta (N-40, N-42) oligomers in normal and Alzheimer disease brains," J. Biol. Chem. (1996) 271(8):4077-4081.
Kwon, Y.E. et al., "Synthesis, in vitro assay, and molecular modeling of new piperidine derivatives having dual inhibitory potency against acetylcholinesterase and Abeta Sub 1-42 aggregation for Alzheimer's disease therapeutics," Bioorg. Med. Chem. (2007) 15(20):6596-6607.
Lacor et al., "Synaptic targeting by Alzheimer's-related amyloid beta oligomers," J. Neurosci. (2004) 24:1019110200.
Laemmli, U.K. et al., "Cleavage of structural proteins during the assembly of the head of bacteriophage T4," Nature (1970) 227:680-685.
Lahiri, D.K. et al., "Lethal weapon: amyloid beta-peptide, role in the oxidative stress and neurodegeneration of Alzheimer's disease," Neurobiol Aging (2004) 25(5):581-587.
Lam, A.R. et al., "Effects of the Arctic (E22-G) mutation on amyloid beta-protein folding: discrete molecular dynamics study," J. Amer. Chem. Soc. (2008) 130(51):17413-22.
Lam, X.M. et al., "Microencapsulation of recombinant humanized monoclonal antibody for local delivery," Proceedings Intl. Symp. Control. Rel. Bioact. Mater. (1997) 24:759-760.
Lambert, M.P. et al., "Diffusible, nonfibrillar ligands derived from a Betal -42 are potent central nervous system neurotoxins," Proc. Natl. Acad. Sci. (1998) 95:6448-6453.
Lambert, M.P. et al., "Monoclonal antibodies that target pathological assemblies of a beta," J. Neurochem. (2007) 100(1):23-35.
Langer & Peppas, Editors, Journal of Macromolec. Sci. (1983) 23:61-127.
Langer, R., New methods of drug delivery, Science (1990) 249:1527-1533.
Lanni, C. et al., "Studies and screening of molecules interacting with beta amyloid and other amyloidogenic proteins," Society for Neuroscience Abstract Viewer and Itinerary Planner (2003) Abstract No. 841.1, 33rd Annual Meeting of the Society of Neuroscience, New Orleans, LA, Nov. 8-12, 2003.
Lashuel, H.A. et al., "Amyloid pores from pathogenic mutations," Nature (2002) 418(6895):291.
Lau, T-L. et al., "Cholesterol and clioquinol modulation of a beta(1-42) interaction with phospholipid bilayers and metals," Biochimica et biophysica acta 82007) 1768(12):3135-44.
Lauren, J. et al., "Cellular prion protein mediates impairment of synaptic plasticity by amyloid-beta oligomers," Nature (2009) 457(7233):1128-1132.
Lazo, N. D. et al., "On the nucleation of amyloid beta-protein monomer folding," Protein Sci. (2005) 14(6):158115196.
Leader, K.A. et al., "Antibody responses to the blood group antigen D in SCID mice reconstituted with human blood mononuclear cells," Immunology (1992) 76:229-234.
Lecanu, L. et al., "Caprospinol: moving from a neuroactive steroid to a neurotropic drug," Exp. Opin. Invest. Drugs (2009) 18(3):265-276.
Lee, C-C. et al., "Insulin rescues amyloid beta-induced impairment of hippocampal long-term potentiation," Neurobiol. Aging (2009) 30(3):377-387.
Lee, D.H.S., et al., "Differential physiologic responses of alpha7 nicotinic acetylcholine receptors to beta-amyloid Sub 1-40 and beta-amyloid SUB 10-42," J. Neurobiol. (2003) 55(1):25-30.
Lee, E.B. et al., "Secretion and intracellular generation of truncated Abeta in beta-site amyloid-beta precursor protein-cleaving enzyme expressing human neurons," J. Biol Chem. (2003) 278(7):4458-4466.
Lee, E.B. et al., "Targeting amyloid-beta peptide (Abeta) oligomers by passive immunization with a conformation-selective monoclonal antibody improves learning and memory in Abeta precursor protein (APP) transgenic mice," J. Biol. Chem. (2006) 281(7):4292-4299.
Lee, H-K. et al., "The insulin/Akt signaling pathway is targeted by intracellular beta-amyloid," Mol. Biol. Cell (2009) 20(5):1533-1544.
Lee, T.Y. et al., "Artificial proteases toward catalytic drugs for amyloid diseases," Pure and Applied Chem. (2009) 81:255-262.
Lemere, C.A. et al., "Amyloid-beta immunotherapy for the prevention and treatment of Alzheimer disease: lessons from mice, monkeys, and humans," Rejuvenation Res. (2006) 9(1):77-84.
Lemere, C.A. et al., "Developing novel immunogens for a safe and effective Alzheimer's disease vaccineNeurotherapy: Progress in Restorative Neuroscience and Neurology," Progress in Brain Research (2009) 175:83-93.
Lerner, E.A., "How to make a hybridoma," The Yale Journal of Biology and Medicine (1981) 54(5):387-402.
Leveille, F. et al., "Influence des formes oligomeriques du peptide amyloide beta 1-42 sur la viabilite neuronale," Revue Neurologique (2007) 163(11)-2:4S23.
LeVINE, H. et al., "Alzheimer's .beta.-peptide oligomer formation at physiologic concentrations," Anal. Biochem. (2004) 335:81-90.
Levitt, M., "Molecular dynamics of native protein," J. Mol. Biol. (1983) 168:595-620.

(56) References Cited

OTHER PUBLICATIONS

Levy et al , "Inhibition of calcification of bioprosthetic heart valves by local controlled-release diphosphonate," Science (1985) 228:190-192.
Lewis, H. et al., "Quantification of Alzheimer pathology in ageing and dementia: age-related accumulation of amyloid-beta(42) peptide in vascular dementia," Neuropath. Appl. Neurobiol. (2006) 32(2):103-118.
Li, H. et al., "SAR and mechanistic studies of tetrapeptide inhibitors of a beta 42-induced neurotoxicity," Biopolymers (2009) 92(4):P077.
Liao, Y.J. et al., "Anti-Ca2+ channel antibody attenuates Ca2+ currents and mimics cerebellar ataxia in vio," Proc. Natl. Acad. Sci. USA (2008) 105(7):2705-2710.
Liirs, T. et al., "3D structure of Alzheimer's amyloid-beta (1-42) fibrils," Proc. Natl. Acad. Sci. (2005) 102(48): 17342-17347.
Lindberg, C. et al., "beta-amyloid protein structure determines the nature of cytokine release from rat microglia," J. Mol. Neurosci. (2005) 271-12.
Little, M. et al., "Of mice and men: hybridoma and recombinant antibodies," Immun Today (2000) 21(8):364370.
Liu, M. et al., "Progress in soluble Abeta oligomers in Alzheimer's disease and drugs targeting Abeta oligomers," Chinese Pharmacological Bulletin (2008) 24(12):1554-1557.
Liu, Q. et al., "A novel nicotinic acetylcholine receptor subtype in basal forebrain cholinergic neurons with high sensitivity to amyloid peptides," J. Neurosci. (2009) 29(4):918-929.
Liu, R. et al., "Residues 17-20 and 35-35 of beta-amyloid play critical roles in aggregation," J. Neurosci Res. (2004) 75(2):162-171.
Liu, R. et al., "Trehalose differentially inhibits aggregation and neurotoxicity of beta-amyloid 40 and 42," Neurobiol. Dis. (2005) 20(1):74-81.
Lonberg, N. et al., "Antigen-specific human antibodies from mice comprising four distinct genetic modifications," Nature (1994) 368:856-859.
Lonberg, N. et al., "Human antibodies from transgenic mice," Intern. Rev. Immunol. (1995) 13:65-92.
Lue, L-F et al., "Soluble amyloid beta peptide concentration as a predictor of synaptic change in Alzheimer's disease," Am. J. Path. (1999) 155(3):853-862.
Lunn, M.P.T. et al., "High-affinity anti-ganglioside IgG antibodies raised in complex ganglioside knockout mice: reexamination of FDIa immunolocalization," J. Neurochem. (2000) 75:404-412.
Ma, Q.L. et al., "p21-activated kinase-aberrant activation and translocation in Alzheimer's disease pathogenesis," J. Biol. Chem. (2008) 283(20):14132-14143.
Macao, B. et al., "Recombinant amyloid beta-peptide production by coexpression with an affibody ligand," BMC Biotechnology (2008) 8:82.
MacCallum, R. M. et al., "Antibody-antigen interactions: contact analysis and binding site topography," J. Mol. Biol. (1996) 262:732-745.
Maccioni, R.B. et al., "What have we learned from the tau hypothesis? Current hypothesis and research milestones in Alzheimer's disease current hypotheses and research milestones in Alzheimer's disease," International Summitt Meeting on Current Hypotheses on Alzheimer Disease, Renaca, Chile, Nov. 22-25, 2007.
Macquitty, J.M. et al., "GenPharm's knockout mice," Science (1992) 257:1188.
Mader, C. et al., "Interaction of the crystalline bacterial cell surface layer protein SbsB and the secondary cell wall polymer of geobacillus stearothermophilus PV72 assessed by real-time surface plasmon resonance biosensor technology," J. Bacteriol. (2004).
Madrigal, J.L.M. et al., "Neuroprotective actions of noradrenaline: effects of glutathione synthesis and activation of peroxisome proliferator activated receptor delta," J. Neurochem. (2007) 103(5):2092-101.
Maier, M. et al., "Short amyloid-beta immunogens reduce cerebral in an Alzheimer's disease mouse model in the absence of an Amyloid-beta-specific cellular immune response," J. Neurosci. (2006) 26(18):4717-4728.
Maliga, P. et al., Methods in Plant Molecular Biology—a Laboratory Manual, Table of Contents (1995).
Mandal, P.K. et al., "Alzheimer's disease: halothane induces Abeta peptide to oligomeric form —solution NMR studies," Neurochem. Res. (2006) 31(7):883-890.
Manelli, A.M. et al., "A beta 42 neurotoxicity in primary co-cultures: effect of apoE isoform and a beta conformation," Neurobiol. Of Aging V007) 281139-1147.
Manelli, A.M. et al., "ApoE and Abetal-42 interactions," J. Mol. Neurosci. (2004) 23235-246.
Manelli, A.M. et al., "Glial activation by oligomeric versus fibrillar Abetal-42," Soc. For Neurosci. Abstract Viewer and Itinerary Planner (2002), Abstract No. 193.9, 32nd Annual meeting of the Society for Neuroscience, Orlando, FL, Nov. 2-7, 2002.
Marachalonis, J.J. et al., "Evolutionary factors in the emergence of the combinatorial germline antibody repertoire," Adv. Exp. Med. Biol. (2001) 484:13-30.
Maria, T.J. et al., "Upregulation of p21(Cipl) in activated glial cells," Glia (2009) 57524-534.
Mariette, X., "Nucleotidic sequence analysis of the variable domains of four human monoclonal IgM with an antibody activity to myelin-associated glycoprotein," Eur. J. Immunol. (1993) 23:846-851.
Marlow, L. et al., "APH1, PEN2 and Nicastrin increase Abeta levels and gamma-secretase activity," Biochem. Biophys. Res. Comm (2005) 305(3):502-509.
Masliah, E. et al., "Progress in the development of new treatments for combined Alzheimer's and Parkinson's diseases," Drug Development Res. (2002) 56282-292.
Masman, Mf. Et al., "In silico study of full-length amyloid beta 1-42 tri- and penta-oligomers in solution," J. Phys. Chem. B. (2009) 113:11710-11719.
Masters, C.L. et al., "Amyloid plaque core portein in Alzheimer disease and Down syndrome," Proc. Natl. Acad. Sci. Usa (1985) 82:4245-4249.
Mastrangelo, I.A. et al., "High-resolution atomic force microscopy of soluble a.beta.42 oligomers," J. Mol. Biol. (2006) 358:106-119.
Masuda, Y. et al., "Identification of physiological and toxic conformations in Abeta42 aggregates," Chem Bio Chem. (2009) 10(2):287-295.
Mathura, V.S. et al., "Model of Alzheimer's disease amyloid-beta peptide based on a Rna binding protien," Biochem. Biophys. Res. Comm (2005) 332(2):585-592.
Mattson et al., "A practical approach to crosslinking," Mol. Biol. Reports (1993) 17:167-183.
Mattson, M.P., "Pathways towards and away from Alzheimer's disease," Nature (2004) 430:631-639.
Mattson, M.P., "Pathways towards and away from Alzheimer's disease," Nature (2004) 431(7004):107.
Maurer, M.H. et al., "The proteome of neural stem cells from adult rat hippocampus," Proteome Sci. (2003) 1(1):4.
May, K., "Buying a new immnoassay system?" BioTechnology-Tibtech (1993) 11:272-273.
Mccafferty, J. et al., "Phage antibodies: filamentous phage displaying antibody variable domains," Nature (1990) 348:552-554.
Mclaurin, J. et al., "Inositol steroisomers stabilize an oligomeric aggregate of Alzheimer amyloid beta peptide and inhibit Abeta-induced toxicity," J. Biol. Chem. (2000) 27518495-18502.
Mclaurin, J. et al., "Review modulating factors in amyloid-beta fibril formation," J. Structural Biol. (2000) 130(2-3):259-270.
Mclean, C.A. et al., "Soluble pool of Abeta amyloid as a determinant of severity of neurodegeneration in Alzheimer's disease," Am. Neurol. Assoc. (1999) 46:860-866.
Meijer et al., "Biochemical and cellular effects of roscovitine, a potent and selective inhibitor of the cyclindependent kinases cdc2, cdk2 and cdk5," Eur. J. Biochem. (1997) 243(1-2):527-536.
Meli, G. et al., "Direct in vivo intracellular selection of conformation-sensitive antibody domains targeting Alzheimer's amyloid-beta oligomers," J. Mol. Biol. (2009) 287(3):584-606.
Mendez, M.J. et al., "Functional transplant of megabase human immunoglobulin loci recapitulates human antibody response in mice," Nat. Genet. (1997) 15(2):146-156.
Merrifield, B., "Solid phase synthesis," Science (1986) 232:342.

(56) References Cited

OTHER PUBLICATIONS

Merrifield, J., "The total synthesis of an enzyme with ribonuclease a activity," J. Am. Chem. Soc. (1969) 91:501-502.
Miller, Y. et al., "Polymorphism of Alzheimer's a beta(17-42) (p3) oligomers: the importance of the turn location and its conformation," Biophys. J. (2009) 971168-1177.
Minkeviciene, R. et al., "Amyloid beta-induced neuronal hyperexcitability triggers progressive epilepsy," J. Neurosci. (2009) 29(11):3453-3462.
Mizushima, S. et al., "pEF-BOX, a powerful mammalian expression vector," Nucl. Acids Res. (1990) 18(17):5322.
Moechars et al., "Early phenotypic changes in transgenic mice that overexpress different mutants of amyloid precursor protein in brain," J. Biol. Chem. (1999) 274(10):6483-6492.
Moir et al., "Autoantibodies to redox-modified oligomeric Abeta are attenuated in the plasma of Alzheimer's disease patients," J. Biol. Chem. (2005) 280:17458-17463.
Monien, B.H. et al., "A novel approach to Alzheimer's disease therapy: inhibition of A beta 42 oligomerization by C-terminal a beta 42 fragments," J. Peptide Sci. (2006) 12147.
Morgan, R.A. et al., "Human gene therapy," Ann. Rev. Biochem. (1993) 62:191-217.
Morgan, T.E. et al., "Abeta-derived diffusible ligands (ADDLs): Clusterin (apo J), congo red binding and toxicity," Society for Neuroscience Abstracts (1999) Abstract No. 252130, 29th Annual Meeting of the Society for Neuroscience, Miami Beach, FL, Oct. 23-28, 1999.
Morley, J.S., "Modulation of the action of regulatory peptides by structural modification," TIPS (1980) 463-468.
Morrison, S.L. et al., "Chimeric human antibody molecules: mouse antigen-binding domains with human constant region domains," Proc. Natl. Acad. Sci. (1984) 81:6851-6855.
Morrison, S.L., "Transfectomas provide novel chimeric antibodies," Science (1986) 229:1202-1207.
Mueller, W. et al., "Apolipoprotein E isoforms increase intracellular Ca2+ differentially through an omegaagatoxin IVA-sensitive Ca2+ channel," Brain Pathology (1998) 8(4):641-653.
Mullan et al., "A locus for familial early-onset Alzheimer's disease on the long arm of chromosome 14, proximal to the alphal-amtichymotrypain gene," Nature Genet. (1992) 2:340-342.
Mullan, M. et al., "A pathogenic mutation for probable Alzheimer's disease in the APP gene at the N-terminus of beta-amyloid," Nat. Genet. (1992) 1(5):345-347.
Muller, W. et al., "Impaired Ca-signling in astrocytes from the Ts16 mouse model of Down syndrome," Neurosci. Lett. (1997) 223(2):81-84.
Mulligan, R.C., "The basic science of gene therapy," Science (1993) 260:926-932.
Mullis, K. et al., "Specific enzymatic amplification of DNA in vitro: the polymerase chain reaction," Cold Spring Harbor Symp. Quant. Biol. (1986) 51:263-273.
Munter, L-M. et al., "GxxxG motifs within the amyloid precursor protein transmembrane sequence are critical for the etiology of Abeta42," EMBO J. (2007) 26(6):1702-1712.
Murphy, W.J. et al., "CD40 stimulation promotes human dsecondary immunoglobulin responses in HuPBL-SCID chimeras," Clin. Immunol. (1999) 90(1):22-27.
Murphy, W.J. et al., "The huPBL-SCID mouse as a means to examine human immune functionin vivo," Immunol. (1996) 8:233-241.
Murray, M.M. et al, "Amyloid beta protein: a beta 40 inhibits a beta 42 oligomerization," J. Am. Chem. Soc. (2009) 131:6316-6317.
Myagkova, M.A. et al., "Autoantibodies to beta-amyloid and neurotransmitters in patients with Alzheimer's disease and senile dementia of the Alzheimer type," Bulletin of Exp. Biol. Med. (2001) 2:127-129.
Nagele, R.G. et al., "Contribution of glial cells to the development of amyloid plaques in Alzheimer's disease," Neurobiol of Aging (2004) 25(5):663-674.

Naslund, J. et al., "Relative abundance of Alzheimer Abeta amyloid peptide variants in Alzheimer disease and normal aging," Proc. Natl. Acad. Sci. (1994) 91:8378-8382.
Nath et al., "Autoantibodies to amyloid B-peptide (AB) are increased in Alzheimer's disease patients and AB antibodies can enhance AB neurotoxicity," Neuromol. Med. (2003) 3:29-39.
Needleman, S.B. et al., "A general method applicable to the search for similarities in the amino acid sequence of two proteins," J. Mol. Biol. (1970) 48:443-453.
Nerelius, C. et al., "Alpha-Helix targeting reduces amyloid-beta peptide toxicity," Proc. Natl. Acad. Sci. USA (2009) 106(23):9191-9196.
Neuberger, M.S. et al., "Recombinant antibodies possessing novel effector functions," Nature (1984) 312:604608.
Nguyen, H. et al., "Production of human monoclonal antibodies in SCID mouse," Microbiol. Immunol. (1997) 41(12):901-907.
Nicholas, M.R. et al., "Different amyloid-ent amyloid-beta aggregation states induced monocyte differentiation or activation," J. Neurochem. (2009) 10867, 40th Annual Meeting of the American Society for Neurochemistry, Charleston, South Carolina, Mar. 7-11, 2009.
Nielsen, H.M. et al., "Preferential uptake of amyloid beta 1-42 oligomers by primary human astrocytes in vitro: influence of SAP and C1q," Mol. Immunol. (2009) 262860, 12th European Meeting on Complement in Human Disease, Hungary, Sep. 5-8, 2009.
Nilges, M. et al., "Determination of three-dimensional structures of proteins from interproton distance data by hybrid distance geometry-dynamical simulated annealing calculations," FEBS Lett. (1989) 229(2):317-324.
Nimmrich, V. et al., "Amyloid beta oligomers (A beta(1-42) globulomer) suppress spontaneous synaptic activity by inhibition of P/Q-type calcium currents," J. Neurosci. (2008) 28(4):788-797.
Nimmrich, V. et al., "Is Alzheimer's disease a result of presynaptic failure? - Synaptic dysfunctions induced by oligomeric p-amyloid," Rev. Neurosci. (2009) 20(1):1-12.
Ntng, S. et al., "Intratumoral radioimmunotherapy of a human colon cancer xenograft using a sustained-release gel," Radiotherapy & Oncology (1996) 39:179-189.
Nomura, I. et al., "Mechanism of impairment of long-term potentiation by amyloid beta is independent of Nmda receptors or voltage-dependent calcium channels in hippocampal CA1 pyramidal neurons," Neurosci. Lett. (2005) 391(1-2):1-6.
Oi, V.T. et al., "Chimeric antibodies," BioTechniques (1985) 4(3):214-215.
Okamuro et al., The Biochemistry of Plants—A comprehensive Treatise, V. 15, 1-82 (1989).
Ono, K. et al., "Effects of grape seed-derived polyphenols on amyloid beta-protein self-assembly and cytotoxicity," J. Biol. Chem. (2008) 283(47):32176-32187.
Opazo, C. et al., "Metalloenzyme-like activity of Alzheimer's disease beta-amyloid: Cu-dependent catalytic conversion of dopamine, cholesterol, and biological reducing agents to neurotoxic H SUB 2O SUB 2," J. Biol. Chem. (2002) 277(43):40302-40308.
Orgogozo et al., "Subacute meningoencephalitis in a subset of patients with AD after Abeta42 immunization," Neurology (2003) 61:46-54.
Origlia, N. et al., "Abeta-dependent inhibition of LTP in different intracortical circuits of the visual cortex: the role of RAGE," J. Alzheimer's Disease (2009) 17(1):59-68.
Otto, M. et al., "Neurochemical approaches of cerebrospinal fluid diagnostics in neurogenerative diseases," Methods (2008) 44(4):289-298.
Padlan et al., "Structure of an antibody-antigen complex: crystal structure of the HyHEL-10 Fab-lysozyme complex," Proc. Natl. Acad. Sci USA (1989) 86:5938-5942.
Padlan, E.A. et al., "Identification of specificity-determining residues in antibodies," FASEB (1995) 9:133-139.
Padlan, E.A., "A possible procedure for recucing the immunogenicity of antibody variable domains while preserving their ligand-binding properties," Molec. Immunol. (1991) 28(4/5):489-498.
Palmer, J. et al., "Endothelin-converting enzyme-2 is increased in Alzheimer's disease and up-regulated by Abeta," Am. J. Path. (2009) 175(1):262-270.

(56) References Cited

OTHER PUBLICATIONS

Pan, X.D. et al., "Tripchlorolide protects neuronal cells from microglia-mediated beta-amyloid neurotoxicity through inhibiting NF-kappa B and Jnk signaling," GLIA (2009) 57:1227-1238.

Pan, X-D. et al., "Effect of inflammatory responses in microglia induced by oligomeric beta-amyloid SUB 1-42 on neuronal cells," Acta Anatomica Sinica (2008) 39(6):804-809.

Partis, M.D. et al., "Crosslinking of proteins by omega-maleimido alkanoyl N-hydroxysuccinimide esters," J. Protein Chem. (1983) 2:263-277.

Pastor, M.T. et al., "Amyloid toxicity is independent of polypeptide sequence, length and chirality," J. Mol. Biol. (2008) 375:695-707.

Paul, W.E., editor, Fundamental Immunology, Third Edition, Raven Press, New York (1993) 292-295.

Peacock, M.L. et al., "Novel amyloid precursor protein gene mutation (codon 665Asp) in a patient with late-onset Alzheimer's disease," Ann. Neurol. (1994) 35(4):432-438.

Peacock, M.L. et al., "Novel polymorphism in the A4 region of the amyloid precursor protein gene in a patient without Alzheimer's disease," Neurol. (1993) 43(6):1254-1256.

Pearson, W.R. et al., "Improved tools for biological sequence comparison," PNAS (1988) 85:2444-2448.

Pellicano, M. et al., "The sea urchin embryo: a mdoel to study Alzheimer's beta amyloid induced toxicity," Archives of Biochem. Biophys. (2009) 483:120-126.

Perouansky, M., "Liaisons dangereuses? General anaesthetics and long-term toxicity in the CNS," Eur. J. Anaesthesiol. (2007) 24(2):107-115.

Persic, L. et al., "An integrated vector system for the eukaryotic expression of antibodies or their fragments after selection from phage display libraries," Gene (1997) 187:9-18.

Petrushina, I., "Alzheimer's disease peptide epitope vaccine reduces insoluble but not soluble/oligomeric Abeta species in amyloid precursor protein transgenic mice," J. Neurosci. (2007) 27(46):12721-12731.

Pfeifer, M. et al., "Cerebral hemorrhage after passitve anti-Abeta immunotherapy," Science (2002) 298:1379.

Phu, M-J et al., "Fluorescence resonance energy transfer analysis of apolipoprotein e C-terminal domain and amyloid beta peptide (1-42) interaction," J. Neurosci. Res. (2005) 80(6):877-886.

Pike, C.J. et al., "Structure—activity analyses of B-amyloid peptides: contributions of the B25-35 region to aggregation and neurotoxicity," J. Neurochem. (1995) 64(1):253-265.

Plant, LD. Et al., "The production of amyloid beta peptide is a critical requirement for the viablility of central neurons," J. Neurosci. (2003) 23(13):5531-5535.

Podlisny, M.B. et al., "Aggreagation of secreted amyloid beta-protein into sodium dodecyl sufate-stable oligomers in cell culture," J. Biol. Chem. (1995) 270(16):9564-9570.

Poljak, R.J., "Production and structure of diabodies," Structure (1994) 2:1121-1123.

Portelius, E. et al., "Targeted proteomics in Alzheimer's disease: focus on amyloid-beta," Exp. Rev. Proteomics (2008) 5(2):225-237.

Portolano, S. et al., "High affinity, thyroid-specific human autoantibodies displayed on the surface of filamentous phage use V genes similar to other autoantibodies," J. Immunol. (1993) 151(5):L2839-2851.

Presta, LG. et al., "Humanization of an antibody directed against IgE," J. Immunol. (1993) 151(5):2623-2632.

Putney, P.W., Calcium Signaling, CRC Press Inc. (2005).

Puzzo, D. et al., "Picomolar amyloid-beta positively modulates synaptic plasticity and memory in hippocampus," J. Neurosci. (2008) 28:14537-14545.

Qian, J. et al., "Presynaptic Ca2+ channels and neurotransmitter release at the terminal of a mouse cortical neuron," J. Neurosci. (2001) 21(11):3721-3728.

Qiu, W. et al., "Convenient, large-scale asymmetric synthesis of eriantiomerically pure trans-cinnamylglycine and—alpha-alamine," Tetrahedron (2000) 56:2577-2582.

Qiu, W.Q. et al., "Degradation of amyloid beta-protein by a metalloprotease secreted by microglia and other neural and non-neural cells," J. Biol. Chem. (1997) 272(10):6641-6646.

Qiu, W.Q. et al., "Insulin-degrading enzyme regulates extracellular levels of amyloid beta-protein by degradation," J. Biol. Chem. (1998) 273(49):32730-32738.

Quinn, J.F. et al., "Copper complexing with tetrathiomolybdate suppresses amyloid pathology in a transgenic mouse model of Alzheimer's disease," Neurology (2009) 72A52-A53.

Racke, M.M. et al., "Exacerbation of cerebral amyloid angiopathy-associated microhemmorrhage in amyloid precursor protein transgenic mice by immunotherapy is dependent on antibody recognition of deposited forms of amyloid beta," J. Neurosci. (2005) 25(3):629-636.

Rahimi, F. et al., "Photo-induced cross-linking of unmodified proteins (PICUP) applied to amyloidogenic peptides," J. Visualized Exp. (2009) 23.

Rahimi, F. et al., "Structure-function relationships of pre-fibrillar protein assemblies in Alzheimer's disease and related disorders," Curr. Alzheimer Res. (2008) 5(3):319-341.

Rambaldi, D.C. et al., "In vitro amyloid a beta(1-42) peptide aggregation monitoring by asymmetrical flow field-flow fractionation with multi-angle light scattering detection," Anal. Bioanal. Chem. (2009) 394:2145-2149.

Rangachari, V. et al., "Amyloid beta(1-42) rapidly forms protofibrils and oligomers by distinct pathways in low concentrations of sodium dodecylsulfatet," Biochem. (2007) 46:12451-12462.

Rangachari, V. et al., "Rationally designed dehydroalanine (Delta Ala)-containing peptides inhibit amyloid-beta (A beta) peptide aggregation," Biopolymers (2009) 91:456-465.

Rangachari, V. et al., "Secondary structure and interfacial aggregation of Amyloid beta(1-40) on sodium dodecyl sulfate micelles," Biochem. (2006) 45:8639-8648.

Ravault, S. et al., "Fusogenic Alzheimer's peptide fragment Abeta (29-42) in interaction with lipid bilayers: secondary structure, dynamics, and specific interaction with phosphatidyl ethanolamine polar heads as revealed by solid-state NMR," Protein Sci. (2005) 14(5):1181-1189.

Ravetch, J.V. et al., "Structure of the human immunoglobulin p, locus: characterization of embryonic and rearranged J and D genes," Cell (1981) 27:583-591.

Reisner, Y. et al., "The trimera mouse: generating human monoclonal antibodies and an animal model for human diseases," Trends in Biotech. (1998) 16:242-246.

Remington: The Science and Practice of Pharmacy, Mack Publishing (1995) 19th Edition: Table of Contents.

Resende, R. et al., "ER stress is involved in Abeta-induced GSK-3 beta activation and tau phosphorylation," J. Neurosci. Res. (2008) 86(9):2091-2099.

Resende, R. et al., "Neurotoxic effect of oligomeric and fibrillar species of amyloid-beta peptide 1-42: involvement of endoplasmic reticulum calcium release in oligomer-induced cell death," Neurosci. (2008) 155(3):725-737.

Riechman, L. et al., "Reshaping human antibodies for therapy," Nature (1988) 332:323-327.

Robert, R. et al., "Engineered antibody intervention strategies for Alzheimer's disease and related dementias by targeting amyloid and toxic oligomers," Protein Engineering, Design and Selection (2009) 22(3):199-208.

Roberts, R.W. et al., "Rna-peptide fusions for the in vitro selection of peptides and proteins," Proc. Natl. Acad. Sci. USA (1997) 94:12297-12302.

Robinson, J.R. et al., Sustained and Controlled Release Drug Delivery Systems, (1978) Table of Contents.

Roes, J. et al., "Mouse anti-mouse IgD monoclonal antibodies generated in IgD-deficient mice," J. Immunol. Meth. (1995) 183:231-237.

Roguska, M.A. et al., "Humanization of murine monclonal antibodies through variable domain resurfacing," Proc. Natl. Acad. Sci. (1994) 91:969-973.

Roher, A.A. et al., "Oligomerization and fibril assembly of the amyloid-beta protein," Biochimica et Biophysica Acta (2000) 1502(1):31-43.

(56) References Cited

OTHER PUBLICATIONS

Roher, A.E. et al., "Morphology and toxicity of Abeta-(1-42) dimer derived from neuritic and vascular amyloid deposits of Alzheimer's disease," J. Biol. Chem. (1996) 271(34):20631-20635.

Ronicke, R. et al., Abeta mediated diminution of MTT reduction—an artefact or single cell culture? PLoS ONE (2008) 3(9) e3236.

Rossi, G. et al., "A family with Alzheimer disease and strokes associated with A713T mutation of the APP gene," Neurology (2004) 63(5):910-912.

Rouillard, J-M et al., "Gene2Oligo: oligonucleotide design for in vitro gene synthesis," Nucl. Acids. Res. (2004) 32:W176-180.

Rudikoff et al., "Single amino acid substitution altering antigen-binding specificity," Proc. Natl. Acad. Sci. USA (1982) 79(6):1979-1983.

Russo, C. et al., "Presenilin-1 mutatiosn in Alzheimer's disease," Nature (2000) 405:531-532.

Sabella, S. et al., "Capillary electrophoresis studies on the aggregation process of beta-amyloid 1-42 and 1-40 peptides," Electrophoresis (2004) 25:3186-3194.

Saido, T.C. et al., "Dominant and differential deposition of distinct beta-amyloid peptide species, AbetaN3 in senile plaques," Neuron (1995) 14:457-486.

Salomon, A.R. et al., "Nicotine inhibits amyloid formation by the beta-peptide," Biochem. (1996) 35(42):1356878.

Sambamurti, K. et al., "A partial failure of membrane protein turnover may cause Alzheimer's disease: a new hypothesis," Curr. Alzheimer Res. (2006) 3:81-90.

Sambrook, J. et al., Molecular Cloning—a Laboratory Manual, 2nd Edition (1989) Table of Contents 17.2-17.9.

Samoszuk, M.K. et al., "A peroxide-generating immunoconjugate directed to eosinophil peroxidase is cytotoxic to Hodgkin's disease cells in vitro," Antibody, Immunoconjugates and Radiopharmaceuticals (1989) 2:37-45.

Sandberg, a. et al., "Stabilization of neurotoxic Alzheimer amyloid-beta oligomers by protein engineering," Proc. Natl. Acad. Sci. (2010) 107(35):15595-15600.

Sankaranarayanan, S., "Genetically modified mice models for Alzheimer's disease," Curr. Top. Med. Chem. (2006) 6(6):609-627.

Santos, a.N. et al., "A method for the detection of amyloid-beta Sub 1-40, amyloid-beta Sub 1-42 and amyloid-beta oligomers in blood using magnetic beads in combination with flow cytometry and its application in the diagnostics of Alzheimer's disease," J. Alzheimer's Dis. (2008) 14(2):127-131.

Sanz-Blasco, S. et al., "Mitochondrial Ca2+ overload underlies a beta oligomers neurotoxicity providing an unexpected mechanism of neuroprotection by NSAIDs," PloS One (2008) 3 Article No. e2718.

Sato, J. et al., "Design of peptides that form amyloid-like fibrils capturing amyloid beta 1-42 peptides," Chemistry A Eur. J. (2007) 13:7745-7752.

Sato, N. et al., "Development of new screening system for Alzheimer disease, in vitro Abeta sink assay, to identify the dissocation of soluble Abeta from fibrils," Neurobiol. Dis. (2006) 22(3):487-495.

Saudek, C.D. et al., "A preliminary trail of the programmable implantable medication system for insulin delivery," New Engl. J. Med. (1989) 321(9):574-579.

Sawai, H. et al., "Direct production of the fab fragment derived from the sperm immobilizing antibody using polymerase chain reaction and cDNA expression vectors," Amer. J. Reproduc. Immunol. (1995) 34:26-34.

Schafmeister et al., "An all-hydrocarbon cross-linking system for enhancing the helicity and metabolilc stability of peptides," J. Am. Chem. Soc. (2000) 122:5891-5892.

Schenk et al., "Current progress in beta-amyloid immunotherapy," Curr. Opin. Immun (2004) 16:599-606.

Schenk, D., "Amyloid-beta immunotherapy for Alzheimer's disease: the end of the beginning," Nature (2002) 3:824-828.

Schilling, S. et al., "On the seeding and oligomerization of pGlu-amyloid peptides (in vitro)," Biochem. (2006) 45(41):12393-12399.

Scholtzova, H. et al., "Induction fo toll-like receptor 9 signaling as a method for ameliorating Alzheimer's disease-related pathology," J. Neurosci. (2009) 291846-1854.

Schott, J.M. et al., "New developments in mild cognitive impairment and Alzheimer's disease," Curr. Opin. Neurol. (2006) 19(6):552-558.

Schuck, P., "Size distribution analysis of macromolecules by sedimentation velocity ultracentrifugation and Lamm equation modeling," Biophys. J. (2000) 78:1606-1619.

Sciaretta et al., "Abeta40-Lactam (D23/K28) models a conformation highly favorable for nucleation of amyloid," Biochem. (2005) 44:6003-6014.

Sefton, M.V., "Implantable pumps," Critical Reviews in Biomedical Engineering (1987) 14(3):201-240.

Selenica, M.L. et al., "Cystatin C reduces the in vitro formation of soluble Abetal-42 oligomers and protofibrils," Scan. J. Clin. Lab. Invest. (2007) 67(2):179-190.

Selkoe, D.J., "Alzheimer's disease: genes, proteins and therapy," Physiol. Reviews, American Physiological Society (2001) 81(2):741-766.

Selkoe, D.J., Clearing the brain's amyloid cobwebs, Neuron (2001) 32:177-180.

Sergeant, N. et al., "Truncated beta-amyloid peptide species in pre-clinical Alzheimer's disease as new targets for the vaccination approach," J. Neurochem. (2003) 85:1581-1591.

Shapiro, .S. et al., "DNA target motifs of somatic mutagenesis in antibody genes," Crit. Rev. in Immunol. (2002) 22(3): 183-200.

Shields, R.L. et al., "Lack of fucose on human IgG1 N-linked oligosaccharide improves binding to human FcyRIII and antibody-dependent cellular toxiciy," J. Biol. Chem. (2002) 277(30):26733-26740.

Shimizu, E. et al., "IL-4-induced selective clearance of oligomeric beta-amyloid peptide(1-42) by rat primary type 2 microglia," J. Immun (2008) 181(9):6503-6513.

Shu, L. et al., "Secretion of a single-gene-encoded immunoglobulin from myeloma cells," Proc. Natl. Acad. Sci.(1993) 90:7995-7999.

Shughrue et al., "Anti=ADDL antibodies differentially block oligomer binding to hippocampal neurons," Neurobiol. Aging (2010) 31:189-202.

Sikorski, P. et al., "Structure and texture of fibrous crystals formed by Alzheimer's abeta(11-25) peptide fragment," Structure (London) (2003) 11(8):915-926.

Sims, M.J. et al., "A humanized CD18 antibody can block function without cell destruction," J. Immunol. (1993) 151(4):2296-2308.

Sinz, A., "Chemical cross-linking and mass spectrometry for mapping three-dimensional structures of proteins and protein complexes," J. Mass Spectrom. (2003) 38:1225-1237.

Sjogren, M. et al., "Cholesterol and Alzheimer's disease—is there a relation?," Mechanisms of Aging and Development (2006) 127:138-147.

Sjogren, M. et al., "The link between cholesterol and Alzheimer's disease," World J. Biol. Psych. (2005) 6(2):8597.

Skerra, A. et al., "Assembly of a functional immunoglobulin F fragment in *Escherichia coli*," Science (1988) 240:1038-1040.

Smith, D.P. et al., "Concentration dependent Cu SUP 2+ induced aggregation and dityrosine formation of the Alzheimer's disease amyloid-betapeptide," Biochem. (2007) 46(10):2881-2891.

Smith, N.W. et al., "Amphotericin B interactions with soluble oligomers of amyloid A beta 1-42 peptide," Bioorg. Med. Chem. (2009) 17:2366-2370.

Smith, T.F. et al., "Comparison of biosequences," Adv. In Applied Math (1981) 2:482-489.

Smith-Gill et al., "Contributions of immunoglobulin heavy and light chains to antibody specificity for lysozyme and two haptens," J. Immunol. (1987) 139:4135-4144.

Smithson, S.L. et al., "Molecular analysis of the heavy chain of antibodies that recognize the capsular polysaccharide of Neisseria meningitides in hu-Pbmc reconsituted Scid mice and in the immunized human donor," Molec. Immunol. (1999) 36:113-124.

Smolen, V.F. et al., editors, Controlled Drug Bioavailability (1984) 1:Table of Contents.

(56) References Cited

OTHER PUBLICATIONS

Solorzano-Vargas, R.S. et al., "Epitope mapping and neuroprotective properties of a human single chain FV antibody that binds an internal epitope of amyloid-beta 1-42," Molecular Immunol. (2008) 45(4):881-886.
Sondag, C.M. et al., "Beta amyloid oligomers and fibrils stimulate differential activation of primary microglia," J. Neuroinflamm. (2009) 6 article No. 1.
Song et al., Biochem. Biophys. Res. Comm (2000) 268:390-394.
Song, Y.K. et al., "Antibody mediated lung targeting of long-circulating emulsions," PDA J. of Pharm. Sci Tech. (1995) 50:372-397.
Soos, K. et al., "An improved synthesis of beta-amyloid peptides for in vitro and in vivo experiments," J. Peptide Science (2004) 10:136.
Sorensen, K. et al., "ApoE counteracts the impairment of mitochondrial activity induced by oligomeric A beta 1-42," Eur. J. Neurol. (2008) 15:45.
Spatola, A.F. et al., "Structure-activity relationships of enkephalins containing serially replaced thiomethylene amide bond surrogates," Life Sci. (1986) 38:1243-1249.
Spatola, A.F. et al., in Chemistry and Biochemistry of Amino Acids, Peptides and Proteins, B. Weinstein editor, Marcel Dekker, New York (1983) vol. VII, 267-357.
Spencer, B. et al., "Novel strategies for Alzheimer's disease treatment," Exp. Opin. Biol. Ther. (2007) 7(12):1853-1867.
Stan, R.V., "Multiple PV1 dimers reside in the same stomatal or fesestral diaphragm," Am. J. Physiol. Heart Circ. Physiol. (2004) 286(4):H1347-1353.
Standridge, J.B., "Vicious cycles within the neuropathophysiologic mechanisms of Alzheimer's disease," Curr. Alzheimer Res. (2006) 3(2):95-107.
Staros et al., "Enhancement by N-hydroxysulfosuccinimide of water-soluble carbodilimide-mediated coupling reactions," Anal. Biochem. (1986) 156(1):220-222.
Stewart, J.M. et al., Solid-Phase Peptide Synthesis, 2nd Edition, Pierce Chemical Company (1984) Table of Contents.
Stine, W. et al., "In vitro characterization of conditions for amyloid-beta peptide oligomerization and fibrillogenesis," J. Biol. Chem. (2003) 278(13):11612-11622.
Studnicka, G.M. et al., "Human-engineered monoclonal antibodies retain full specific binding activity by preserving non-CDR complementarity-modulating residues," Protein Eng. (1994) 7(6):805-814.
Suram, A. et al., "A new evidence for DNA nicking property of amyloid beta-peptide (1-42): relevance of Alzheimer's disease," Archives of Biochem. Biophys. (2007) 463(2):245-252.
Tabaton, M. et al., "Role of water-soluble amyloid-beta in the pathogenesis of Alzheimer's disease: role of amyloid-beta in Alzheimer's disease," Int. J. Exp. Path. (2005) 3(85):139-145.
Tabaton, M., "Coffee 'breaks' Alzheimer's disease," J. Alzheimer's Disease (2009) 17/3:699-700.
Taguchi, J. et al., "Different expresison of calreticulin and immunoglobulin binding protein in Alzheimer's disease brain," Acta Neuropathologica (2000) 100(2):153-160.
Takano, K., "Amyloid beta conformation in aqueous environment," Curr. Alzheimer Res. (2008) 5(6):540-547.
Takata, K. et al., "High mobility group box protein-1 enhances amyloid-beta neurotoxicity," J. Pharm. Sci. (2006) 100154P, 79th Annual Meeting of the Japanese Pharmacological Society, Yokohama, Japan, Mar. 8-10, 2006.
Takata, K. et al., "Possible involvement of small oligomers of amyloid-beta peptides in 15-deoxyDELTA12, 14 prostaglandin J2-sensitive microglial activation," J. Pharm. Sci. (2003) 91:330-333.
Takeda, S.I. et al., "Construction of chimaeric processed immunoglobulin genes containing mouse variable and human constant region sequences," Nature (1985) 314:452-454.
Tamagno, E. et al., "The various aggregation states of beta-amyloid 1-42 mediate different effects on oxidative stress, neurodegeneration, and BACE-1 expression," Free Radic. Biol. Med. (2006) 41(2):202-212.

Taniguchi, A. et al., "'Click peptide': pH-triggered in situ production and aggregation of monomer Abetal-42," Chembiochem. (2009) 10(4);710-715.
Taniuchi, M. et al., "Induction of nerve growth factor receptor in Schwann cells after axotomy," Proc. Natl. Acad. Sci. (1986) 83:4094-4098.
Tanzi, R., "Alzheimer research forum discussion: gain or loss of function—time to shake up assumptions on gamma-secretase in Alzheimer disease? Commentary," J. Alzheimer's Dis. 007) 11(3):409.
Tanzi, R.E., "Novel therapeutics for Alzheimer's disease," Neurotherapeutics (2008) 5(3):377-380.
Tarozzi, A. et al., "Cyanidin 3-O-glucopyranoside protects and rescues SH-Sy5Y cells against amyloid-beta peptide-induced toxicity," Neuroreport (2008) 19(15):1483-1486.
Taylor, L.D. et al., "A transgenic mouse that expresses a diversity of human sequence heavy and light chain immunoglobulins," Nucl. Acids. Rse. (1992) 20(23):6287-6295.
Teplow, D.B. et al., "Effects of structural modifications in a beta on its oligomer size distribution," Soc. For Neurosci. Abstract Viewer and Itinerary Planner (2002), Abstract No. 19.6, 32nd Annual meeting of the Society for Neuroscience, Orlando, FL, Nov. 2-7, 2002.
Terry, R.D. et al., "Physical basis of cognitive alterations in Alzheimer's disease: synapse loss is the major correlate of cognitive impairment," Am. Neurol. Assoc. (1991) 572-580.
Tew, D.J. et al., "Stabilization of neurotoxic soluble beta-sheet-rich conformations of the Alzheimer's disease amyloid-beta peptide," Biophys. J. (2008) 974752-2766.
Thal, D.R. et al., "Fleecy amyloid deposits in the internal layers of the human entorhinal cortex are comprised of N-terminal truncated fragments of A13," J. Neuropath. Exp. Neurol. (1999) 58:210-216.
Tijssen, P.., editor, "Hybridization with nucleic acid probes—Part II: Probe labeling and hybridzation techniques," Laboratory Techniques in Biochemistry and Molecular Biology, (1993) 24:iii-vi, 269-613, table of contents.
Tolstoshev, P., "Gene therapy, concentps, current trials and future directions," Ann. Rev. Pharmacol. Toxicol. (1993) 32:573-596.
Tomaselli, S. et al., "The alpha-to-beta conformational transition of Alzheimer's Abeta-(1-42) peptide in aqueous media is reversible: a step by step conformational analysis suggests the location of beta conformation seeding," ChemBioChem. (2006) 7(2):257-267.
Tomidokoro, Y. et al., "Familial Danish dementia: co-existence of Danish and Alzheimer amyloid subunits (Adan and Abeta) in the absence of compact plaques," J. Biol. Chem. (2005) 280(44):36883-36894.
Tomidokoro, Y. et al., "Familial Danish dementia: the relationship of two different amyloids (ADAN/ABETA) deposited in the brain," Society for Neuroscience Abstract Viewer and Itinerary Planner (2002) 2002Abstract No. 328.9, 32nd Annual Meeting of the Society of Neuroscience, Orlando, FL, Nov. 2-7, 2002.
Tomiyama, T. et al., "A new amyloid beta variant favoring oligomerization in Alzheimer's-type dementia," Ann. Neurol. (2008) 63(3):377-387.
Tsubuki, S. et al., "Dutch, Flemish, Italian and Arctic mutations of APP and resistance of Abeta to physiologically relevant proteolytic degradation," Lancet (2003) 361(9373):1957-1958.
Turner, R. et al., "The potential exploitation of plant viral translational enhancers in biotechnology for increased gene expression," Mol. Biotech. (1995) 3:225-236.
Tusell, J.M. et al., "upregulation of p21Cip1 in activated glial cells," Glia (2009) 57(5):524-534.
Ueki et al., "Solid phase synthesis and biological activities of (Arg8)-vasopressin methylenedithioether," Bioorg. Med. Chem. Lett. (1999) 9:1767-1772.
Umana, P. et al., "Engineered glycoforms of an antieuro-blastoma IgG1 with optimized antibody-dependent cellular cytotoxic activity," Nature Biotech. (1999) 17:176-180.
Urbanc, B. et al., "Computer simulations of Alzheimer's amyloid beta-protein folding and assembly," Curr. Alzheimer Res. (2006) 3(5):493-504.
Urbanc, B. et al., "In silico study of amyloid beta-protein folding and oligomerization," Proc. Natl. Acad. Sci. USA (2004) 101:17345-17350.

(56) References Cited

OTHER PUBLICATIONS

Urbanc, B. et al., "Molecular dynamics simulation of amyloid beta dimer formation," Biophys. J. (2004) 87(4):2310-2321.
Urlaub et al., "Isolation of Chinese hamster cell mutants deficient in dihydrofolate reductase activity," Proc. Natl. Acad. Sci. (1980) 77:4216-4220.
Uto, L. et al., "Determination of urinary Tamm-Horsfall protein by ELISA using a maleimide method for enzyme-antibody conjugation," J. Immunol. Methods (1991) 138:87-94.
Vajdos et al., J. Mol. Biol. (2002) 320(2):415-428.
Valincius, G. et al., "Soluble amyloid beta-oligomers affect dielectric membrane properties by bilayer insertion and domain formation: implications for cell toxicity," Biophys. J. (2008) 95(10):4845-4851.
Van Broeck, B. et al., "Current insights into molecular mechanisms of Alzheimer disease and their implications for therapeutic approaches," Neurdegenerative Dis. (2007) 4(5):349-365.
Van Broeckhoven et al., "Amyloid beta protein precursor gene and hereditary cerebral hemorrhage with amyloidosis (Dutch)" Science (1990) 248(4959):1120-1122.
Vattemi, G. et al., "Amyloid-beta42 is preferentially accumulated in muscle fibers of patients with sporadic inclusion-body myositis," Acta Neuropathol. (2009) 117(5):569-574.
Veber, D.F. et al., "The design of metabolically-stable peptide analogs," TINS (1985) 392-396.
Vestergaard, M. et al., "Detection of Alzheimer's amyloid beta aggregation by capturing molecular trails of individual assemblies," Biochem. Biophys. Res. Comm (2008) 377(2):725-728.
Vickers, "A vaccine against Alzheimer's disease," Drugs Aging (2002) 19:487-494.
Viola, K.L. et al., "Addls bind selectively to nerve cell surfaces in receptor-like puncta," Soc. For Neurosci. Abstract Viewer and Itinerary Planner (2002), Abstract No. 91.9, 32nd Annual meeting of the Society for Neuroscience, Orlando, FL, Nov. 2-7, 2002.
Viola, K.L. et al, "Immunolocalization of oligomeric Abeta42 bindnig to primary mouse hippocampal cells and B103 rat neuroblastoma cells," Society for Neuroscience Abstracts (1999), 29th Annual Meeting of the Society for Neuroscience, Miami Beach, FL, Oct. 23-28, 1999.
Wahlstrom, A. et al., "Secondary structure conversions of Alzheimer's a beta(1-40) peptide induced by membrane-mmimicking detergents," FEBS J. (2008) 275:5117-5128.
Wakutani, Y. et al., "Novel amyloid precursor protein gene missense mutation (D678N) in probable familial Alzheimer's disease," J. Neurol. Neurosurg. Psychiatry (2004) 75(7):1039-1042.
Walensky et al., "Activation of apoptosis in vivo by a hydrocarbon-stapled BH3 helix," Science (2004) 305:1466-1470.
Wallick, S.C. et al., "Glycosylation of a V(H) residue of a monoclonal antibody against alpha-1-6) dextran increases its affinity for antigen," J. Exp. Med. (1988) 168:1099-1109.
Wang, H. et al, "Soluble oligomers of Abeta(1-42) impair LTP in rat hippocampal dentate gyrus," Society for Neuroscience Abstracts (2000) Abstract No. 663.18, 30th Annual Meeting of the Society of Neuroscience, New Orleans, LA, Nov. 4-9, 2000.
Wang, H. et al., "Direct and selective elimination of specific prions and amyloids by 4,5-dianilinophthalimide and analogs," Proc. Natl. Acad. Sci. USA (2008) 105:7159-7164.
Wang, H.W. et al., "Differential effect of Abetal-42 conformation and apoE isoform on LTP," Society for Neurosci. Abstracts (2001) 752.18, 31st Annual meeting of the Society for Neurosci., San Diego, CA, Nov. 10-15, 2001.
Wang, H-W. et al., "Soluble oligomers of beta amyloid (1-42) inhibito long-term potentiation but not long-term depression in rat dentate gyrus," Brain Res. (2002) 924(2):133-140.
Wang, J. et al., "Development and characterization of a Tapir-like mouse monoclonal antibody to amyloid-beta," J. Alzheimer's Disease (2008) 14(2):161-173.
Wang, R. et al., "The profile of soluble amyloid beta protein in cultured cell medicine . . . " J. Biol. Chem. (1996) 271(50):31894-31902.
Wang, Z. et al., "Per-6-substituted-per-6-deoxy beta-cyclodextrins inhibit the formation of beta-amyloid peptide derived soluble oligomers," J. Med. Chem. (2004) 47:3329-3333.
Ward, E.S. et al., "Binding activities of a repetoire of single immunoglobulin varialbe domains secreted from *Escherichia coli*," Nature (1989) 341:544-546.
Weggen, S. et al., "Evidence that nonsteroidal anti-inflammatory drugs decrease amyloid beta-42 production by direct moculation of y-secretase activity," J. Biol. Chem. (2003) 276(34):31831-31837.
Weksler et al., "Patients with Alzheimer disease have lower levels of serum anti-amyloid peptide antibodies than healthy elderly individuals," Gerontology (2002) 37:943-948.
Wels, B. et al., "Synthesis of a novel potent cyclic peptide MC4-ligand by ring-closing metathesis," Bioorg. Med. Chem. (2005) 13:4221-4227.
Wermuth, C.G. et al., "Glossary of terms used in medicinal chemistry," Pure and Applied Chem. (1998) 70:1129-1143.
Westlind-Danielsson, A. et al., "Spontaneous in vitro formation of supramolecular beta-amyloid structures, 'betaamy balls' by beta-amyloid 1-40 peptide," Biochem. (2001) 40(49):14736-43.
White, J.A. et al., "Differential effects of oligomeric and fibrillar amyloid-beta 1-42 on astrocyte-mediated inflammation," Neurbiol. Of Disease p005) 18(3):459-465.
Wilcock et al., "Passive immunotherapy against Abeta in aged App-transgenic mice reverses cognitive deficits and depletes parenchymal amyloid deposits in spite of increased vascular amyloid and microhemorrhage," J. Neuroinflammation (2004) 1(24):1-11.
Wilcock, D.M. et al., "Intracranially administered anti-A-beta antobodies reduce beta-amyloid depsoition by mechanisms both independent of and associated with microglial activation," J. Neurosci. (2003) 23(9):3745-3751.
Williamson, M.P. et al., "Binding of amyloid beta-peptide to ganglioside micelles is dependent on histidine-13," Biochem. J. (2006) 397:483-490.
Wilson, D.M. et al., "Free fatty acids stimulate the polymerization of tau and amyloid beta peptides in vitro evidence for a common effector in pathogenesis in Alzheimer's disease," Am. J. Path. (1997) 150(6):2181-2195.
Wiltfang, J. et al., "Highly conserved and disease-specific patterns of carboxyterminally truncated A-beta peptides 1-37/38/39 in addition to 1-40/42 in Alzheimer's disease and in patients with chronic neuroinflammation," J. Neurochem. (2002) 81:481-495.
Windisch, M. et al., "The role of alpha-synuclein in neurodegenerative diseases: a potential target for new treatment strategies," Neuro-Degenerative Diseases (2008) 5(3-4):218-221.
Winnacker, E-L., From Genes to Clones: Introduction to Gene Technology (1987) Table of Contents.
Wong, P.T. et al., "Amyloid-beta membrane binding and permeabilization are distinct processes influenced separately by membrane charge and fluidity," J. Mol. Biol. (2009) 286(1):81-96.
Woodhouse, a. et al., "Vaccination strategies for Alzheimer's disease: a new hope?" Drugs Aging (2007) 24(2):107-119.
Wright, A. et al., "Antibody variable region glycosylation: position effects on antigen binding and carbohydrate structure," EMBO J. (1991) 10(10):2717-2723.
Wu et al., "Humanization of a murine monoclonal antibody by simultaneous optimization of framework and CDR residues," J. Mol. Biol. (1999) 294:151-162.
Wu, C. et al., "The structure of Abeta42 C-terminal fragments probed by a combined experimental and theoretical study," J. Mol. Biol. (2009) 287(2):492-501.
Wu, G.Y. et al., "Delivery systems for gene therapy," Biotherapy (1991) 3:87-95.
Wu, G.Y. et al., "Receptor-mediated in vitro ene transformation by a soluble DNA carrier system," J. Biol. Chem. (1987) 262:4429-4432.
Wurth, C. et al., "Mutations that reduce aggregation of the Alzheimer's Abeta42 peptide: an unbiased search for the sequence determinants of Abeta amyloidogenesis," J. Mol. Biol. (2002) 319(5):1279-1290.
Xia, W. et al., "A specific enzyme-linked immunosorbent assay for measuring beta-amyloid protein oligomers in human plasma and brain tissue of patients with Alzheimer disease," Archives of Neurology (2009) 66190-199.

(56) References Cited

OTHER PUBLICATIONS

Xia, W. et al., "Enhanced production and oligomerization fo the 42-residue amyloid beta-protein by Chinese hamster ovary cells stably expressing mutant presenilins," J. Biol. Chem. (1997) 272(12):7977-7982.
Xu, X. et al., "gamma-secretase catalyzes sequential cleavages of the a beta PP transmembrane domain," J. Alzheimer's Disease (2009) 16:211-224.
Yamamoto, N. et al., "Environment- and mutation-dependent aggregation behavior of Alzheimer amyloid beta-protein," J. Neurochem. (2004) 90:62-69.
Yamin, G. et al., "Amyloid beta-protein assembly as a therapeutic target of Alzheimer's disease," Curr. Pharm. Design (2008) 14:3231-3246.
Yamin, G. et al., "NMDA receptor-dependent signaling pathways that underlie amyloid beta-protein disruption of LTP in the hippocampus," J. Neuroscience Res. (2009) 87(8):1729-1736.
Yan, Y. et al., "Protection mechanisms against Abeta42 aggregation," Curr. Alzheimer Res. (2008) 5(6):548-554.
Yan, Z. et al., "Roscovitine: a novel regulator of P/Q-type calcium channels and transmitter release in central neurons," J. Physiol. (2002) 540(3):761-770.
Yang, M. et al., "Amyloid beta-protein monomer folding: free-energy surfaces reveal alloform-specific differences," J. Mol. Biol. (2008) 384(2):450-464.
Yang, X.D. et al., "Fully human anti-interleukin-8 monoclonal antibodies: potential therapeutics for the treatment of inflammatory disease status," J. Leukocyte Biol. (1999) 66:401-410.
Yeh, M.Y. et al., "A cell-surface antigen which is present in the ganglioside fraction and shared by human melanomas," Int. J. Cancer (1982) 29:269-275.
Yeh, M.Y. et al., "Cell surface antigens of human melanoma identified by monoclonal antibody," Proc. Natl. Acad. Sci. USA (1979) 76(6):2927-2931.
Yoshinari, K. et al., "Differential effects of immunosuppressants and antibiotics on human monoclonal antibody production is SCID mouse ascites by five heterohybridomas," Hybridoma (1998) 17(1):41-45.
Yoshitake et al., "Mild and efficient conjugation of rabbit Fab and horseradish peroxide using a maleimide compound and its use for enzyme immunoassay," J. Biochem. (1982) 92:1413-1424.
Young, K.F. et al., "Oligomeric amyloid-beta 1-42 activates extracellular signal regulated kinases ERK1 and ERK2 of the mitogen activated protein kinase pathway in SH-SY5YCELLS," Neurobiol of Aging (2004) 25:S150.
Youssef, I. et al., "N-truncated amyloid-beta oligomers induce learning impairment and neuronal apoptosis," Neurobiol of Aging (2008) 29:1319-1333.
Yu, L. et al., "Structural characterization of a soluble amyloid beta-peptide oligomer," Biochem. (2009) 48:18701877.
Yun, S. et al., "Role of electrostatic interactions in amyloid beta-protein (Abeta) oligomer formation: a discrete molecular dynamics study," Biophys. J. (2007) 92(11):4064-4077.
Yun, S.H. et al., "Amyloid-beta 1-42 reduces neuronal excitability I nmouse dentate gyrus," Neurosci. Lett. p2006) 403:162-165.
Zameer, A. et al., "Anti-oligomeric abeta single-chain variable domain antibody blocks abeta-induced toxicity against human neuroblastoma cells," J. Mol. Biol. (2008) 384(4):917-928.
Zarandi, M. et al., "Synthesis of Abeta[1-42] and its derivatives with improved efficiency," J. Peptide Sci. (2007) 13(2):94-99.
Zhao, J-H. et al., "Molecular dynamics simulations to investigate the aggregation behaviors of the Abeta(17-42) oligomers," J. Biomol. Struct. Dyn. (2009) 26(4):481-490.
Zhao, W. et al., "Identification of antihypertensive drugs which inhibit amyloid-beta protein oligomerization," J. Alzheimer's Dis. (2009) 16(1):49-57.
Zheng, J. et al., "Annular structures as intermediates in fibril formation of Alzheimer Abeta17-42," J. Phys. Chem. (2008) 112(22):6856-6865.
Zhu, D. et la., "Phospholipases A2 mediate amyloid-beta peptide-induced mitochondrial dysfunction," J. Neurosci. (2006) 26(43):11111-11119.
Zlokovic, B.V., "Clearing amyloid through the blood-brain barrier," J. neurochem. (2004) 89(40:807-811.
Zou, K et al., "A novel function of monomeric amyloid beta-protein serving as an antioxidant molecule against metal-induced oxidative damage," J. Neurosci. (2002) 22:4833-4841.
Zou, K. et al., "Amyloid beta-protein (Abeta)1-40 protects neurons from damage induced by Abetal -42 in culture and in rat brain," J. Neurochem. (2003) 87(3):609-619.
European Patent Office Search Report for Application No. 09180982 dated May 31, 2010 (4 pages).
Notice of Opposition for European Application No. 06707413/U.S. Pat. No. 1861422 dated Nov. 24, 2010.
Supplemental European Patent Office Search Report for Application No. 07864914 dated Apr. 28, 2010 (5 pages).
Supplemental European Search Report from European Patent Publication No. 2303920 dated Sep. 26, 2011.
International Preliminary Report on Patentability and Written Opinion for Application No. PCT/EP2004/000927 dated Aug. 5, 2005 (11 pages).
International Preliminary Report on Patentability and Written Opinion for Application No. PCT/EP2006/011530 dated Jun. 3, 2008 (11 pages).
International Preliminary Report on Patentability and Written Opinion for Application No. PCT/EP2008/001548 dated Sep. 1, 2008 (11 pages).
International Preliminary Report on Patentability and Written Opinion for Application No. PCT/IB2009/006636 dated Jan. 25, 2011 (7 pages).
International Preliminary Report on Patentability and Written Opinion for Application No. PCT/US2006/046043 dated Jun. 30, 2008 (32 pages).
International Preliminary Report on Patentability and Written Opinion for Application No. PCT/US2006/046148 dated Jun. 3, 2008 (8 pages).
International Preliminary Report on Patentability and Written Opinion for Application No. PCT/US2007/085932 dated Jun. 3, 2009 (5 pages).
International Preliminary Report on Patentability and Written Opinion for Application No. PCT/US2008/065199 dated Dec. 1, 2009 (10 pages).
International Preliminary Report on Patentability and Written Opinion for Application No. PCT/US2008/065205 dated Dec. 1, 2009 (6 pages).
International Preliminary Report on Patentability and Written Opinion for Application No. PCT/US2009/051721 dated Jan. 25, 2011 (7 pages).
International Search Report for Application No. PCT/EP2004/000927 dated Jun. 14, 2004 (4 pages).
International Search Report for Application No. PCT/EP2008/001548 dated Jul. 4, 2008 (3 pages).
International Search Report for Application No. PCT/EP2008/001549 mailed on Dec. 23, 2008 (6 pages).
International Search Report for Application No. PCT/IB2009/006636 dated Jan. 22, 2010 (6 pages).
International Search Report for Application No. PCT/PCT/EP2006/011530 dated Jun. 6, 2007 (7 pages).
International Search Report for Application No. PCT/US2006/046043 dated Jun. 21, 2008 (16 pages).
International Search Report for Application No. PCT/US2006/046148 dated Jun. 19, 2007 (5 pages).
International Search Report for Application No. PCT/US2007/085932 dated Spetember 22, 2008 (3 pages).
International Search Report for Application No. PCT/US2008/065199 dated Sep. 26, 2008 (4 pages).
International Search Report for Application No. PCT/US2008/065205 dated Oct. 31, 2008 (3 pages).
International Search Report for Application No. PCT/US2009/051721 mailed on Mar. 16, 2010 (6 pages).
U.S. Appl. No. 11/574,844 dated Feb. 10, 2011 (11 pages).
U.S. Appl. No. 11/574,847 dated Jul. 14, 2011 (22 pages).

(56) References Cited

OTHER PUBLICATIONS

U.S. Appl. No. 11/574,876 dated Jan. 23, 2012 (17 pages).
U.S. Appl. No. 11/885,362 dated Jul. 22, 2010 (10 pages).
U.S. Appl. No. 11/885,362 dated Mar. 29, 2011 (8 pages).
U.S. Appl. No. 11/945,124 dated Mar. 3, 2010 (15 pages).
U.S. Appl. No. 11/945,124 dated Oct. 14, 2010 (8 pages).
U.S. Appl. No. 12/509,315 dated Jun. 6, 2012 (10 pages).
U.S. Appl. No. 12/509,325 dated Jun. 6, 2012 (14 pages).
U.S. Appl. No. 12/529,467 dated Dec. 6, 2011 (24 pages).
U.S. Appl. No. 12/529,467 dated May 24, 2012 (19 pages).
U.S. Appl. No. 13/102,713 dated Apr. 19, 2012 (20 pages).
U.S. Appl. No. 13/188,034 dated Jan. 3, 2012 (35 pages).
U.S. Appl. No. 13/188,034 dated Sep. 11, 2012 (18 pages).
U.S. Appl. No. 11/574,844 dated Aug. 11, 2011 (14 pages).
U.S. Appl. No. 11/574,844 dated May 9, 2012 (8 pages).
U.S. Appl. No. 11/574,847 dated Feb. 10, 2012 (12 pages).
U.S. Appl. No. 11/945,124 dated Apr. 4, 2011 (8 pages).
U.S. Appl. No. 11/945,124 dated Mar. 5, 2012 (7 pages).
Sakmann, B. et al., "Single-channel recording" in Antibodies, 2nd edition, Springer, Table of Contents (1995).
Tamura, M. et al., "Structural correleates of an anticarcinoma antibody: identification of specificity-determining residues (SDRs) and development of a minimally immunogenic antibody variant by retention of SDRs only," J. Immunol. (2000) 164(3):1432-1441.
U.S. Appl. No. 11/574,847 dated Oct. 4, 2012 (8 pages).
U.S. Appl. No. 11/574,876 dated Nov. 15, 2012 (9 pages).
U.S. Appl. No. 13/102,713 dated Oct. 1, 2012 (14 pages).
U.S. Appl. No. 11/945,124 dated Oct. 9, 2012 (7 pages).
Citron, M., "Alzheimer's disease: strategies for disease modification," Nature Reviews Drug Discovery (2010) 9:387-398.
Kundrot, C.E. et al., "Which strategy for a protein crystallization project?" Cell. Mol. Life Sci. (2004) 61:525-536.
McPherson, A., "Current approaches to macromolecular crystallization," Eur. J. Biochem. (1990) 189:1-23.
Verhoeven, M. et al., "Engineering of antibodies," Bioessays (1988) 8(2):74-78.
European Patent Office Action for Application No. 087160818 dated Dec. 22, 2011 (6 pages).
European Patent Office Action for Application No. 101783942 dated Mar. 2, 2012 (4 pages).
European Patent Office Action for Application No. 101783942 dated Aug. 22, 2012 (4 pages).
International Search Report for Application No. PCT/US2011/047622 dated Jan. 2, 2012 (6 pages).
Written Opinion for Application No. PCT/US2011/047622 dated Jan. 2, 2012 (8 pages).
U.S. Appl. No. 13/085,891 dated Apr. 18, 2013 (16 pages).
U.S. Appl. No. 13/085,891 dated Nov. 26, 2013 (10 pages).
U.S. Appl. No. 11/885,362 dated Sep. 26, 2013 (11 pages).
U.S. Appl. No. 11/574,876 dated Sep. 30, 2013 (11 pages).
Ma, B. et al., "Polymorphic C-terminal-sheet interactions determine the formation of fibril or amyloid-derived diffusible ligand-like globulomer for the Alzheimer A42 dodecamer," J. Biol. Chem. (2010) 285(47):37102-37110.
European Patent Office Action for Application No. 10179297 dated Jul. 21, 2014 (9 pages).
European Patent Office Action for Application No. 10179281 dated Jul. 21, 2014 (11 pages).
European Patent Office Action for Application No. 10179255 dated Jul. 21, 2014 (11 pages).
European Patent Office Action for Application No. 11715837 dated Oct. 10, 2014 (4 pages).
U.S. Appl. No. 13/102,713 dated Mar. 14, 2014 (9 pages).
Acha-Orbea et al., "Anti-T-cell receptor V beta antibodies in autoimmunity," Immunol Ser. (1993) 59:193-202.
Anderson et al., "Characterization of beta amyloid assemblies in drusen: the deposits associated with aging and age-related macular degeneration," Experimental Eye Research (2004) 78:243-256.

Bard et al., "Epitope and isotype specificities of antibodies to beta-amyloid peptide for protection against Alzheimer's disease-like neuropathology," Proc. Natl. Acad. Sci. (2003) 100(4):2023-2028.
Bard et al., "Peripherally administered antibodies against amyloid bipeptide enter the central nervous system and reduce pathology in a mouse model of Alzheimer disease," Nature Med. (2000) 6:916-919.
Brown, M. et al., "Tolerance to single, but not multiple, amino acid replacements in antibody V-H CDR2: a means of minimizing B cell wastage from somatic hypermutation?" J. Immunol (1996) 156(9):3285-3291.
Campbell et al., "General properties and applications of monoclonal antibodies," Elsevier Science Publishers B.V. (1984) pp. 1-32.
Celli et al., "Origin and pathogenesis of antiphospholipid antibodies," Braz. J. Med. Biol. Res. (1998) 31(6):723732.
Database EMBL, "Mouse immunoglobulin rearranged kappa-chain V-region V105 gene from, C.AL20-TEPC-105 myeloma, exons 1 and 2," Jul. 16, 1988, Database Accession No. M12183.
Database EMBL, "Mus musculus F5.20G3 low-affinity anti-phosphorylcholine IgG antibody mRNA, partial cds," Feb. 8, 1999, Database Accession No. AF044238.
Database Geneseq, "Anti-human Fas monoclonal antibody CH11 light chain cDNA," retrieved from EBI Accession No. GSN:AAV66736, Jan. 18, 1999, Database Accession No. AAV66736.
Database Geneseq, "Mouse DNA encoding antibody 3D8 heavy chain variable region," Apr. 22, 2003, Database Accession No. ABX16569.
Database Geneseq, "Mouse monoclonal antibody 4785 heavy chain SEQ ID 38", retrieved from EBI Accession No. GSP:ADX39137,(2005) Database Accession No. ADX39137.
Database Geneseq., Humanized monoclonal antibody H74785-2 heavy chain, retrieved from EBI accession No. GSP:ADX39139, 2005, Database Accession No. ADX39139.
Database Geneseq., "Humanized monoclonal antibody Hu4785-2 partial protein," retrieved from EBI Accession No. GSP:ADX39104 (2005) Database Accession No. ADX39104.
Database Geneseq., "Humanized monoclonal antibody Hu4785-2 VH region," retrieved from EBI accession No. GSP:ADX39143 (2005), Database Accession No. ADX39143.
Database Geneseq., "Mouse monoclonal antibody 4785 heavy chain SEQ ID 1," retrieved from EBI Accession No. GSP:ADX39100 (2005) Database Accession No. ADX39100.
Database NCBI Protein dated Apr. 11, 1996, Accession No. AAA96779.
Database NCBI Protein dated Mar. 23, 2002, Accession No. AAA92933.
Database NCBI Protein, dated Mar. 23, 2002, Accession No. AAL92941.
Database NCBL Protein, dated Aug. 30, 1993, Accession No. AAA38584.
David et al., A significant reduction in the incidence of collagen induced arthritis in mice treated with anti-TCRV-beta antibodies, J. Cell Biochem. (1991) 179.
DeGiorgi et al., "Induction of foetal lethality in AKR offspring after repeated inoculations into AKR females of anti-TCR/V beta 6 monoclonal antibody," Res. Immunol (1993) 144(4):245-255.
DeGiorgi et al., "Murine hybridomas secreting monoclonal antibodies reacting with Misa antigens," Exp. Clin. Immunogenet. (1993) 10(4):219-223.
Ding et al., "Targeting age-related macular degeneration with Alzheimer's disease based immunotherapies: antiamyloid-beta antibody attenuates pathologies in an age-related macular degeneration mouse model," Vision Research, Pergamon Press, Oxford, GB (2007) 48(3):339-345.
Dorronsoro et al., "Peripheral and dual binding site inhibitors of acetylcholinesterase as neurodegenerative disease-modifying agents," Exp. Opin. Ther. Pat. (2003) 13(11):1725-1732.
Frenkel et al., "Modulation of Alzheimer's beta-amyloid neurotoxicity by site-directed single-chain antibody," J. Neuroimmunol. (2000) 106(1-2):23-31.
Fujimoro et al., "Production and characterization of monoclonal antibodies specific to multi-ubiquitin chains of polyubiquitinated proteins," FEBS (1994) 349:173-180.

(56) References Cited

OTHER PUBLICATIONS

Fujimoro et al., "Production of antipolyubiquitin monoclonal antibodies and their use for characterization and isolation of polyubiquitinated proteins," Meth. Enzymol. (2005) 399:75-86.
Fukuchi et al., "Amelioration of amyloid load by anti-Abeta single-chain antibody in Alzheimer mouse model," Biochem. Biophys. Res. Commun. (2006) 344(1):79-86.
Guo et al., "Targeting amyloid-beta in glaucoma treatment," Proc. Natl. Acad. Sci. USA (2007) 104(33):1344413449.
Hicke, "Protein regulation by monoubiquitin," Nat. Rev. (2001) 2:196-201.
Kim et al., "Development of conformation-specific antibodies for neutralization of beta-amyloid oligomers," Neurobiol. Aging (2004) 25(1):5145, P1-175 Abstract.
Kisilevsky et al., "Arresting amyloidosis in vivo using small-molecule anionic sulphonates or sulphates: implications for Alzheimer's disease," Nat. Med. (1995) 1(2):143-148.
Kisilevsky, "Anti-amyloid drugs potential in the treatment of diseases associated with aging," Drugs Aging (1996) 8(2):75-83.
Langdon et al., "Germline sequences of VH7183 gene family members in C57BL/6 mice demonstrate natural selection of particular sequences during recent evolution," Immunogen (2000) 51:241-245.
Lee et al., "Molecular cloning of agonistic and antagonistic monoclonal antibodies against human 4-IBB," Eur. J. Immunogenet. (2002) 29(5):449-452.
LeVine, H, III., "4,4'-dianilino-1,1''-binaphthyl-5'-disulfonate (bis-ANS) reports on non-beta-sheet conformers of Alzheimer's peptide beta (1-40), Arch Biochem. Biophys. (2002) 404:106-115.
Liu, et al., "Single chain variable fragments against beta-amyloid (Abeta) can inhibit Abeta aggregation and prevent Abeta-induced neurotoxicity," Biochem. (2004) 43:6959-6967.
Lund et al., "Oligosaccaride-protein interactions in IgG can modulate recognition by Fc-gamma receptors," FASEB J. (1995) 9(1):115-119.
Mckinnon et al., "Caspase activation and amyloid precursor protein cleavage in rat ocular hypertension," Investigative Ophthalmology & Visual Science (2002) 43(4):1077-1087.
Mclaurin et al., "therapeutically effective antibodies against amyloid-beta peptide target amyloid-beta residues 4-10 and inhibit cytotoxicity and fibrillogenesis," Nat. Med. (2002) 8(11):1263-1269.
Moretto et al., "Conformation-sensitive antibodies against Alzheimer amyloid-beta by immunization with a thioredoxin-constrained B-cell epitope peptide," J. Biol. Chem. (2007) 282(15):11436-11445.
Nemes et al., "Cross-linking of obiquitin, HSP27, parkin, and alpha-synuclein by gamma-glutamyl-8-lysine bonds in Alzheimer's neurofibrillary tangles," Faseb J. (2004) 18:1135-1137.
Nicolau et al., "A liposome-based therapetuci vaccine against beta-amyloid plaques on the pancreas of transgenic Norba mice," Proc. Natl. Acad. Sci. USA (2002) 99(4):2332-2337.
Rzepecki et al., "Prevention of Alzheimer's disease-associated Abeta aggregation by rationally designed nonpeptide beta-sheet ligands," J. Biol. Chem. (2004) 279(46):47497-47505.
Schable et al., "Characteristics of the immunoglobulin V kappa genes, pseudogenes, relics and orphons in the mouse genome," Eur. J. Immunol (1999) 29:2082-2086.
Schenk et al , "Immunization with amyloid-beta attenuates Alzheimer'disease-like pathology in the PDAPP mouse," Nature (1999) 400:173-177.
Solomon et al., "Disaggregation of Alzheimer Beta-Amyloid by site-directed mAb," Proc. Natl. Acad. Sci. USA(1997) 94:4109-4112.
Solomon et al., "Monoclonal antibodies inhibit in vitro fibrillar aggregation fo the Alzheimer beta-amyloid peptide," Proc. Natl. Acad. Sci. USA (1996) 93:452-455.
Tenno et al., "Structural basis for distinct roles of Lys63- and Lys48-linked polyubiquitin chains," Genes to Cells (1994) 9:865-875.
Van Gool et al., "Concentrations of amyloid-beta protein in cerebrospinal fluid increase with age in patients free from neurodegenerative disease," Neurosci Left. (1994) 172(1-2):122-124.
Weaver-Feldhaus et al., "Yeast mating for combinatorial Fab library generation and surface display," FEBS Lett. (2004) 564(2):24-34.
U.S. Appl. No. 12/529,467 dated Jul. 9, 2014.
U.S. Appl. No. 13/102,713 dated Jun. 24, 2014.
Chen, C., "Beta-amyloid increases dendritic Ca2+ influx by inhibiting the A-type K+ current in hippocampal CA1 pyramidal neurons," Biochem. Biophys. Res. Comm. (2005) 338:1913-1919.
Jeon, D. et al., "Impaired long-term memory and long-term potentiation in N-type Ca2+ channel-deficient mice," Genes, Brain Behavior (2007) 6:375-388.
Lipscombe, D. et al., "Functional diversity in neuronal voltage-gated calcium channels by alternative splicing of Cay. alpha1," Mol. Neurobiol. (2002) 26(1):21-44.
Rovira, C. et al., "Abeta(25-35) and Abeta(1-40) act on different calcium channels in CA1 hippocampal neurons," Biochem. Biophys. Res. Comm. (2002) 296;1317-1321.
Shankar, G.M. et al., "Natural oligomers of the Alzheimer amyloid-beta protein induce reversible synapse loss by modulating an NMDA-type glutamate receptor-dependent signaling pathway," J. Neurosci. (2007) 27(11):2866-2875.
Ye, C.P. et al., "Protofibrils of amyloid beta-protein inhibit specific K+ currents in neocortical cultures," Neurobiol. Disease (2003) 13:177-190.
U.S. Appl. No. 12/529,467 dated Feb. 14, 2014 (17 pages).

* cited by examiner

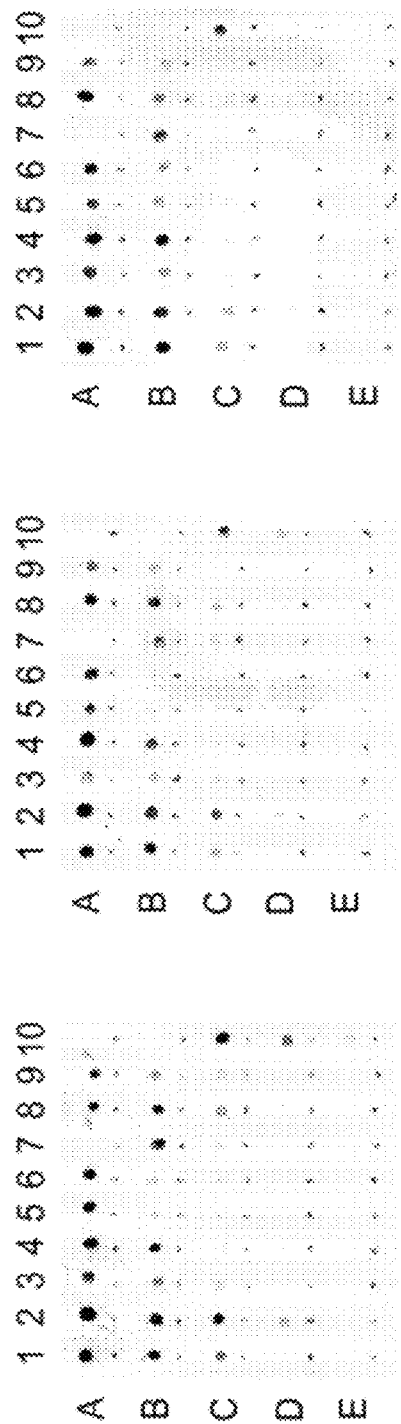
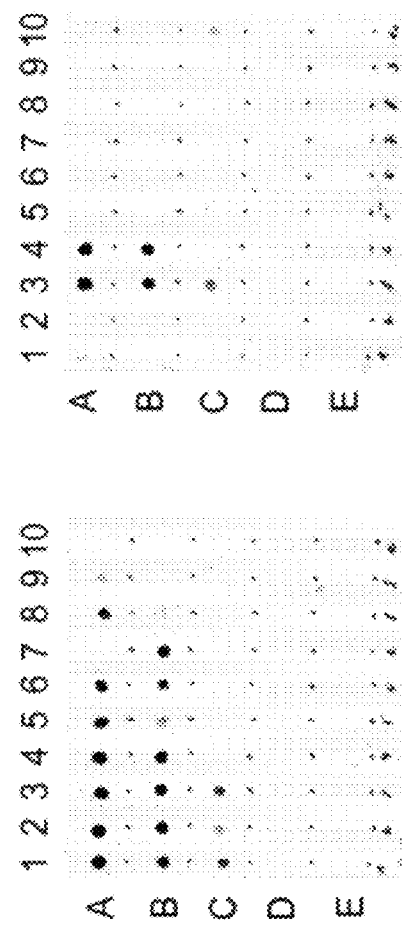
FIG. 10A FIG. 10B FIG. 10C FIG. 10D FIG. 10E

```
                         SEQUENCE LISTING

<160> NUMBER OF SEQ ID NOS: 2

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 42
<212> TYPE: PRT
<213> ORGANISM: Rattus rattus

<400> SEQUENCE: 2

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

AMYLOID BETA(1-42) OLIGOMERS, DERIVATIVES THEREOF AND ANTIBODIES THERETO, METHODS OF PREPARATION THEREOF AND USE THEREOF

CROSS-REFERENCE TO RELATED APPLICATIONS

This is a continuation of U.S. patent application Ser. No. 12/559,255, filed on Sep. 14, 2009, which is a divisional of U.S. patent application Ser. No. 10/543,841, filed on Oct. 4, 2006, which is now U.S. Pat. No. 7,902,328, which is the U.S. national stage entry of International Patent Application No. PCT/EP2004/000927, filed on Feb. 2, 2004, which claims priority to German Patent Application No. 10303974.0, filed on Jan. 31, 2003, the contents of all of which are hereby incorporated by reference.

The invention relates to neuromodulating oligomers of the amyloid β(1-42) protein, to a specific method of preparation by which said oligomers are obtainable in a reproducible manner and with high yield, and to the use of said oligomers as diagnostic and therapeutic agents, for generating oligomer-specific antibodies and for finding substances capable of interacting with said oligomers and with the formation thereof.

The invention likewise also relates to derivatives of said oligomers, in particular to crosslinked oligomers and oligomers based on truncated forms of the amyloid β(1-42) protein thereof, to the preparation thereof and the use thereof.

Corresponding methods of generating the antibodies and of finding the substances are also described as are the antibodies themselves and the use of said antibodies and substances as diagnostic and therapeutic agents.

Amyloid β(1-42) protein, also referred to as Aβ(1-42) for short, is a central component of insoluble extracellular depositions (senile or neuritic plaques) composed of proteins, lipids, carbohydrates and salts in the brains of Alzheimer and Down's syndrome patients (C. L. Masters et al. PNAS 82, 4245-4249, 1985). This protein which tends to polymerize in an aqueous environment may be present in very different molecular forms.

A simple correlation of the deposition of insoluble protein with the occurrence or progression of dementia disorders such as, for example, Alzheimer's disease has proved to be unconvincing (R. D. Terry et al Ann. Neurol. 30. 572-580 (1991), D. W. Dickson et al. Neurobiol. Aging 16, 285-298 (1995)). In contrast, the loss of synapses and cognitive perception seems to correlate better with soluble forms of Aβ(1-42) (L. F. Lue et al. Am. J. Pathol. 155, 853-862, (1999), C. A. McLean et al. Ann. Neurol. 46, 860-866 (1999)).

With the soluble forms of Aβ(1-42), there are essentially two different hypotheses regarding the molecular forms supposedly to be the cause for dementia disorders such as Alzheimer's disease.

Firstly, a cytotoxic action of Aβ(1-42) protofibrils is postulated. The latter are still soluble, fibrillar relatively highly aggregated Aβ(1-42) forms having molecular weights in the range from 150-250 kDa (Arispe et al. PNAS 90. 567 (1993), Lashuel et al., Nature 418, 291 (2002)) which, due to pore-forming properties, apparently cause an uncontrolled calcium influx through the membranes of neuronal cells.

Secondly, oligomeric Aβ(1-42) derivatives having molecular weights in the range from 15-30 kDa are described (M. P. Lambert et al. PNAS 95, 6448-6453 (1998)). These nonfibrillar oligomers also referred to as amyloid derived, diffusible and dementing ligands (ADDL's for Amyloid Derived Dementing Ligands, cf. U.S. Pat. No. 6,218,506 and WO 01/10900, or for Amyloid Derived Diffusible Ligands, cf. Lambert et al. supra) can be found in preparations showing an inhibiting influence on the rate of long-term potentiation of neurons in hippocampal sections.

However, the state of previous research on oligomers is characterized by great uncertainty over the actually relevant species. The information in the literature differs greatly. Thus, U.S. Pat. No. 6,218,506 describes ADDLs having from 3 to 12 subunits, whereas the ADDLs described in WO 01/10900 may have up to 24 subunits.

More specifically, at least two forms are discussed which have in a gel-electrophoretic analysis under nondenaturing conditions molecular weights in the range from 27 to 28 kDa and 23 to 24 kDa (U.S. Pat. No. 6,218,506) or from about 26 kDa to 28 kDa (WO 01/10900) and, respectively, 17 kDa and 27 kDa (M. P. Lambert et al. PNAS 95, 6448-6453 (1998)) and in an SDS gel-electrophoretic analysis under denaturing conditions molecular weights of 17 kDa and 22 kDa (M. P. Lambert et al. PNAS 95, 6448-6453 (1998)) and, respectively, of from about 22 kDa to about 24 kDa and from about 18 kDa to about 19 kDa (WO 01/10900). SDS-stable Aβ(1-42) oligomers having molecular weights in the range from 8 kDa and 12 kDa have also been detected previously by Western blot methods on brains of Alzheimer patients (C. A. McLean et al. Ann. Neurol. 46, 860-866 (1999)).

The preparation protocols described have the disadvantage of resulting in inhomogeneous oligomer preparations.

Thus it has not been possible yet to provide in a reproducible manner, let alone unambiguously identify, the molecular forms of Aβ(1-42) responsible for neuromodulation.

However, the importance of a homogeneous preparation can be gauged, for example, from the course of a first clinical study of active immunization on Alzheimer patients. Vaccination with a pre-aggregated form of Aβ(1-42) resulted in considerable side effects (mengioencephalitis, hemorrhages) in some of the patients, since the antibodies formed also recognized the Aβ(1-42) forms presumably required for cell lining, resulting in inflammatory reactions (D. Schenk.; Nat. Rev. Neurosci. 3, 824-828 (2002)).

A custom therapy which especially aims at neutralizing the actually damaging protein form therefore absolutely requires the identification and defined preparation of the latter.

In addition, the occurrence of N-terminally truncated forms of the Aβ(1-42) protein in connection with Alzheimer's disease has been reported. Apart from Aβ(1-42) N-terminally truncated forms were also detected in the depositions of brains of deceased Alzheimer patients as early as 1985 (C. Masters et al., PNAS 82, 4245-4249 (1985)). Thus, particular proteases present in the brain, such as neprilysin (NEP 24.11) or IDE (short for insulin degrading enzyme), are also known to be able to degrade Aβ(1-42) (D. J. Selkoe, Neuron 32, 177-180, (2001)).

However, the importance of the N-terminally truncated forms in the pathogenesis of Alzheimer's disease is unclear (E. B. Lee et al, JBS 278, 4458-4466 (2003)). Interestingly, some patients suffering from sporadic or familial Alzheimer's disease or Down's syndrome preferably accumulate these truncated forms (J. Näslund et al, PNAS 91, 8378-8382, (1994), C. Russo et al., Nature 405, 531-532, (2000), T. C. Saido et al, Neuron 14, 457-466, (1995)). A relatively recent study (N. Sergeant et al, J. of Neurochemistry 85, 1581-1591, (2003)) showed that 60% of all insoluble Aβ peptides in the brains of deceased Alzheimer patients are based on N-terminally truncated forms.

Antibodies directed against monomeric Aβ(1-42) protein and particular fragments thereof have already been described.

Thus, WO 03/016466 and WO 03/016467 relate to the monoclonal antibody 266 and analogs thereof which lack a particular glycosylation site in CDR2. Humanized versions thereof (Hu-266) are also known. These documents also mention other monoclonal antibodies which, like antibody 226, recognize epitopes in the region of amino acids 13-28 of Aβ(1-42). These include the antibodies 4G8 (also mentioned in Lue et al. (1999), supra) and 1C2. Furthermore, McLean et al. (1999), supra, mentions the monoclonal antibody 1E8 which apparently recognizes an epitope in the region of amino acids 18-22 of Aβ(1-42).

Moreover, a number of further antibodies are known which recognize epitopes of N-terminal sequences of Aβ(1-42). These include commercially available, monoclonal antibody 6E10 (also mentioned in WO 01/10900; Näslund et al. (1994), supra; Sergeant et al. (2003), supra) and the monoclonal antibodies 306 and 1005 (see WO 03/016467) and also Ban50 and NAB228 (Lee et al. (2003), supra).

Furthermore, mention must be made of the monoclonal antibodies WO2, 21F12 and 3D6 and of the polyclonal serum ADA42 (Sergeant et al. (2003), supra).

An overview over anti-Aβ(1-42) antibodies currently undergoing preclinical testing can be found in Schenk et al. (2002), supra.

The present invention is based on the object of providing the molecular forms which cause the neuromodulating and, in particular, neuron-damaging action of Aβ(1-42) and whose presence is increased in dementia disorders such as Alzheimer's disease and Down's syndrome and achieves said object by means of particular Aβ(1-42), oligomers which are obtainable in the form of homogeneous preparations from monomeric Aβ(1-42) protein, using a special method, and by means of particular derivatives of said oligomers, in particular crosslinked oligomers and oligomers based on truncated Aβ(1-42) forms. The method of preparation enables peptide-synthetic Aβ(1-42) protein which is poorly soluble in aqueous media to be converted to defined soluble oligomers with high yield.

The present invention therefore relates to the subject matters defined in the claims.

Thus, the present invention relates to oligomers of the amyloid β(1-42) protein, said oligomers having an apparent molecular weight of about 15 kDa, 20 kDa, 38 kDa or 48 kDa in SDS gel electrophoresis, or to derivatives of said oligomers having a molecular weight which may or may not have changed according to the derivatization.

Amyloid β(1-42) protein is a polypeptide having 42 amino acids which is derived from the amyloid precursor protein (APP) by proteolytic processing. This also includes, in addition to human variants, isoforms of the amyloid β(1-42) protein present in organisms other than humans, in particular other mammals, especially rats.

According to a particular embodiment, the present invention relates to oligomers of human amyloid β(1-42) proteins. Human amyloid β(1-42) proteins include in particular the protein having the amino acid sequence SEQ ID NO:1 and also muteins and allelic variants thereof derived from said sequence in particular by amino acid exchange. In this connection, very particular mention must be made of the following amino acid substitutions: A21G, E22K, E22Q, E22G and D23N. Thus, the muteins or allelic variants of the amyloid β(1-42) protein include according to the invention in particular proteins having an amino acid sequence SEQ ID NO:1 in which one or more amino acids selected from among alanine 21, glutamic acid 22 and aspartic acid 23 have been substituted by a different amino acid preferably selected from among glycine, lysine, glutamine and asparagine. Particularly important according to the invention are substitutions in position 22, in particular by glutamine or glycine.

According to another particular embodiment, the present invention relates to oligomers of rat amyloid β(1-42) proteins. Rat amyloid β(1-42) proteins include in particular the protein having the amino acid sequence SEQ ID NO:2 and also muteins and allelic variants thereof derived from said sequence in particular by amino acid exchange. In this connection, very particular mention must be made of those amino acid substitutions which correspond to the amino acid substitutions discussed for the human sequence.

Amyloid β(1-42) protein may be prepared by known peptide-synthetic methods or recombinantly. In addition, a number of these proteins are commercially available. The same applies also to muteins and allelic variants.

The oligomers of the invention are obtainable by oligomerization of amyloid β(1-42) protein. The oligomerization comprises a noncovalent aggregation of monomeric amyloid protein so that the oligomers of the invention can be assumed to be composed of a plurality of amyloid β(1-42) protein monomers.

Depending on the degree of oligomerization, the oligomers of the invention have different molecular weights. Thus it is possible to assign apparent molecular weights to said oligomers by means of denaturing gel electrophoresis. Said molecular weights are about 15 kDa for the oligomer A1, about 20 kDa for the oligomer A2, about 38 kDa for the oligomer B1 and about 48 kDa for the oligomer B2, when gel electrophoresis is carried out under standard denaturing conditions (Tris-glycine gel, 4-20%, cf. Lämmli U K, Nature 227, 680-685 (1970)), with the following standard proteins having the following apparent molecular weights under identical conditions: myosin 250 kDa, bovine serum albumin 98 kDa, glutamine hydrogenase 64 kDa, carboanhydrase 36 kDa, myoglobin 30 kDa, lysozyme 16 kDa, aprotinin 6 kDa, insulin B chain 4 kDa (cf. Blue Pre-stained Standard). According to another aspect, the molecular weights for the oligomers B are from about 64 to 90 kDa, when gel electrophoresis is carried out under standard native conditions (Tris glycine gel, 4-20%), with the following standard proteins having the following apparent molecular weights under identical conditions: myosin 250 kDa, bovine serum albumin 98 kDa, glutamine hydrogenase 64 kDa, carboanhydrase 36 kDa, myoglobin 30 kDa, lysozyme 16 kDa, aprotinin 6 kDa, insulin B chain 4 kDa (cf. Blue Pre-stained Standard).

According to another aspect, the oligomers of the invention are characterized by an affinity for neuronal cells. It can be assumed that said oligomers bind to particular cell surface proteins, in particular receptors.

Accordingly, the present invention also relates to a method of determining the binding of an oligomer of the invention to a predefined cellular structure, which method comprises
i) allowing said oligomer of the invention to act on said cellular structure and
ii) determining whether said oligomer of the invention binds to said cellular structure.

According to another aspect, the oligomers of the invention are characterized by a neuromodulating action. This neuromodulating action can manifest itself in particular in a reduced survivability of neuronal cells, for example neuroblastoma cells (neuro-toxicity) when at least one oligomer of the invention is allowed to act on a culture of these cells. It is possible here to assess the survivability of said cells in a manner known per se, for example by determining the extent of apoptosis caused by the action of the oligomers of the invention. For this purpose, suitable assay methods, for example colorimetric methods based on 3-[4,5-dimethylthiazol-2-yl]-2,5-diphenyl-tetrazolium bromide (MTT) are available. This neuromodulating action can manifest itself in vivo in particular in a modulation of the firing rate of neurons.

Accordingly, the present invention also relates to a method of determining the activity, in particular neurotoxicity, of an oligomer of the invention, which method comprises
i) allowing said oligomer of the invention to act on cells and
ii) determining whether the state of said cells is modified.

It is possible to provide for said methods oligomer of the invention in the above-described manner, for example in the form of any of the above-mentioned compositions. The cells or cellular structures are conveniently provided in vitro, in particular as cell culture or else, in cellular structures, as homogenates. Here, neuronal cells and, in particular, neuroblastoma cells serve to determine neuro-toxicity. Alternatively, it is also possible to provide the cells in vivo, in particular as part of an organism, for example of an experimental animal, or ex vivo.

The state of the cells is usually determined at least once prior to and at least once after the action of the oligomer. If comparison between the state prior to and the state after the action results in a deviation, the oligomer tested has activity.

The type of the state to be determined depends on the type of the activity to be determined. Neurotoxicity can be determined by determining the survivability, for example. For this purpose, the proportion of living cells based on the total number of cells prior to and after the action of the oligomer can be determined and compared to one another.

Based upon the methods above of determining binding or activity, it is possible, according to particular embodiments, to test substances on whether they inhibit binding of oligomers of the invention and/or modulate, i.e. in particular reduce or essentially completely inhibit, or enhance the activity thereof.

For this purpose, the method is in principle carried out at least twice, once in the presence of the test substance and once more without test substance. To this end, said test substance is added to the oligomers usually after they have been provided.

However, if it is intended to determine whether or not a substance to be tested influences formation of said oligomers, said substance is expediently added to the reactant(s) used for oligomer formation, already prior to formation of said oligomers, i.e. already before they have been provided. Thus it is possible to carry out the preparation method of the invention with addition of the test substance and then to determine whether and to what extent the oligomers are formed. For this purpose, it can be determined whether the method products obtained in this way have the properties of the oligomers of the invention, i.e. their molecular weight, binding ability and activity, for example.

For the purposes of a neuromodulating action as pronounced as possible, preference must be given to the oligomers B of the invention. In this regard, preference is also given to derivatives of these oligomers, with particular emphasis being given to the oligomers based on an N-terminally truncated Aβ(1-42) protein.

For process engineering reasons, the oligomers A and the oligomers B may be produced as a mixture in the form of compositions which, in addition to the oligomers, further comprise small proportions of other polypeptides, in particular monomeric amyloid β(1-42) protein and, where appropriate, also higher molecular weight forms of aggregated amyloid β(1-42) protein. Compositions of this kind are likewise subject matter of the present invention and are distinguished in particular by the proportion of oligomer(s) of the invention being at least 70% by weight, preferably at least 90% by weight, and in particular at least 95% by weight, based on the totality of proteins derived from amyloid β(1-42) protein. In a preparation of oligomers A, the proportion of oligomer A2 (20 kDa band in the SDS gel) is at least 50% by weight and preferably at least 70% by weight and in particular at least 85% by weight. In a preparation of oligomers B, the proportion of oligomers B1 and B2 (38 kDa and 48 kDa bands in the SDS gel) is at least 60% by weight, preferably at least 75% by weight and in particular at least 90% by weight.

The oligomers of the invention may also be derivatized. The purpose of such derivatizations may be, for example, to modulate the physicochemical properties of said oligomers, in particular with respect to bioavailability, to provide said oligomers with a detectable label or to immobilize said oligomers, for example to be able to couple them to supports. Labeling and immobilization are particularly important for diagnostic applications.

Suitable labels familiar in the protein-biochemical field are sufficiently known to the skilled worker. These include fluorescent labels, for example particular fluorescein and tetramethylrhodamine derivatives, luminescent labels, colorimetric labels, radio labels and magnetic labels and also labels with affinity for complementary binding partners, such as biotin and streptavidin derivatives.

With respect to the apparent molecular weights, it must be taken into account that the oligomer derivatives have molecular weights which may have increased correspondingly, compared to the nonderivatized oligomers, but with the aggregation number being identical. Thus, for example, a biotin derivative based on the Aβ(1-42) oligomer B1 having a molecular weight of 38 kDa in the SDS gel has a molecular weight of 42 kDa.

According to a particular embodiment of the present invention, the oligomers are crosslinked. Suitable crosslinkers are known to the skilled worker and are usually bifunctional reagents such as formaldehyde, glutardialdehyde, disuccinimidyl suberate, dithiobis(succinimidyl propionate), disuccinimidyl tartrate, disulfo-succinimidyl tartrate, dimethyl adipimidate, dimethyl pimelidate, dimethyl suberimidate, dimethyl 3,3'-dithiobispropionimidate, N-γ-maleinimidobutyloxy-succinimide ester, succinimidyl 4(N-maleinimidomethyl)cyclohexane-1-carboxylate, N-succinimidyl (4-iodacetyl)aminobenzoate and N-succinimidyl 3-(2-pyridyldithio)-propionate.

Such crosslinked oligomers have the advantage that they are stabilized and that their oligomerization is usually no longer reversible. They are therefore particularly suitable for use in diagnostic test systems or as immunogen for production of oligomer-specific antibodies.

The derivatives of oligomers of the invention also include oligomers of fragments of the amyloid β(1-42) protein. Preference is given to those fragments which are obtainable by the action of naturally occurring proteases. The fragments obtainable by proteolysis in physiological buffers under non-denaturing conditions, in particular, have increased proteolytic stability compared to the amyloid β(1-42) protein. Preference is given to fragments obtainable by the action of endopeptidases. According to a particular embodiment of the present invention, said fragments are obtainable by the action of trypsin, chymotrypsin, thermolysin, elastase, papain or endoproteinase GluC. According to another aspect, preference is given to those fragments whose oligomers of the invention are distinguished by a neuromodulating action. For further illustration of this aspect, reference is made to the corresponding comments on the neuromodulating action of inventive oligomers of the amyloid β(1-42) protein.

Structurally, preferred fragments are in particular characterized in that they are derived from the amyloid β(1-42)

protein by removal of N-terminal sequences. According to one aspect, said N-terminal sequences may be fragments having up to 23, preferably having up to 21 and in particular having up to 19, amino acids of the N-terminal sequence of the amyloid β(1-42) protein. Accordingly, preference is given according to the invention to Aβ(1-42) protein fragments whose sequence comprises the contiguous amino acids 24 to 42, preferably 22 to 42 and in particular 20 to 42. According to another aspect, the N-terminal sequences to be removed may be sequences having at least 7, preferably having at least 9 and in particular having at least 11, amino acids of the N-terminal sequence of the amyloid β(1-42) protein. Accordingly, preference is given according to the invention in particular to fragments of the amyloid β(1-42) protein which are N-terminally truncated by from 7 to 23, preferably 9 to 21 and in particular 11 to 19, amino acids. These fragments correspond to the formula Aβ(x-42), where x is from 8 to 24, preferably 10 to 22 and in particular 12 to 20. According to the invention, the Aβ(x-42) fragments are therefore preferably to be selected from among the following fragments: Aβ(8-42), Aβ(9-42), Aβ(10-42), Aβ(11-42), Aβ(12-42), Aβ(13-42), Aβ(14-42), Aβ(15-42), Aβ(16-42), Aβ(17-42), Aβ(18-42), Aβ(19-42), Aβ(20-42), Aβ(21-42), Aβ(22-42), Aβ(23-42) and Aβ(24-42). Special fragments are the amyloid β(20-42) fragment obtainable by the action of thermolysin and the amyloid β(12-42) fragment obtainable by the action of GluC endoproteinase.

Derivatives of the invention are also those forms which are derived from an amyloid β(1-42) protein which has 1 or 2 further C-terminal amino acids. Examples thereof thus include oligomers of the Aβ(1-43) protein or derivatives thereof corresponding to the comments above.

The inventive method of preparing the oligomers may essentially comprise three steps, the first of which is optional but advantageous, the second step is absolutely required for preparation of the oligomers A and B and the third step serves to prepare the oligomers B of the invention.

Step 1 relates to unfolding of the protein. For this purpose, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, preferably in concentrated form, in suitable organic solvents miscible with aqueous buffers, such as, for example, dimethyl sulfoxide (DMSO), results in a suspension of the at least partially unfolded protein, which can be used in step 2 of the method of the invention. If required, the stock suspension may be stored at low temperature, for example at about −20° C., for an interim period.

Alternatively to step 1 above, the protein may be taken up in slightly acidic, preferably aqueous, solution, for example an about 10 mM aqueous HCl solution. After an incubation time of usually a few minutes, insoluble components are removed by centrifugation. A few minutes at 10 000 g is expedient. These method steps are preferably carried out at room temperature, i.e. a temperature in the range from 20 to 30° C. The supernatant obtained after centrifugation contains the amyloid β(1-42) protein and may be stored at low temperature, for example at about −20° C., for an interim period.

Step 2 relates to oligomerization of the protein to give the oligomers A. For this purpose, a detergent is allowed to act on the, optionally, at least partially unfolded protein until sufficient oligomer A has been produced.

Preference is given to using ionic detergents, in particular anionic detergents.

According to a particular embodiment, a detergent of the formula (I):

R—X, is used, in which
the radical R is unbranched or branched alkyl having from 6 to 20 and preferably 10 to 14 carbon atoms or unbranched or branched alkenyl having from 6 to 20 and preferably 10 to 14 carbon atoms,
the radical X is an acidic group or salt thereof, with X being preferably selected from among —COO$^-$M$^+$, —SO$_3^-$M$^+$, and especially
—OSO$_3^-$M$^+$ and M$^+$ is a hydrogen cation or an inorganic or organic cation preferably selected from alkali metal and alkaline earth metal cations and ammonium cations.

Advantageous are detergents of the formula (I), in which R is unbranched alkyl of which alk-1-yl radicals must be mentioned in particular. Particular preference is given to sodium dodecyl sulfate (SDS). Lauric acid and oleic acid can also be used advantageously. The sodium salt of the detergent lauroylsarcosin (also known as sarkosyl NL-30 or Gardol®) is also particularly advantageous.

The time of detergent action in particular depends on whether—and if yes, to what extent—the protein subjected to oligomerization has unfolded. If, according to step 1, the protein has been treated beforehand with a hydrogen bond-breaking agent, i.e. in particular with hexafluoroisopropanol, times of action in the range of a few hours, advantageously from about 1 to 20 and in particular from about 2 to 10 hours, are sufficient when the temperature of action is about 20 to 50° C. and in particular about 35 to 40° C. If a less unfolded or an essentially not unfolded protein is the starting point, correspondingly longer times of action are expedient. If the amyloid β(1-42) protein has been pretreated, for example, according to the procedure indicated above as an alternative to step 1 or said protein is directly introduced to step 2, times of action in the range from about 5 to 30 hours and in particular from about 10 to 20 hours are sufficient when the temperature of action is about 20 to 50° C. and in particular about 35 to 40° C. After incubation, insoluble components are advantageously removed by centrifugation. A few minutes at 10 000 g is expedient.

The detergent concentration to be chosen depends on the detergent used. If SDS is used, a concentration in the range from 0.01 to 1% by weight, preferably from 0.05 to 0.5% by weight, for example of about 0.2% by weight, proves expedient. If lauric acid or oleic acid are used, somewhat higher concentrations are expedient, for example in a range from 0.05 to 2% by weight, preferably from 0.1 to 0.5% by weight, for example of about 0.5% by weight.

The detergent action should take place at a salt concentration approximately in the physiological range. Thus, in particular NaCl concentrations in the range from 50 to 500 mM, preferably from 100 to 200 mM and particularly at about 140 mM are expedient.

The resulting solution containing the oligomers A, i.e. in particular oligomers A1 and/or A2, can be stored at low temperature, for example at about −20° C., for an interim period. Said solution may be subjected as such to the use of the invention or to further reaction to give the oligomers B, or further work-up or purification steps follow first which achieve in particular further concentration of at least one of the oligomers A of the invention. In particular, it is possible to remove the oligomers of the invention by means of chromatographic methods from other protein components present in the solution and in particular from those derived from the amyloid β(1-42) protein. Particularly suitable for this purpose are affinity chromatography methods which may employ, for example, specific antibodies, i.e. in particular also the oligomer-specific antibodies of the invention.

Step 3 relates to oligomerization to give the oligomers B. Preferably, a composition containing oligomer A is chosen as a reactant for this step. In this respect, the oligomers A are, according to the invention, important intermediates for the preparation of oligomers B. If said composition is from step 2, it regularly contains detergent and a salt concentration in the physiological range. It is then expedient to reduce detergent action and salt concentration. This may be carried out by reducing the concentration of detergent and salt, for example, by diluting, expediently with water or a buffer of lower salt concentration, for example Tris-HCl, pH 7.3. Dilution factors in the range from about 2 to 10, advantageously in the range from about 3 to 8 and in particular of about 4, have proved suitable. The reduction in detergent action may also be achieved by adding substances which can neutralize said detergent action. Examples of these include substances capable of complexing the detergents, like substances capable of stabilizing cells in the course of purification and extraction measures, for example particular EO/PO block copolymers, in particular the block copolymer under the trade name Pluronic® F 68. Alkoxylated and, in particular, ethoxylated alkyl phenols such as the ethoxylated t-octylphenols of the Triton® X series, in particular Triton® X100, 3-(3-cholamidopropyldimethylammonio)-1-propanesulfonate (CHAPS®) or alkoxylated and, in particular, ethoxylated sorbitan fatty esters such as those of the Tween® series, in particular Tween® 20, in concentration ranges around or above the particular critical micelle concentration.

Subsequently, the solution is incubated until sufficient oligomer B has been produced. Times of action in the range of several hours, preferably in the range from about 10 to 30 hours and in particular in the range from about 15 to 25 hours, are sufficient when the temperature of action is about 20 to 50° C. and in particular about 35 to 40° C. The solution may then be concentrated and possible residues may be removed by centrifugation. Here too, a few minutes at 10 000 g proves expedient. The supernatant obtained after centrifugation contains oligomers B.

The resulting solution containing the oligomers B, i.e. in particular the oligomers B1 and/or B2, may be stored at low temperature, for example at about −80° C., for an interim period. Said solution may be subjected as such to the use of the invention or further work-up or purification steps may follow first. Regarding this, reference is made to the comments above on corresponding measures in connection with the oligomers A.

Further work-up or purification steps may also be carried out for the purpose of essentially completely removing the detergent used for preparing the oligomers. For example, the oligomers B may first be precipitated from the detergent-containing solution, isolated and redissolved in detergent-free medium. Measures for precipitating proteins are sufficiently known to the skilled worker. According to the invention, the addition of aqueous-methanolic acetic acid has proved expedient. Without being bound to a particular mechanism, the detergent or variation of detergent and salt concentrations seems to put the protein in defined soluble forms which clearly differ from the protein starting form dissolved in aqueous physiological buffers, as can be detected, for example, by means of denaturing or native gel electrophoresis or gel permeation chromatography. This is astonishing, since detergents are normally capable of disaggregating, i.e. disassembling to subunits, protein aggregates, whereas, according to the invention, defined oligomers are obtained starting from a monomer prone to aggregation.

Derivatives of oligomers of the invention are expediently prepared by carrying out the above-described method of the invention on already appropriately derivatized amyloid β(1-42) protein. Alternatively, it is also possible to derivatize the oligomer but this should not alter the structure of said oligomer. Suitable protein-chemical measures are known to the skilled worker.

Crosslinking of oligomers of the invention or derivatives thereof may be carried out in a manner known per se. If, for example, glutardialdehyde is used as crosslinker, a solution resulting from method step 2 or 3 of the invention can be treated with a glutardialdehyde solution. After a few hours at room temperature, the oligomers will have reacted with the glutardialdehyde. The reaction may then be stopped in a manner known per se by reacting the excess glutardialdehyde with reagents generally known for this purpose, such as ethanolamine. Depending on whether oligomers A or B of the invention are crosslinked, a solution of crosslinked oligomers of the invention referred to as A-CL and B-CL, respectively, is obtained.

It is possible, in particular for the optionally crosslinked oligomers B or derivatives thereof, following the synthesis thereof, to increase again the salt concentration, without impairing the stability of said oligomers. This is important with regard to the use of said oligomers, for example in the case that for the use physiological conditions are expedient (cellular applications, in vivo applications).

Oligomers of fragments of the amyloid β(1-42) protein may be prepared in principle either starting from corresponding monomer fragments by oligomerization or starting from oligomers of said amyloid β(1-42) protein by proteolysis. Thus, according to the second method variant, a solution resulting from method steps 2 or 3 of the invention can be treated with protease. When the desired degree of proteolysis is reached, the protease is inactivated in a generally known manner. The resulting oligomers may then be isolated following the procedures already described herein and, if required, processed further by further work-up and purification steps.

The oligomers of the invention and the compositions comprising them are distinguished by their homogeneity and stability. They are soluble in physiological media, for example physiological saline, and differ from fibrillar forms by their rather globular appearance. They have the advantage of having a spatial structure which is distinctly different from other Aβ(1-42) forms, in particular the monomer, nontoxic oligomers, the Aβ(1-42)-comprising precursor molecule APP, protofibrils and fibrils. They are therefore particularly suitable for generating specific antibodies both in vivo and in vitro and make possible, for example, a specific active immunization. In this connection, it may be crucial to use for immunization only those oligomers which bring on the disease. Other forms of Aβ(1-42), such as the monomeric molecule or smaller oligomers, may be necessary for important signal functions in the organism. Likewise, removal of the fibrillar depositions which are presumably important for cell lining may damage the organism.

In the same way, it is possible to implement possible therapies using the homogeneous oligomers of the invention and compositions containing said oligomers, such as passive immunization, the use of destabilizers of the oligomeric forms and the use of receptor (partial) agonists or antagonists. Thus a homogeneous oligomer preparation makes also possible a specific production of polyclonal or monoclonal antibodies for passive immunization. It is also possible to find receptor molecules or signal molecules which are relevant to the disease and which are influenced by said oligomeric form by using the oligomers of the invention and compositions containing these.

Owing to their involvement in amyloid β protein-associated physiological processes, the oligomers of the invention have diagnostic and therapeutic value. Thus the present invention relates to the use of oligomers of the invention and of derivatives thereof, optionally in the form of a corresponding composition, in diagnostic in vitro and in vivo detection methods.

Amyloid β protein-associated physiological processes include those associated with depositions of amyloid proteins (amyloidoses). These include both those processes which result in structural modifications of nerve tissue and are important, for example, in Alzheimer's disease and Down's syndrome and those processes which affect other tissues, such as amyloid microangiopathies, for example congophilic amyloid angiopathy (CAA).

The present invention further relates to the use of oligomers of the invention and of derivatives thereof, optionally in the form of a corresponding composition, for generating oligomer-specific antibodies.

Here, the inventive oligomers based on truncated forms of the Aβ(1-42) protein are of particular importance: due to the missing N terminus, they can generate a distinctly more selective immune response than the Aβ(1-42) protein. While the highly immunogenic N terminus in the classical Aβ(1-42) protein predominantly produces antibodies which are specific for this region of the molecule, for example the antibodies 6E10 (F. Signet) and BAM-10 (Sigma, St. Louis) which, according to the manufacturers' information, are directed against the N terminus (6E10: Aβ(1-17) and BAM-10 Aβ(1-12)), the antibodies obtainable using the oligomers of the invention based on truncated Aβ(1-42) forms recognize oligomer-specific regions, thereby achieving a selectivity compared to other Aβ(1-42) forms. This advantage may be utilized in particular for active vaccination, since the more selective immune response resulting after vaccination (versus APP, monomeric forms, protofibrils, fibrils, plaques) also entails fewer side effects (e.g. brain hemorrhages, impairment of physiological neurotrophic activity of the in situ monomeric form). Superior production and selection of, in particular, monoclonal antibodies for passive immunization, i.e. an antibody therapy, are also possible.

One aspect of this use is the generation of oligomer-specific antibodies within the framework of a therapy.

The present invention therefore further relates to the use of an oligomer of the invention or of a derivative thereof in the therapeutic field, in particular as vaccine.

Such a vaccine is usually a pharmaceutical composition which comprises at least one oligomer of the invention and/or at least one derivative thereof of the invention. For this purpose, it is possible to use in particular any of the compositions of the invention which include two or more oligomers or a combination of different compositions. Thus it is possible to carry out a vaccination using in particular the oligomers B, i.e. B1 and B2, or derivatives thereof. The composition may further comprise a physiologically suitable carrier and, optionally, further excipients, for example immunostimulants.

While in principle any suitable carriers may be chosen, the type of carrier usually depends on the route of administration. Thus the vaccines of the invention may be formulated in particular in a form suitable for parenteral, for example intravenous, intramuscular and subcutaneous administration. In these cases, the carrier preferably includes water, saline, alcohol, a fat, a wax and/or a buffer.

It is possible to use any of a multiplicity of immunostimulants in the vaccines of the invention. For example, an adjuvant may be included. Most adjuvants contain a substance which ought to protect the antigen from rapid catabolism, such as aluminum hydroxide or a mineral oil, and also a protein derived from lipid A, *Bortadella pertussis* or *Mycobacterium tuberculosis*. Suitable adjuvants are usually commercially available, for example complete or incomplete Freund's adjuvant; AS-2; aluminum salts such as aluminum hydroxide (as gel, where appropriate) or aluminum phosphate; calcium salts, iron salts or zinc salts; an insoluble suspension of acylated tyrosine; acylated sugars; cationically or anionically derivatized polysaccharides; polyphosphazenes; biologically degradable microspheres; monophosphoryl lipid A. Cytokines such as GM-CSF or Interleukin-2, -7 or -12 may likewise be used as adjuvants.

The present invention furthermore relates to a method of producing antibodies, which comprises
i) immunizing a host with at least one oligomer of the invention, derivative thereof or composition; and
ii) obtaining an antibody-containing host serum produced as a response to said immunization.

According to a particular embodiment of the method of producing the antibodies, the immunization is carried out by administering immunization cocktails comprising mixtures of various oligomers or oligomer derivatives of the invention. In particular, it may be expedient to administer in the course of said method a plurality of immunization cocktails whose oligomer composition differs.

If the oligomers or oligomer derivatives to be used are not or only weakly immunogenic, their immunogenicity may be increased by coupling them to carriers, preferably to a carrier protein such as keyhole limpet hemocyanin (KLH), Limulus polyphenus hemocyanin (LPH), bovine serum albumin (BSA) or ovalbumin (OVA). For this purpose, there are a number of commonly known possible couplings available to the skilled worker. A possible expedient example is the reaction with glutardialdehyde, for example by incubating the oligomer or oligomer mixture with a suitable peptide or peptide mixture in water or an aqueous solvent. This reaction may conveniently be carried out at ambient temperature, i.e. usually room temperature. However, it may also be expedient to reduce or slightly increase the temperature. The reaction usually produces the desired result within a few hours, a reaction time of 2 h being within the usual range, for example. The glutardialdehyde concentration is usually in the ppm to % range, expediently from 10 ppm up to 1%, preferably from 10 ppm to 0.5%. Optimization of the reaction parameters is within the artisan's skills and should take into account that the oligomers A and B or oligomer derivatives are stable under the chosen reaction conditions.

The immunization cocktails are prepared by first combining the components to be used. It is of advantage to incubate the resulting component mixture initially. This is conveniently carried out at ambient temperature, i.e. usually at room temperature. However, it may be expedient to cool or slightly heat said mixture. The incubation period is usually from a few minutes to a few hours, with an incubation time of 1 h having proved advantageous.

Immunization cocktails contain, in addition to the antigen, usually further excipients, in particular adjuvants commonly used for immunization, for example Freund's adjuvant. More specifically, complete Freund's adjuvant is used for the first immunization, whereas any further immunizations are carried out with incomplete Freund's adjuvant. The immunization cocktail is prepared by adding the antigen (immunogen), preferably in the form of the above-described component mixture, to the excipient(s), with the antigen usually being emulsified.

Suitable hosts are in particular rodents or else rabbits. These or other suitable hosts are injected with the immunization cocktails, preferably subcutaneously. The antibody titers may be determined using an immunoassay, for example competitively using a sheep antiserum directed against host IgG and a labeled oligomer. Thus it may be decided toward the end of immunization whether a particular host is suitable for producing antibodies. If, for example, four immunizations are carried out, it is possible to determine the antibody titer after the third immunization and then to obtain antibodies from animals having a sufficient antibody titer.

The antibodies produced are preferably obtained by taking blood from the hosts over a period of several weeks or months. Finally, the host can be bled. Serum containing the desired antibodies may be obtained from the blood obtained in a manner known per se. The whole serum thus obtained may, if required, be further purified by the skilled worker in order to concentrate the antibody fraction present therein and in particular the oligomer-recognizing antibodies.

According to a particular embodiment of this method, at least one antibody of the serum is selected, which antibody specifically recognizes the oligomer used as immunogen or a derivative thereof or at least one oligomer or derivative thereof present in the composition used as immunogen. In this context, specificity means a higher binding affinity of the antibody for the immunogen than for other, in particular related proteins, especially in comparison with monomeric amyloid β(1-42) protein and also with oligomeric or multimeric amyloid β(1-42) protein aggregates having a higher molecular weight than the oligomers of the invention. It is also possible to obtain in this manner monoclonal oligomer-specific antibodies. To this end, however, preference is given to removing from the hosts spleen tissue and, starting from the thus obtained spleen lymphocytes, to establish in the usual manner hybridomas which produce the monoclonal antibodies.

Detailed Description of Antibody Production

B lymphocytes which, in totality, contain an antibody repertoire composed of hundreds of millions of different antibody specificities are part of the mammalian immune system. A normal immune response to a particular antigen means selection of one or more antibodies of said repertoire which specifically bind to said antigen, and the success of an immune response is based at least partially on the ability of said antibodies to specifically recognize (and ultimately to eliminate) the stimulating antigen and to ignore other molecules in the environment of said antibodies.

The usefulness of antibodies which specifically recognize one particular target antigen has led to the development of monoclonal antibody technology. Standardized hybridoma technology now allows the production of antibodies with a single specificity for an antigen of interest. More recently, recombinant antibody techniques such as in-vitro screening of antibody libraries have been developed. These techniques likewise allow antibodies having a single specificity for an antigen of interest to be produced.

In the method of the invention, the antigen of interest may be allowed to act on the antibody repertoire either in vivo or in vitro.

According to one embodiment, the antigen is allowed to act on the repertoire by immunizing an animal in vivo with said antigen. This in-vivo approach may furthermore comprise establishing from the lymphocytes of an animal a number of hybridomas and selecting a hybridoma which secretes an antibody specifically binding to said antigen. The animal to be immunized may be, for example, a mouse, rat, rabbit, chicken, camelid or sheep or may be a transgenic version of any of the animals mentioned above, for example a transgenic mouse with human immunoglobulin genes, which produces human antibodies after an antigenic stimulus. Other types of animals which may be immunized include mice with severe combined immunodeficiency (SCID) which have been reconstituted with human peripheral mononuclear blood cells (chimeric hu-PBMC SCID mice) or with lymphoid cells or precursors thereof, as well as mice which have been treated with a lethal total body irradiation, then protected against radiation with bone marrow cells from a mouse with severe combined immunodeficiency (SCID) and subsequently transplanted with functional human lymphocytes (the "Trimera" system). Another type of an animal to be immunized is an animal (e.g. a mouse) in whose genome an endogenous gene encoding the antigen of interest has been switched off (knocked out), for example by homologous recombination, so that, after immunization with the antigen, said animal recognizes said antigen as foreign. It is obvious to the skilled worker that the polyclonal or monoclonal antibodies produced by this method are characterized and selected by using known screening methods which include, but are not limited to, ELISA techniques.

According to another embodiment, the antigen is allowed to act on the antibody repertoire in vitro by screening a recombinant antibody library with said antigen. The recombinant antibody library may be expressed, for example, on the surface of bacteriophages or on the surface of yeast cells or on the surface of bacterial cells. In a variety of embodiments, the recombinant antibody library is an scFv library or an Fab library, for example. According to another embodiment, antibody libraries are expressed as RNA-protein fusions.

Another approach to producing antibodies of the invention comprises a combination of in vivo and in vitro approaches. For example, the antigen may be allowed to act on the antibody repertoire by immunizing an animal in vivo with said antigen and then screening in vitro with said antigen a recombinant antibody library prepared from lymphoid cells of said animal or a single domain antibody library (e.g. containing heavy and/or light chains). According to another approach, the antigen is allowed to act on the antibody repertoire by immunizing an animal in vivo with said antigen and then subjecting a recombinant antibody library or single domain library produced from lymphoid cells of said animal to affinity maturation. According to another approach, the antigen is allowed to act on the antibody repertoire by immunizing an animal in vivo with said antigen, then selecting individual antibody-producing cells secreting an antibody of interest and obtaining from said selected cells cDNAs for the variable region of the heavy and light chains (e.g. by means of PCR) and expressing said variable regions of the heavy and light chains in mammalian host cells in vitro (this being referred to as selected lymphocyte antibody method or SLAM), thereby being able to further select and manipulate the selected antibody gene sequences. Moreover, monoclonal antibodies may be selected by expression cloning by expressing the antibody genes for the heavy and light chains in mammalian cells and selecting those mammalian cells which secrete an antibody having the desired binding affinity.

Accordingly, one aspect of the present invention is to provide defined antigens for screening and counter screening. Thus it is possible, according to the invention, to select those polyclonal and monoclonal antibodies which bind an oligomer of the invention or derivative thereof but not other forms of the Aβ(1-42) protein, APP, amyloid fibrils or amyloid plaques and a number of other nonrelated antigens and tissues.

It is sufficiently known to the skilled worker that antibody selections are based on well-defined antigens. In contrast, less well-defined antigens are not selective enough when used. In short, the acting and selecting in vitro is similar to affinity chromatography, with "ligands" for the desired antigen being removed from those which bind the antigen with insufficient affinity. The degree of concentration of the desired antibodies from the huge pool of other antibodies is therefore a direct consequence of the quality of the antigen. Surprisingly, the oligomers of the invention and derivatives thereof are antigens which can be used to concentrate suitable, relevant and selective antibodies and efficiently remove them from antibodies which recognize other forms associated with the Aβ(1-42) protein and other nonrelated antigens.

The methods of the invention for producing antibodies can be used to produce various types of antibodies. These include essentially human antibodies, chimeric antibodies, humanized antibodies and CDR graft antibodies and also antigen-binding moieties thereof.

Methods of producing antibodies of the invention are described below. A distinction is made here between in-vivo approaches, in-vitro approaches or a combination of both.

In-Vivo Approaches

Starting from the in-vivo generated antibody-producing cells, monoclonal antibodies may be produced by means of standardized techniques such as the hybridoma technique originally described by Kohler and Milstein (1975, *Nature* 256:495-497) (see also Brown et al. (1981) *J. Immunol.* 127: 539-46; Brown et al. (1980) *J Biol Chem* 255:4980-83; Yeh et al. (1976) *PNAS* 76:2927-31; and Yeh et al. (1982) *Int. J. Cancer* 29:269-75). The technology of producing monoclonal antibody hybridomas is sufficiently known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortalized cell line (typically a myeloma) is fused with lymphocytes (typically splenocytes or lymph node cells or peripheral blood lymphocytes) of a mammal immunized with the oligomer of the invention or derivative thereof, and the culture supernatants of the resulting hybridoma cells are screened in order to identify a hybridoma which produces a monoclonal antibody with specificity for the oligomer of the invention or for a derivative thereof. Any of the many well known protocols for fusing lymphocytes and immortalized cell lines can be applied for this purpose (see also G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the skilled worker will appreciate that there are diverse variations of such methods, which are likewise useful. Typically, the immortalized cell line (e.g. a myeloma cell line) is derived from the same mammalian species as the lymphocytes. For example, murine hybridomas may be established by fusing lymphocytes from a mouse immunized with an immunogenic preparation of the invention with an immortalized mouse cell line. Preferred immortalized cell lines are mouse myeloma cell lines which are sensitive to culture medium containing hypoxanthine, aminopterin and thymidine (HAT medium). Any of a number of myeloma cell lines may be used standardwise as fusion partner, for example the P3-NS1/1-Ag-4-1, P3-x63-Ag8.653 or Sp2/O-Ag14 myeloma lines. These myeloma cell lines are available from the American Type Culture Collection (ATCC), Rockville, Md. Typically, HAT-sensitive mouse myeloma cells are fused to mouse splenocytes using polyethylene glycol (PEG). Hybridoma cells resulting from the fusion are then selected using HAT medium, thereby killing unfused and unproductively fused myeloma cells (unfused splenocytes die after several days because they are not transformed). Hybridoma cells producing monoclonal antibodies which specifically recognize the oligomer of the invention or a derivative thereof are identified by screening the hybridoma culture supernatants for such antibodies, for example by using a standard ELISA assay in order to select those antibodies which can specifically bind the oligomer of the invention or a derivative thereof.

Depending on the type of the desired antibody, various host animals may be used for in-vivo immunization. A host expressing itself an endogenous version of the antigen of interest may be used. Alternatively, it is possible to use a host which has been made deficient in an endogenous version of the antigen of interest. For example, mice which had been made deficient in a particular endogenous protein via homologous recombination at the corresponding endogenous gene (i.e. knockout mice) have been shown to generate a humoral response to the protein with which they have been immunized and therefore to be able to be used for production of high-affinity monoclonal antibodies to the protein (see, for example, Roes, J. et al. (1995) *J. Immunol. Methods* 183:231-237; Lunn, M. P. et al. (2000) *J. Neurochem.* 75:404-412).

A multiplicity of nonhuman mammals are suitable hosts for antibody production in order to produce nonhuman antibodies to the oligomer of the invention or to a derivative thereof. They include mice, rats, chickens, camelids, rabbits and goats (and knockout versions thereof), although preference is given to mice for the production of hybridoma. Furthermore, a nonhuman host animal expressing a human antibody repertoire may be used for producing essentially human antibodies to a human antigen with dual specificity. Nonhuman animals of this kind include transgenic animals (e.g. mice) bearing human immunoglobulin transgenes (chimeric hu-PBMC SCID mice) and human/mouse irradiation chimeras which are described in more detail below.

According to one embodiment, the animal immunized with an oligomer of the invention or derivative thereof is a nonhuman mammal, preferably a mouse, which is transgenic due to human immunoglobulin genes so that said nonhuman mammal makes human antibodies upon antigenic stimulation. Typically, immunoglobulin transgenes for heavy and light chains with human germ line configuration are introduced into such animals which have been altered such that their endogenous heavy and light chain loci are inactive. If such animals are stimulated with antigen (e.g. with a human antigen), antibodies derived from the human immunoglobulin sequences (human antibodies) are produced. It is possible to make from the lymphocytes of such animals human monoclonal antibodies by means of standardized hybridoma technology. For a further description of transgenic mice with human immunoglobulins and their use in the production of human antibodies, see, for example, U.S. Pat. No. 5,939,598, WO 96/33735, WO 96/34096, WO 98/24893 and WO 99/53049 (Abgenix Inc.), and U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, U.S. Pat. No. 5,814,318, U.S. Pat. No. 5,877,397 and WO 99/45962 (Genpharm Inc.); see also MacQuitty, J. J. and Kay, R. M. (1992) *Science* 257:1188; Taylor, L. D. et al. (1992) *Nucleic Acids Res.* 20:6287-6295; Lonberg, N. et al. (1994) *Nature* 368:856-859; Lonberg, N. and Huszar, D. (1995) *Int. Rev. Immunol.* 13:65-93; Harding, F. A. and Lonberg, N.

(1995) *Ann. N.Y. Acad. Sci.* 764:536-546; Fishwild, D. M. et al. (1996) *Nature Biotechnology* 14:845-851; Mendez, M. J. et al. (1997) *Nature Genetics* 15:146-156; Green, L. L. and Jakobovits, A. (1998) *J. Exp. Med.* 188:483-495; Green, L. L. (1999) *J. Immunol. Methods* 231:11-23; Yang, X. D. et al., (1999) *J. Leukoc. Biol.* 66:401-410; Gallo, M. L. et al. (2000) *Eur. J. Immunol.* 30:534-540.

According to another embodiment, the animal which is immunized with an oligomer of the invention or a derivative thereof may be a mouse with severe combined immunodeficiency (SCID), which has been reconstituted with human peripheral mononuclear blood cells or lymphoid cells or precursors thereof. Such mice which are referred to as chimeric hu-PBMC SCID mice produce human immunoglobulin responses upon antigenic stimulation, as has been proved. For a further description of these mice and of their use for generating antibodies, see, for example, Leader, K. A. et al. (1992) *Immunology* 76:229-234; Bombil, F. et al. (1996) *Immunobiol.* 195:360-375; Murphy, W. J. et al. (1996) *Semin. Immunol.* 8:233-241; Herz, U. et al. (1997) *Int. Arch. Allergy Immunol.* 113:150-152; Albert, S. E. et al. (1997) *J. Immunol.* 159:1393-1403; Nguyen, H. et al. (1997) *Microbiol. Immunol.* 41:901-907; Arai, K. et al., (1998) *J. Immunol. Methods* 217:79-85; Yoshinari, K. and Arai, K. (1998) *Hybridoma* 17:41-45; Hutchins, W. A. et al. (1999) *Hybridoma* 18:121-129; Murphy, W. J. et al. (1999) *Clin. Immunol.* 90:22-27; Smithson, S. L. et al. (1999) *Mol. Immunol.* 36:113-124; Chamat, S. et al. (1999) *J. Infect. Diseases* 180:268-277; and Heard, C. et al. (1999) *Molec. Med.* 5:35-45.

According to another embodiment, the animal which is immunized with an oligomer of the invention or a derivative thereof is a mouse which has been treated with a lethal total body irradiation, then protected from radiation with bone marrow cells from mice with severe combined immunodeficiency (SCID) and subsequently transplanted with functional human lymphocytes. This type of chimera, referred to as the Trimera system, is used in order to produce human monoclonal antibodies by immunizing said mice with the antigen of interest and then producing monoclonal antibodies by using standardized hybridoma technology. For a further description of these mice and of their use for generating antibodies, see, for example, Eren, R. et al., (1998) *Immunology* 93:154-161; Reisner, Y. and Dagan, S. (1998) *Trends Biotechnol.* 16:242-246; Ilan, E. et al. (1999) *Hepatology* 29:553-562; and Bocher, W. O. et al. (1999) *Immunology* 96:634-641.

In-Vitro Approaches

As an alternative to producing antibodies of the invention by immunization and selection, antibodies of the invention may be identified and isolated by screening recombinant combinatorial immunoglobulin libraries with an oligomer of the invention or derivative thereof to thereby isolate immunoglobulin library members which specifically bind to said oligomer or derivative thereof. Kits for generating and screening display libraries are commercially available (e.g. the Pharmacia Recombinant Phage Antibody System, catalog No. 27-9400-01; and the Stratagene SurfZAP® Phage Display Kit, catalog No. 240612). In many embodiments, the display library is an scFv library or an Fab library. The phage display technique for screening recombinant antibody libraries has been adequately described. Examples of methods and compounds which can be used particularly advantageously for generating and screening antibody display libraries can be found, for example, in McCafferty et al. WO 92/01047, U.S. Pat. No. 5,969,108 and EP 589 877 (describes in particular scFv display), Ladner et al. U.S. Pat. No. 5,223,409, U.S. Pat. No. 5,403,484, U.S. Pat. No. 5,571,698, U.S. Pat. No. 5,837, 500 and EP 436 597 (describes pill fusion, for example); Dower et al. WO 91/17271, U.S. Pat. No. 5,427,908, U.S. Pat. No. 5,580,717 and EP 527 839 (describes in particular Fab display); Winter et al. International Publication WO 92/20791 and EP 368,684 (describes in particular the cloning of sequences for variable immunoglobulin domains); Griffiths et al. U.S. Pat. No. 5,885,793 and EP 589 877 (describes in particular isolation of human antibodies to human antigens by using recombinant libraries); Garrard et al. WO 92/09690 (describes in particular phage expression techniques); Knappik et al. WO 97/08320 (describes the human recombinant antibody library HuCal); Salfeld et al. WO 97/29131, (describes production of a recombinant human antibody to a human antigen (human tumor necrosis factor alpha) and also in-vitro affinity maturation of the recombinant antibody) and Salfeld et al. U.S. Provisional Application No. 60/126,603 and the patent applications based hereupon (likewise describes production of recombinant human antibodies to human antigen (human interleukin-12), and also in-vitro affinity maturation of the recombinant antibody).

Further descriptions of screenings of recombinant antibody libraries can be found in scientific publications such as Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al., (1993) *EMBO J.* 12:725-734; Hawkins et al. (1992) *J Mol Biol* 226:889-896; Clarkson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; Barbas et al. (1991) *PNAS* 88:7978-7982; McCafferty et al. *Nature* (1990) 348:552-554; and Knappik et al. (2000) *J. Mol. Biol.* 296:57-86.

As an alternative to using bacteriophage display systems, recombinant antibody libraries may be expressed on the surface of yeast cells or of bacterial cells. WO 99/36569 describes methods of preparing and screening libraries expressed on the surface of yeast cells. WO 98/49286 describes in more detail methods of preparing and screening libraries expressed on the surface of bacterial cells.

Once an antibody of interest of a combinatorial library has been identified, the DNAs encoding the light and heavy chains of said antibody are isolated by means of standardized molecular-biological techniques, for example by means of PCR amplification of DNA from the display package (e.g. the phage) which has been isolated during library screening. Nucleotide sequences of genes for light and heavy antibody chains, which may be used for preparing PCR primers, are known to the skilled worker. A multiplicity of such sequences are described, for example, in Kabat, E. A., et al. (1991) *Sequences of Proteins of Immunological Interest, Fifth Edition*, U.S. Department of Health and Human Services, NIH Publication No. 91-3242 and in the database of sequences of the human germ line VBASE.

An antibody or antibody moiety of the invention may be produced by recombinantly expressing the genes for light and heavy immunoglobulin chains in a host cell. In order to recombinantly express an antibody, a host cell is transfected with one or more recombinant expression vectors carrying DNA fragments encoding the light and heavy immunoglobulin chains of said antibody, thereby expressing the light and heavy chains in the host cell and secreting them preferably into the medium in which said host cells are cultured. The antibodies can be isolated from this medium. Standardized recombinant DNA methods are used in order to obtain genes for heavy and light antibody chains, to insert said genes into recombinant expression vectors and to introduce said vectors into host cells. Methods of this kind are described, for example, in Sambrook, Fritsch and Maniatis (eds.), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

Once DNA fragments encoding VH and VL segments of the antibody of interest are obtained, said DNA fragments may be further manipulated using standardized recombinant DNA techniques, for example in order to convert the genes for variable regions to genes for full length antibody chains, to genes for Fab fragments or to an scFv gene. These manipulations comprise linking a VL- or VH-encoding DNA fragment operatively to another DNA fragment encoding another protein, for example a constant antibody region or a flexible linker. The term "operatively linked" is to be understood here as meaning that the two DNA fragments are linked to one another in such a way that the amino acid sequences encoded by said two DNA fragments remain in frame.

The isolated DNA encoding the VH region may be converted to a gene for a full length heavy chain by operatively linking the VH-region encoding DNA with another DNA molecule encoding heavy chain constant regions (CH1, CH2 and CH3). The sequences of human heavy chain constant region genes are well known (see, for example, Kabat, E. A., et al. (1991) *Sequences of Proteins of Immunological Interest, Fifth Edition*, U.S. Department of Health and Human Services, NIH Publication No. 91-3242), and DNA fragments spanning said regions may be obtained by means of standardized PCR amplification. The heavy chain constant region may be a constant region from IgG1, IgG2, IgG3, IgG4, IgA, IgE, IgM or IgD, with preference being given to a constant region from IgG1 or IgG4. To obtain a gene for a heavy chain Fab fragment, the VH-encoding DNA may be operatively linked to another DNA molecule encoding merely the heavy chain constant region CH1.

The isolated DNA encoding the VL region may be converted to a gene for a full length light chain (and a gene for an Fab light chain) by operatively linking the VL-encoding DNA to another DNA molecule encoding the light chain constant region CL. The sequences of genes of the constant region of human light chain are well known (see Kabat, E. A., et al. (1991) *Sequences of Proteins of Immunological Interest, Fifth Edition*, U.S. Department of Health and Human Services, NIH Publication No. 91-3242), and DNA fragments spanning said regions may be obtained by means of standardized PCR amplification. The light chain constant region may be a constant kappa or lambda region, a constant kappa region being preferred.

In order to generate an scFv gene, the VH- and VL-encoding DNA fragments may be operatively linked to another fragment encoding a flexible linker, for example the amino acid sequence $(Gly_4\text{-}Ser)_3$ so that the VH and VL sequences are expressed as a continuous single-chain protein, with the VL and VH regions being linked to one another via said flexible linker (see Bird et al. (1988) *Science* 242:423-426; Huston et al. (1988) *Proc. Natl. Acad. Sci. USA* 85:5879-5883; McCafferty et al., *Nature* (1990) 348:552-554).

Single domain VH and VL with specificity for an oligomer of the invention or for a derivative thereof may be isolated from single domain libraries by the above-described methods. Two VH single-domain chains (with or without CH1) or two VL chains or a pair of one VH chain and one VL chain with the desired specificity may be used for removing oligomers of the invention or derivatives thereof from the body.

In order to express the recombinant antibodies or antibody moieties of the invention, the DNAs encoding partial or full length light and heavy chains may be inserted into expression vectors so as to operatively link the genes to transcriptional and translational control sequences. In this context, the term "operatively linked" is to be understood as meaning that an antibody gene is ligated in a vector in such a way that transcriptional and translational control sequences within the vector fulfill their intended function of regulating transcription and translation of said antibody gene.

The expression vector and the expression control sequences are chosen so as to be compatible with the expression host cell used. The gene for the antibody light chain and the gene for the antibody heavy chain may be inserted into separate vectors or both genes are inserted into the same expression vector, this being the usual case. The antibody genes are inserted into the expression vector by means of standardized methods (for example ligation of complementary restriction cleavage sites on the antibody gene fragment and the vector, or ligation of blunt ends, if no restriction cleavage sites are present). The expression vector may already carry sequences for antibody constant regions prior to insertion of the sequences for the light and heavy chains. For example, one approach is to convert the VH and VL sequences to full length antibody genes by inserting them into expression vectors already encoding the heavy and, respectively, light chain constant regions, thereby operatively linking the VH segment to the CH segment(s) within the vector and also operatively linking the VL segment to the CL segment within the vector. Additionally or alternatively, the recombinant expression vector may encode a signal peptide which facilitates secretion of the antibody chain from the host cell. The gene for said antibody chain may be cloned into the vector, thereby linking the signal peptide in frame to the N terminus of the gene for the antibody chain. The signal peptide may be an immuno-globulin signal peptide or a heterologous signal peptide (i.e. a signal peptide from a non-immunoglobulin protein). In addition to the genes for the antibody chain, the expression vectors of the invention may have regulatory sequences controlling expression of the genes for the antibody chain in a host cell. The term "regulatory sequence" is intended to include promoters, enhancers and further expression control elements (e.g. polyadenylation signals) which control transcription or translation of the genes for the antibody chain. Regulatory sequences of this kind are described, for example, in Goeddel; *Gene Expression Technology: Methods in Enzymology* 185, Academic Press, San Diego, Calif. (1990). The skilled worker will appreciate that the expression vector design which includes selection of regulatory sequences may depend on factors such as the choice of host cell to be transformed, the desired strength of expression of the protein, etc. Preferred regulatory sequences for expression in mammalian host cells include viral elements resulting in a strong protein expression in mammalian cells, such as promoters and/or enhancers derived from cytomegalovirus (CMV) (such as the CMV promoter/enhancer), simian virus 40 (SV40) (such as the SV40 promoter/enhancer), adenovirus (e.g. the adenovirus major late promoter (Ad-MLP)) and polyoma. For a further description of viral regulatory elements and sequences thereof, see, for example, U.S. Pat. No. 5,168,062 to Stinski, U.S. Pat. No. 4,510,245 to Bell et al. and U.S. Pat. No. 4,968,615 to Schaffner et al.

Apart from the genes for the antibody chain and the regulatory sequences, the recombinant expression vectors of the invention may have additional sequences such as those which regulate replication of the vector in host cells (e.g. origins of replication) and selectable marker genes. The selectable marker genes facilitate the selection of host cells into which the vector has been introduced (see, for example, U.S. Pat.

Nos. 4,399,216, 4,634,665 and 5,179,017, all to Axel et al.). For example, it is common for the selectable marker gene to render a host cell into which the vector has been inserted resistant to drugs such as G418, hygromycin or methotrexate. Preferred selectable marker genes include the gene for dihydrofolate reductase (DHFR) (for use in dhfr host cells with methotrexate selection/amplification) and the neo gene (for G418 selection).

For expression of the light and heavy chains, the expression vector(s) encoding said heavy and light chains is(are) transfected into a host cell by means of standardized techniques. The various forms of the term "transfection" are intended to comprise a multiplicity of techniques customarily used for introducing exogenous DNA into a prokaryotic or eukaryotic host cell, for example electroporation, calcium phosphate precipitation, DEAE-dextran transfection, and the like. Although it is theoretically possible to express the antibodies of the invention either in prokaryotic or eukaryotic host cells, preference is given to expressing the antibodies in eukaryotic cells and, in particular, in mammalian host cells, since the probability of a correctly folded and immunologically active antibody being assembled and secreted is higher in such eukaryotic cells and in particular mammalian cells than in prokaryotic cells. Prokaryotic expression of antibody genes has been reported as being ineffective for production of high yields of active antibody (Boss, M. A. and Wood, C. R. (1985) *Immunology Today* 6:12-13).

Preferred mammalian host cells for expressing recombinant antibodies of the invention include CHO cells (including dhfr CHO cells described in Urlaub and Chasin, (1980) *Proc. Natl. Acad. Sci. USA* 77:4216-4220, which are used together with a DHFR-selectable marker, as described, for example, in R. J. Kaufman and P. A. Sharp (1982) *Mol. Biol.* 159:601-621), NS0 myeloma cells, COS cells and SP2 cells. When introducing recombinant expression vectors encoding the antibody genes into mammalian host cells, the antibodies are produced by culturing the host cells until the antibody is expressed in said host cells or, preferably, the antibody is secreted into the culture medium in which the host cells grow. The antibodies may be isolated from the culture medium by using standardized protein purification methods.

It is likewise possible to use host cells in order to produce moieties of intact antibodies, such as Fab fragments or scFv molecules. Variations of the above-described procedure are of course included in the invention. For example, it may be desirable to transfect a host cell with DNA encoding either the light chain or the heavy chain (but not both) of an antibody of the invention. If either light or heavy chains are present which are not required for binding of the antigen of interest, then the DNA encoding either such a light or such a heavy chain or both may be removed partially or completely by means of recombinant DNA technology. Molecules expressed by such truncated DNA molecules are likewise included in the antibodies of the invention. In addition, it is possible to produce bifunctional antibodies in which a heavy chain and a light chain are an antibody of the invention and the other heavy chain and the other light chain have specificity for an antigen different from the antigen of interest, by crosslinking an antibody of the invention to a second antibody by means of standardized chemical methods.

In a preferred system for recombinant expression of an antibody of the invention or an antigen-binding moiety thereof, a recombinant expression vector encoding both the antibody heavy chain and the antibody light chain is introduced into dhfr CHO cells by means of calcium phosphate-mediated transfection. Within the recombinant expression vector, the genes for the heavy and light antibody chains are in each case operatively linked to regulatory CMV enhancer/AdMLP-promoter elements in order to effect strong transcription of said genes. The recombinant expression vector also carries a DHFR gene which can be used for selecting CHO cells transfected with the vector by using methotrexate selection/amplification. The selected transformed host cells are cultured so that the heavy and light antibody chains are expressed, and intact antibody is isolated from the culture medium. Standardized molecular-biological techniques are used in order to prepare the recombinant expression vector, to transfect the host cells, to select the transformants, to culture said host cells, and to obtain the antibody from the culture medium. Thus the invention relates to a method of synthesizing a recombinant antibody of the invention by culturing a host cell of the invention in a suitable culture medium until a recombinant antibody of the invention has been synthesized. The method may furthermore comprise isolating said recombinant antibody from said culture medium.

As an alternative to screening recombinant antibody libraries by phage display, other methods known to the skilled worker may be used for screening large combinatorial libraries to identify the antibodies of the invention. In one type of an alternative expression system, the recombinant antibody library is expressed in the form of RNA-protein fusions, as described in WO 98/31700 to Szostak and Roberts, and in Roberts, R. W. and Szostak, J. W. (1997) *Proc. Natl. Acad. Sci. USA* 94:12297-12302. In this system, in-vitro translation of synthetic mRNAs carrying on their 3' end puromycin, a peptidyl acceptor antibiotic, generates a covalent fusion of an mRNA and the peptide or protein encoded by it. Thus a specific mRNA of a complex mixture of mRNAs (e.g. a combinatorial library) may be concentrated on the basis of the properties of the encoded peptide or protein (e.g. of the antibody or a moiety thereof), such as binding of said antibody or said moiety thereof to an oligomer of the invention or a derivative thereof. Nucleic acid sequences which encode antibodies or moieties thereof and which are obtained by screening of such libraries may be expressed by recombinant means in the above-described manner (e.g. in mammalian host cells) and may, in addition, be subjected to further affinity maturation by either screening in further rounds mRNA-peptide fusions, introducing mutations into the originally selected sequence(s), or using other methods of in-vitro affinity maturation of recombinant antibodies in the above-described manner.

Combinations of In-Vivo and In-Vitro Approaches

The antibodies of the invention may likewise be produced by using a combination of in-vivo and in-vitro approaches such as methods in which an oligomer of the invention or a derivative thereof is first allowed to act on an antibody repertoire in a host animal in vivo to stimulate production of oligomer- or derivative-binding antibodies and then further antibody selection and/or antibody maturation (i.e. optimization) are accomplished with the aid of one or more in-vitro techniques. According to one embodiment, a combined method of this kind may comprise firstly immunizing a non-human animal (e.g. a mouse, rat, rabbit, chicken, camelid, goat or a transgenic version thereof or a chimeric mouse) with said oligomer of the invention or derivative thereof to stimulate an antibody response to the antigen and then preparing and screening a phage display antibody library by using immunoglobulin sequences of lymphocytes which have been stimulated in vivo by the action of said oligomer or derivative. The first step of this combined procedure may be carried out in the manner described above in connection with the in-vivo approaches, while the second step of this procedure may be carried out in the manner described above in connection with the in-vitro approaches. Preferred methods of hyperimmunizing nonhuman animals with subsequent in-vitro screening of phage display libraries prepared from said stimulated lymphocytes include those described by BioSite Inc., see, for example, WO 98/47343, WO 91/17271, U.S. Pat. No. 5,427,908 and U.S. Pat. No. 5,580,717.

According to another embodiment, a combined method comprises firstly immunizing a nonhuman animal (e.g. a mouse, rat, rabbit, chicken, camelid, goat or a knockout and/or transgenic version thereof, or a chimeric mouse) with an oligomer of the invention or derivative thereof to stimulate an antibody response to said oligomer or derivative thereof and selecting the lymphocytes which produce the antibodies having the desired specificity by screening hybridomas (prepared, for example, from the immunized animals). The genes for the antibodies or single domain antibodies are isolated from the selected clones (by means of standardized cloning methods such as reverse transcriptase polymerase chain reaction) and subjected to in-vitro affinity maturation in order to improve thereby the binding properties of the selected antibody or the selected antibodies. The first step of this procedure may be conducted in the manner described above in connection with the in-vivo approaches, while the second step of this procedure may be conducted in the manner described above in connection with the in-vitro approaches, in particular by using methods of in-vitro affinity maturation, such as those described in WO 97/29131 and WO 00/56772.

In a further combined method, the recombinant antibodies are generated from individual isolated lymphocytes by using a procedure which is known to the skilled worker as selected lymphocyte antibody methods (SLAM) and which is described in U.S. Pat. No. 5,627,052, WO 92/02551 and Babcock, J. S. et al. (1996) *Proc. Natl. Acad. Sci. USA* 93:7843-7848. In this method, a nonhuman animal (e.g. a mouse, rat, rabbit, chicken, camelid, goat, or a transgenic version thereof, or a chimeric mouse) is firstly immunized in vivo with an oligomer of the invention or a derivative thereof to stimulate an immune response to said oligomer or derivative, and then individual cells secreting antibodies of interest are selected by using an antigen-specific hemolytic plaque assay. To this end, the oligomer or derivative thereof or structurally related molecules of interest may be coupled to sheep erythrocytes, using a linker such as biotin, thereby making it possible to identify individual cells secreting antibodies with suitable specificity by using the hemolytic plaque assay. Following the identification of cells secreting antibodies of interest, cDNAs for the variable regions of the light and heavy chains are obtained from the cells by reverse transcriptase PCR, and said variable regions may then be expressed in association with suitable immunoglobulin constant regions (e.g. human constant regions) in mammalian host cells such as COS or CHO cells. The host cells transfected with the amplified immunoglobulin sequences derived from in vivo-selected lymphocytes may then be subjected to further in-vitro analysis and in-vitro selection by spreading out the transfected cells, for example, in order to isolate cells expressing antibodies with the desired specificity. The amplified immunoglobulin sequences may furthermore be manipulated in vitro.

Analogously to the above-described procedures, it is also possible to prepare antibodies having specificity for an oligomer of the invention or derivative thereof and for structurally related synthetic molecules. This comprises
i) providing an antigen which comprises a structural feature shared by the oligomer of the invention or derivative thereof and the structurally related synthetic molecules;
ii) exposing an antibody repertoire to said antigen; and
iii) selecting from said repertoire an antibody which binds to two structurally related molecules, thereby obtaining the antibody having the desired specificity.

The present invention relates to the oligomer-specific antibodies obtainable by the above methods as well as to the use thereof for preparing a medicament for the treatment of amyloid β-associated dementing disorders or for preparing a composition for diagnosing amyloid β-associated dementing disorders.

The antibodies obtainable according to the invention include in particular antisera which can be obtained by the above methods. Said antisera may be whole sera, i.e. blood obtained from the host after removing the cellular and coagulable components, or fractions of said serum which contain in particular a concentrated immunoglobulin fraction and preferably a concentrated, oligomer-recognizing immunoglobulin fraction. Fractions of this kind may be obtained using the methods described above in connection with antibody purification.

The antisera of the invention are polyclonal, i.e. they contain antibodies of different specificity, usually of different classes and subclasses, normally all L-chain isotypes are represented and multiple protein epitopes are recognized.

When using various oligomers of the invention as immunogens, then the antisera of the invention are usually cross-reactive.

According to another aspect, the antibodies obtainable according to the invention also include monoclonal antibodies, in particular chimeric and humanized antibodies, and also oligomer-binding fragments thereof.

The present invention relates to proteins and in particular to antibodies binding to an oligomer of the invention or derivative thereof, i.e. antibodies having specificity for an oligomer of the invention or derivative thereof. The present invention also relates to moieties of said proteins or antibodies, in particular to antigen-binding moieties thereof, i.e. protein or antibody moieties binding to an oligomer of the invention or derivative thereof.

The antibody of the invention is preferably chosen so as to have particular binding kinetics (e.g. high affinity, low dissociation, low off rate, strong neutralizing activity) for the specific binding to an oligomer of the invention or a derivative thereof.

Thus preference is given to proteins and, in particular, antibodies having an affinity for the oligomer of the invention or derivative thereof in the range of $K_D=10^{-6}$-$10^{-12}$ M. Particular preference is given to high-affinity proteins and in particular antibodies binding with an affinity greater than $K_d=10^{-8}$ M, with an affinity greater than $K_d=10^{-9}$ M, with an affinity greater than $K_d=10^{-10}$ M or with an affinity greater than $K_d=10^{-11}$ M.

According to another aspect, preference is given to those proteins and, in particular, antibodies which bind other Aβ(1-42) forms, in particular monomeric Aβ(1-42) protein and/or monomeric Aβ(1-40) protein with comparatively lower affinity, in particular with lower affinity than $K_d=10^{-8}$ M.

Accordingly, preference is given according to the invention especially to those proteins and, in particular, antibodies which bind the oligomer or derivative thereof with higher affinity than monomeric Aβ(1-42) protein and/or monomeric Aβ(1-40) protein. Particular preference is given to affinity ratios of 10, 100 or 1000.

According to another aspect, the antibodies of the invention may be chosen so as to bind the oligomer or derivative thereof with a $k_{off}$ rate constant of 0.1 s$^{-1}$ or less. Increasing preference is given to rate constants $k_{off}$ of $1\times10^{-2}$ s$^{-1}$ or less, $1\times10^{-3}$ s$^{-1}$ or less, $1\times10^{-4}$ s$^{-1}$ or less, or $1\times10^{-5}$ s$^{-1}$ or less, in the order indicated.

Furthermore, antibodies of the invention may be chosen so as to inhibit the activity, in particular the neurotoxic activity, of oligomers of the invention or derivatives thereof with an $IC_{50}$ of $1\times10^{-8}$ M or less. Increasing preference is given to inhibition constants $IC_{50}$ of $1\times10^{-7}$ M or less, $1\times10^{-8}$ M or less, $1\times10^{9}$ M or less, $1\times10^{-10}$ M or less, or $1\times10^{-11}$ M or less, in the order indicated.

The antibodies are preferably isolated antibodies. According to another aspect, the antibodies are neutralizing antibodies. The antibodies of the invention include monoclonal and recombinant antibodies. According to a multiplicity of embodiments, the antibody may comprise an amino acid sequence derived entirely from a single species, such as a human antibody or a mouse antibody. According to other embodiments, the antibody may be a chimeric antibody or a CDR graft antibody or another form of a humanized antibody.

The term "antibody" is intended to refer to immunoglobulin molecules consisting of 4 polypeptide chains, two heavy (H) chains and two light (L) chains. The chains are usually linked to one another via disulfide bonds. Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region consists of three CDRs and four FRs which are arranged from the N terminus to the C terminus in the following order: FR1, CDR1, FR2, CDR2, FR3, CDR3, FR4.

The term "antigen-binding moiety" of an antibody (or simply "antibody moiety") refers to one or more fragments of an antibody having specificity for an oligomer of the invention or derivative thereof, said fragment(s) still being capable of specifically binding said oligomer or derivative thereof. Fragments of a complete antibody have been shown to be able to carry out the antigen-binding function of an antibody. In accordance with the term "antigen-binding moiety" of an antibody examples of binding fragments include (i) an Fab fragment, i.e. a monovalent fragment composed of the VL, VH, CL and CH1 domains; (ii) an F(ab')$_2$ fragment, i.e. a bivalent fragment comprising two Fab fragments linked to one another in the hinge region via a disulfide bridge; (iii) an Fd fragment composed of the VH and CH1 domains; (iv) an Fv fragment composed of the FL and VH domains of a single arm of an antibody; (v) a dAb fragment (Ward et al., (1989) Nature 341:544-546) consisting of a VH domain or of VH, CH1, CH2, DH3, or VH, CH2, CH3; and (vi) an isolated complementarity-determining region (CDR). Although the two domains of the Fv fragment, namely VL and VH, are encoded by separate genes, they may further be linked to one another using a synthetic linker and recombinant methods, making it possible to prepare them as a single protein chain in which the VL and VH regions combine in order to form monovalent molecules (known as single chain Fv (ScFv); see, for example, Bird et al. (1988) Science 242:423-426; and Huston et al. (1988) Proc. Natl. Acad. Sci. USA 85:5879-5883). The term "antigen-binding moiety" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, P., et al. (1993) Proc. Natl. Acad. Sci. USA 90:6444-6448; Poljak, R. J., et al. (1994) Structure 2:1121-1123).

Furthermore, an antibody or antigen-binding moiety thereof may be part of a larger immunoadhesion molecule formed by covalent or noncovalent association of said antibody or antibody moiety with one or more further proteins or peptides. Relevant to such immunoadhesion molecules are the use of the streptavidin core region in order to prepare a tetrameric scFv molecule (Kipriyanov; S. M., et al. (1995) Human Antibodies and Hybridomas 6:93-101) and the use of a cystein residue, a marker peptide and a C-terminal polyhistidine tag in order to produce bivalent and biotinylated scFv molecules (Kipriyanov, S. M., et al. (1994) Mol. Immunol. 31:1047-1058). Antibody moieties such as Fab and F(ab')$_2$ fragments may be produced from whole antibodies by using conventional techniques such as digestion with papain or pepsin. In addition, antibodies, antibody moieties and immunoadhesion molecules may be obtained by using standardized recombinant DNA techniques. An "isolated antibody having specificity for an oligomer of the invention or derivative thereof" means an antibody having specificity for an oligomer of the invention or derivative thereof, which is essentially free of other antibodies having different antigen specificities, i.e. in particular an antibody which is free of antibodies specifically binding to other forms of the Aβ(1-42) protein, as described above.

The term "neutralizing antibody" means an antibody whose binding to a particular antigen results in the inhibition of the biological activity of said antigen. Said inhibition of the biological activity of the antigen may be assessed by measuring one or more indicators for said biological activity of the antigen, using a suitable in-vitro or in-vivo assay.

The term "monoclonal antibody" means an antibody derived from a hybridoma (e.g. an antibody secreted by a hybridoma prepared by means of hybridoma technology such as the standardized hybridoma methods according to Kohler and Milstein). An antibody which is derived from a hybridoma and which has specificity for an oligomer of the invention or derivative thereof is therefore referred to as monoclonal antibody.

The term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes (see, for example, Taylor, L. D., et al. (1992) Nucl. Acids Res. 20:6287-6295); or antibodies which are produced, expressed, generated or isolated in any other way in which particular immunoglobulin gene sequences (such as human immunoglobulin gene sequences) are assembled with other DNA sequences. Recombinant antibodies include, for example, chimeric, CDR graft and humanized antibodies.

The term "human antibody" refers to antibodies whose variable and constant regions correspond to or derive from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies of the invention may contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies of the invention have variable regions and may also contain constant regions derived from immunoglobulin sequences of the human germ line (see Kabat, E. A., et al. (1991) *Sequences of Proteins of Immunological Interest, Fifth Edition*, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both.

The term "back mutation" refers to a method which comprises replacing some of or all of the somatically mutated amino acids of a human antibody with the corresponding germ line residues of a homologous germ line antibody sequence. The sequences for the heavy and light chains of a human antibody of the invention are compared separately with the germ line sequences in the VBASE database to identify the sequences having the highest homology. Imprints on the human antibodies of the invention are reverted to the germ line sequence by mutating defined nucleotide positions encoding such deviating amino acids. The direct or indirect importance of each amino acid identified in this way as a candidate for a back mutation for antigen binding should be investigated, and an amino acid impairing a desired property of said human antibody after mutation should not be incorporated in the final human antibody. In order to keep the number of amino acids for back mutation as low as possible, those amino acid positions which, although deviating from the closest germ line sequence, are identical to the corresponding amino acid sequence of a second germ line sequence may remain unchanged, provided that said second germ line sequence is identical and colinear with the sequence of the human antibody of the invention in at least 10 and preferably in 12 amino acids on both sides of the amino acid in question. Back mutations may be carried out at any stage of antibody optimization.

The term "chimeric antibody" refers to antibodies which contain sequences for the variable region of the heavy and light chains from one species but in which the sequences of one or more of the CDR regions of VH and/or VL have been replaced with CDR sequences of another species, such as antibodies having variable regions of the heavy and light chains from mouse, in which one or more of the mouse CDRs (e.g. CDR3) have been replaced with human CDR sequences.

The term "humanized antibody" refers to antibodies which contain sequences of the variable region of heavy and light chains from a nonhuman species (e.g. mouse, rat, rabbit, chicken, camelid, goat) but in which at least one part of the VH and/or VL sequence has been altered in order to be more "human-like", i.e. to be more similar to variable sequences of the human germ line. One type of a humanized antibody is a CDR graft antibody in which human CDR sequences have been inserted into nonhuman VH and VL sequences to replace the corresponding nonhuman CDR sequences.

One way of measuring the binding kinetics of an antibody is by means of surface plasmon resonance. The term "surface plasmon resonance" refers to an optical phenomenon by which biospecific interactions can be analyzed by detecting changes in protein concentrations by means of a biosensor matrix, using, for example, the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{off}$" refers to the off rate constant for the dissociation of an antibody from the antibody/antigen complex.

The term "$K_d$" refers to the dissociation constant of a particular antibody-antigen interaction.

The binding affinity of the antibodies of the invention may be evaluated by using standardized in-vitro immunoassays such as ELISA or BIAcore analyses.

Apart from antibodies, the protein may be a T cell receptor-derived molecule or a T cell receptor-derived receptor domain or a fusion protein of said receptor domain with an Fc moiety of an immunoglobulin.

The present invention also relates to pharmaceutical agents (compositions) containing a protein of the invention and in particular an antibody of the invention and also, optionally, a pharmaceutically suitable carrier. Pharmaceutical compositions of the invention may furthermore contain at least one additional therapeutic agent, for example one or more additional therapeutic agents for the treatment of a disease for whose relief the antibodies of the invention are useful. If, for example, the antibody of the invention binds to an oligomer of the invention, the pharmaceutical composition may furthermore contain one or more additional therapeutic agents useful for the treatment of disorders in which the activity of said oligomer is important.

Pharmaceutically suitable carriers include any solvents, dispersing media, coatings, antibacterial and antifungal agents, isotonic and absorption-delaying agents, and the like, as long as they are physiologically compatible. Pharmaceutically acceptable carriers include, for example, water, saline, phosphate-buffered saline, dextrose, glycerol, ethanol and the like, and combinations thereof. In many cases, preference is given to using isotonic agents, for example sugars, polyalcohols such as mannitol or sorbitol, or sodium chloride in addition. Pharmaceutically suitable carriers may furthermore contain relatively small amounts of auxiliary substances such as wetting agents or emulsifiers, preservatives or buffers, which increase the half life or efficacy of the antibodies.

The pharmaceutical compositions may be suitable for parenteral administration, for example. Here, the antibodies are prepared preferably as injectable solutions with an antibody content of 0.1-250 mg/ml. The injectable solutions may be prepared in liquid or lyophilized form, the dosage form being a flint glass or vial, an ampoule or a filled syringe. The buffer may contain L-histidine (1-50 mM, preferably 5-10 mM) and have a pH of 5.0-7.0, preferably of 6.0. Further suitable buffers include, without being limited thereto, sodium succinate, sodium citrate, sodium phosphate or potassium phosphate buffers. Sodium chloride may be used in order to adjust the tonicity of the solution to a concentration of 0-300 mM (preferably 150 mM for a liquid dosage form). Cryoprotectants, for example sucrose (e.g. 0-10%, preferably 0.5-1.0%) may also be included for a lyophilized dosage form. Other suitable cryoprotectants are trehalose and lactose. Fillers, for example mannitol (e.g. 1-10%, preferably 2-4%) may also be included for a lyophilized dosage form.

Stabilizers, for example L-methionine (e.g. 51-50 mM, preferably 5-10 mM) may be used both in liquid and lyophilized dosage forms. Further suitable fillers are glycine and arginine. Surfactants, for example polysorbate 80 (e.g. 0-0.05%, preferably 0.005-0.01%), may also be used. Further surfactants are polysorbate 20 and BRIJ surfactants.

The compositions of the invention may have a multiplicity of forms. These include liquid, semisolid and solid dosage forms, such as liquid solutions (e.g. injectable and infusible solutions), dispersions or suspensions, tablets, pills, powders, liposomes and suppositories. The preferred form depends on the intended type of administration and on the therapeutic application. Typically, preference is given to compositions in the form of injectable or infusible solutions, for example compositions which are similar to other antibodies for passive immunization of humans. The preferred route of administration is parenteral (e.g. intravenous, subcutaneous, intraperitoneal, intramuscular). According to a preferred embodiment, the antibody is administered by intravenous infusion or injection. According to another preferred embodiment, the antibody is administered by intramuscular or subcutaneous injection.

Therapeutic compositions must typically be sterile and stable under the preparation and storage conditions. The compositions may be formulated as solution, micro-emulsion, dispersion, liposome or another ordered structure suitable for high active substance concentrations. Sterile injectable solutions may be prepared by introducing the active compound (i.e. the antibody) in the required amount into a suitable solvent, where appropriate with one or a combination of the abovementioned ingredients, as required, and then sterile-filtering said solution. Dispersions are usually prepared by introducing the active compound into a sterile vehicle containing a basic dispersion medium and, where appropriate, other required ingredients. In the case of a sterile lyophilized powder for preparing sterile injectable solutions, vacuum drying and spray drying are preferred methods of preparation, which produces a powder of the active ingredient and, where appropriate, of further desired ingredients from a previously sterile-filtered solution. The correct flowability of a solution may be maintained by using, for example, a coating such as lecithin, by maintaining, in the case of dispersions the required particle size or by using surfactants. A prolonged absorption of injectable compositions may be achieved by additionally introducing into the composition an agent which delays absorption, for example monostearate salts and gelatin.

The antibodies of the invention may be administered by a multiplicity of methods known to the skilled worker, although the preferred type of administration for many therapeutic applications is subcutaneous injection, intravenous injection or infusion. The skilled worker will appreciate that the route and/or type of administration depend on the result desired. According to particular embodiments, the active compound may be prepared with a carrier which protects the compound against rapid release, such as, for example, a formulation with controlled release, which includes implants, transdermal plasters and microencapsulated release systems. Biologically degradable biocompatible polymers such as ethylene vinyl acetate, polyanhydrides, polyglycol acid, collagen, polyorthoesters and polylactic acid may be used. The methods of preparing such formulations are well known to the skilled worker, see, for example, *Sustained and Controlled Release Drug Delivery Systems*, J. R. Robinson, ed., Marcel Dekker, Inc., New York, 1978.

According to particular embodiments, an antibody of the invention may be administered orally, for example in an inert diluent or an assimilable edible carrier. The antibody (and further ingredients, if desired) may also be enclosed in a hard or soft gelatin capsule, compressed to tablets or added directly to food. For oral therapeutic administration, the antibodies may be mixed with excipients and used in the form of swallowable tablets, buccal tablets, capsules, elixirs, suspensions, syrups and the like. If it is intended to administer an antibody of the invention via a route other than the parenteral one, it may be necessary to choose a coating from a material which prevents its inactivation.

The antibodies of the invention are preferably capable of neutralizing, both in vitro and in vivo, the activity of oligomers of the invention or derivatives thereof to which they bind. Said antibodies may therefore be used for inhibiting the activity of oligomers of the invention or derivatives thereof, for example in a cell culture containing said oligomers or derivatives thereof or in human individuals or other mammals in which said oligomers or derivatives thereof are present. According to one embodiment, the invention relates to a method of inhibiting the activity of oligomers of the invention or derivatives thereof, which method comprises allowing an antibody of the invention to act on an oligomer or derivative thereof so as to inhibit the activity of said oligomer or derivative thereof. Said activity may be inhibited in vitro, for example. For example, the antibody of the invention may be added to a cell culture which contains or is suspected to contain the oligomer of the invention or derivative thereof, in order to inhibit the activity of said oligomer or derivative thereof in said culture. Alternatively, the activity of the oligomer or derivative thereof may be inhibited in an individual in vivo.

Thus the present invention further relates to a method of inhibiting the activity of oligomers of the invention or derivatives thereof in an individual who suffers from a disorder in which the amyloid β protein is involved and in which in particular the activity of said oligomer of the invention or derivative thereof is important. Said method comprises the administration of at least one antibody of the invention to the individual with the aim of inhibiting the activity of the oligomer or derivative thereof to which the antibody binds. Said individual is preferably a human being. An antibody of the invention may be administered for therapeutic purposes to a human individual. In addition, an antibody of the invention may be administered to a nonhuman mammal for veterinary purposes or within the framework of an animal model for a particular disorder. Such animal models may be useful for evaluating the therapeutic efficacy of antibodies of the invention (for example for testing dosages and time courses of administration).

Disorders in which the oligomers of the invention or derivatives thereof play a part include in particular disorders in whose development and/or course an oligomer of the invention or derivative thereof is involved. These are in particular those disorders in which oligomers of the invention or derivatives thereof are evidently or presumably responsible for the pathophysiology of said disorder or are a factor which contributes to the development and/or course of said disorder. Accordingly, those disorders are included here in which inhibition of the activity of oligomers of the invention or derivatives thereof can relieve symptoms and/or progression of the disorder. Such disorders can be verified, for example, by an increased concentration of oligomers of the invention or derivatives thereof in a biological fluid of an individual suffering from a particular disorder (e.g. increased concentration in serum, plasma, CSF, urine, etc.). This may be detected, for example, by using an antibody of the invention. The oligomers of the invention and derivatives thereof play an important part in the pathology associated with a multiplicity of disorders in which neurodegenerative elements, cognitive deficits, neurotoxic elements and inflammatory elements are involved.

The antibodies of the invention may be administered together with one or more additional therapeutic agents which are useful in the treatment of the above-described disorders.

The pharmaceutical compositions of the present invention usually contain a therapeutically active amount or a prophylactically active amount of at least one antibody of the invention. Depending on the treatment desired, for example whether a therapeutic or prophylactic treatment is desired, dosage plans can be chosen and adapted. For example, a single dose, multiple separate doses distributed over time or an increasing or decreasing dosage may be administered, depending on the requirements of the therapeutic situation. It is particularly advantageous to formulate parenteral compositions in single dosage form in order to facilitate administration and to ensure uniformity of the dosage.

A therapeutically or prophylactically active amount of an antibody of the invention may be, for example, in the range of 0.1-20 mg/kg and preferably 1-10 mg/kg, without being limited thereto: These amounts may, of course, vary, depending on the type and severity of the condition to be relieved.

Within the framework of diagnostic usage of the antibodies, qualitative or quantitative specific oligomer determination serves in particular to diagnose disease-relevant amyloid β(1-42) forms. In this context, specificity means the possibility of being able to detect a particular oligomer or oligomer mixture with sufficient sensitivity. The antibodies of the invention advantageously have sensitivities of less than 10 ng/ml of sample, preferably of less than 1 ng/ml of sample and particularly preferably of less than 100 pg/ml of sample, meaning that at least the concentration of oligomer per ml of sample, indicated in each case, advantageously also lower concentrations, can be detected by the antibodies of the invention.

The determination is carried out immunologically. This may be carried out in principle by using any analytical or diagnostic assay method in which antibodies are used, including agglutination and precipitation techniques, immunoassays, immunohistochemical methods and immunoblot techniques, for example Western blotting or dot blot methods. In vivo methods, for example imaging methods, are also included here.

The use in immunoassays is advantageous. Suitable are both competitive immunoassays, i.e. antigen and labeled antigen (tracer) compete for antibody binding, and sandwich immunoassays, i.e. binding of specific antibodies to the antigen is detected by a second, usually labeled antibody. These assays may be either homogeneous, i.e. without separation into solid and liquid phases, or heterogeneous, i.e. bound labels are separated from unbound ones, for example via solid phase-bound antibodies. Depending on labeling and method of measurement, the various heterogeneous and homogeneous immunoassay formats can be classified into particular classes, for example RIAs (radioimmunoassays), ELISA (enzyme-linked immunosorbent assay), FIA (fluorescence immunoassay), LIA (luminescence immunoassay), TRFIA (time-resolved FIA), IMAC (immunoactivation), EMIT (enzyme-multiplied immune test), TIA (turbodimetric immunoassay), I-PCR (immuno-PCR).

For the oligomer determination of the invention, preference is given to competitive immunoassays in which labeled oligomer (tracer) competes with the oligomer to be quantified of the sample for binding to the antibody used. The amount of antigen, i.e. the amount of oligomer, in the sample can be determined from the amount of the displaced tracer with the aid of a standard curve.

Of the labels available for these purposes, enzymes have proved advantageous. Systems based on peroxidases, in particular horseradish peroxidase, alkaline phosphatase and β-D-galactosidase, may be used, for example. Specific substrates whose conversion can be monitored photometrically, for example, are available for these enzymes. Suitable substrate systems are based on p-nitrophenyl phosphate (p-NPP), 5-bromo-4-chloro-3-indolyl phosphate/nitroblue tetrazolium (BCIP/NPT), Fast-Red/naphthol-AS-TS phosphate for alkaline phosphatase; 2,2-azinobis(3-ethyl-benzothiazoline-6-sulfonic acid) (ABTS), o-phenylenediamine (OPT), 3,3',5,5'-tetramethylbenzidine (TMB), o-dianisidine, 5-aminosalicylic acid, 3-dimethylamino-benzoic acid (DMAB) and 3-methyl-2-benzothiazolinehydrazone (MBTH) for peroxidases; o-nitrophenyl-β-D-galactoside (o-NPG), p-nitrophenyl-β-D-galactoside and 4-methylumbelliphenyl-β-D-galactoside (MUG) for β-D-galactosidase. In many cases, these substrate systems are commercially available in a ready-to-use form, for example in the form of tablets which may also contain further reagents such as appropriate buffers and the like.

The tracers used are labeled oligomers. In this sense, a particular oligomer can be determined by labeling the oligomer to be determined and using it as tracer.

The coupling of labels to oligomers for preparing tracers may be carried out in a manner known per se. The comments above on derivatization of oligomers of the invention are referred to by analogy. In addition, a number of labels appropriately modified for conjugation to proteins are available, for example biotin-, avidin-, extravidin- or streptavidin-conjugated enzymes, maleimide-activated enzymes and the like. These labels may be reacted directly with the oligomer or, if required, with the appropriately derivatized oligomer to give the tracer. If, for example, a streptavidin-peroxidase conjugate is used, then this firstly requires biotinylation of the oligomer. This applies correspondingly to the reverse order. For this purpose too, suitable methods are known to the skilled worker.

If a heterogeneous immunoassay format is chosen, the antigen-antibody complex may be separated by binding it to the support, for example via an anti-idiotypical antibody coupled to said support, e.g. an antibody directed against rabbit IgG. Supports, in particular microtiter plates coated with appropriate antibodies are known and partly commercially available.

The present invention further relates to immunoassay sets having at least one above-described antibody and further components. Said sets are, usually in the form of a packaging unit, a combination of means for carrying out an oligomer determination of the invention. For the purpose of handling which is as easy as possible, said means are preferably provided in an essentially ready-to-use form. An advantageous arrangement offers the immunoassay in the form of a kit. A kit usually comprises multiple containers for separate arrangement of components. All components may be provided in a ready-to-use dilution, as a concentrate for diluting or as a dry substance or lyophilisate for dissolving or suspending; individual or all components may be frozen or stored at room temperature until use. Sera are preferably shock-frozen, for example at −20° C. so that in these cases an immunoassay has to be kept preferably at temperatures below freezing prior to use.

Further components supplied with the immunoassay depend on the type of said immunoassay. Usually, standard protein, tracer which mayor may not be required and control serum are supplied together with the antiserum. Furthermore, microtiter plates, preferably antibody-coated, buffers, for example for testing, for washing or for conversion of the substrate, and the enzyme substrate itself may also be included.

General principles of immunoassays and generation and use of antibodies as auxiliaries in laboratory and hospital can be found, for example, in Antibodies, A Laboratory Manual (Harlow, E., and Lane, D., Ed., Cold Spring Harbor Laboratory, Cold Spring Harbor, N.Y., 1988).

Furthermore of interest are also substances which inhibit aggregation of the oligomers of the invention or accelerate disaggregation thereof. Such substances particularly represent possible therapeutic agents for the treatment of the above amyloid β-associated disorders such as, for example, Alzheimer's disease.

The present invention therefore also relates to a method of characterizing a substance or a substance mixture, which method comprises
i) providing said substance or said substance mixture in a suitable manner;
ii) allowing said substance or said substance mixture to act on at least one oligomer of the invention, derivative thereof or a composition; and
iii) determining whether said substance or particular parts of said substance mixture bind to said oligomer, derivative thereof or to at least one oligomer or derivative thereof present in said composition.

Said method may also be carried out on mixtures of biological origin, for example a cell preparation and cell extracts, in order to identify natural binding partners with affinity for the oligomers of the invention, for example cell surface antigens, in particular receptors, and soluble ligands, for example particular proteins and mediators.

In addition to mere binding of the substances, further interactions with and influences on the oligomers of the invention may also be a subject of said method. Thus it is possible to determine, in particular, whether
the substance is capable of modulating, in particular inhibiting, the aggregation of amyloid β protein to the oligomers of the invention;
the substance is capable of modulating, in particular promoting, disaggregation of the oligomers of the invention;
the oligomers of the invention cause functional changes in a binding partner, for example have an agonistic, partially agonistic, antagonistic or inverse agonistic effect on a receptor.

Said methods are usually in vitro-screening methods which can be used to select from a multiplicity of different substances those which appear to be most promising with respect to a future application. It is possible, for example, to establish by means of combinatorial chemistry extensive substance libraries comprising myriads of potential active substances. The screening of combinatorial substance libraries for substances having the desired activity can be automated. Screening robots serve to efficiently analyze the individual assays which are preferably arranged on microtiter plates. Thus the present invention also relates to screening methods, i.e. both primary and secondary screening methods, in which preferably at least one of the methods described below is applied. If several methods are applied, they may be applied to one and the same sample with a time shift or simultaneously or to different samples of a substance to be tested.

A particularly effective technique for carrying out such methods is the scintillation proximity assay, SPA for short, which is known in the field of drug screening. Kits and components for carrying out this assay may be obtained commercially, for example from Amersham Pharmacia Biotech. In principle, solubilized or membrane-bound receptors are immobilized on small fluoromicrospheres containing a scintillating substance. When, for example, a radioligand binds to the immobilized receptors, said scintillating substance is stimulated and emits light, due to the spatial proximity of scintillating substance and radioligand.

Another particularly effective technique for carrying out methods of this kind is the FlashPlateR technique known in the field of drug screening. Kits and components for carrying out this assay may be commercially obtained, for example from NENR Life Science Products. This principle is likewise based on microtiter plates (96- or 384-well) coated with scintillating substance.

The present invention relates to substances or parts of substance mixtures, which are identifiable according to this method as a ligand binding to the oligomer, derivative thereof or to at least one oligomer or derivative thereof present in a corresponding composition, as well as to the use thereof for preparing a medicament for the treatment of amyloid β-associated, in particular dementing, disorders or for preparing a composition for diagnosing amyloid β-associated, in particular dementing, disorders.

The following examples are intended to illustrate the invention, without limiting its scope.

Figure 9:
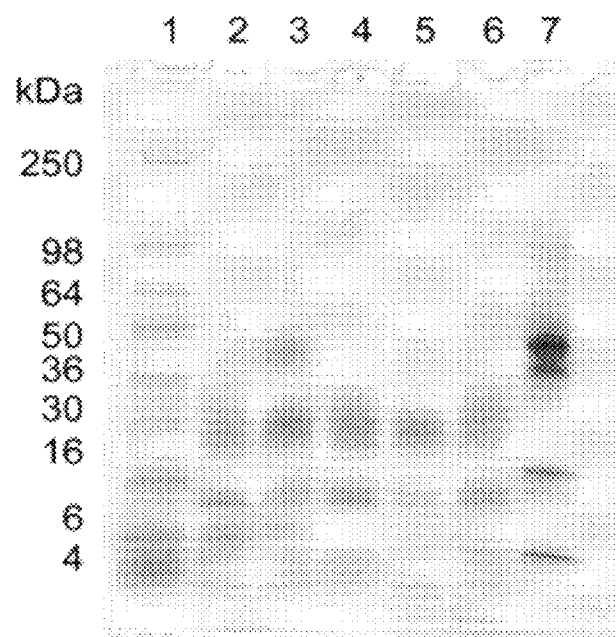
Figure 11A:
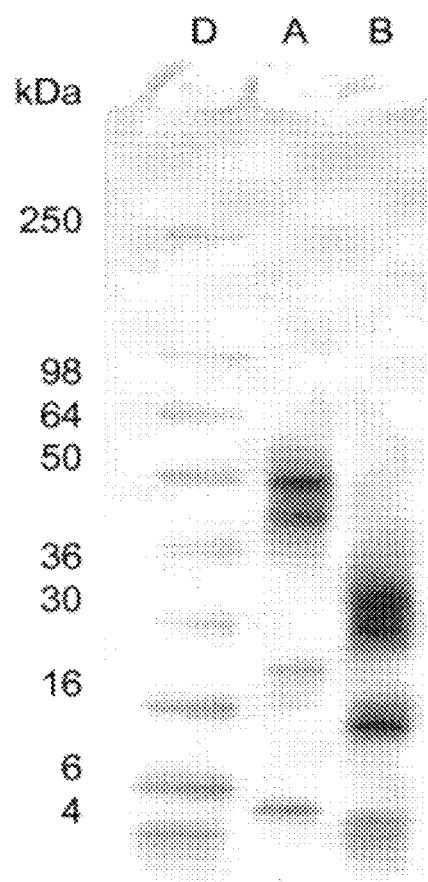
Figure 11B:
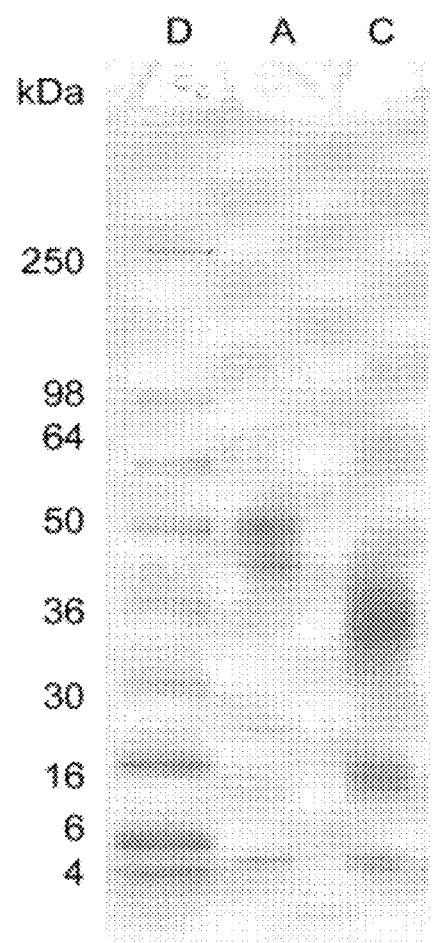
Figure 12:
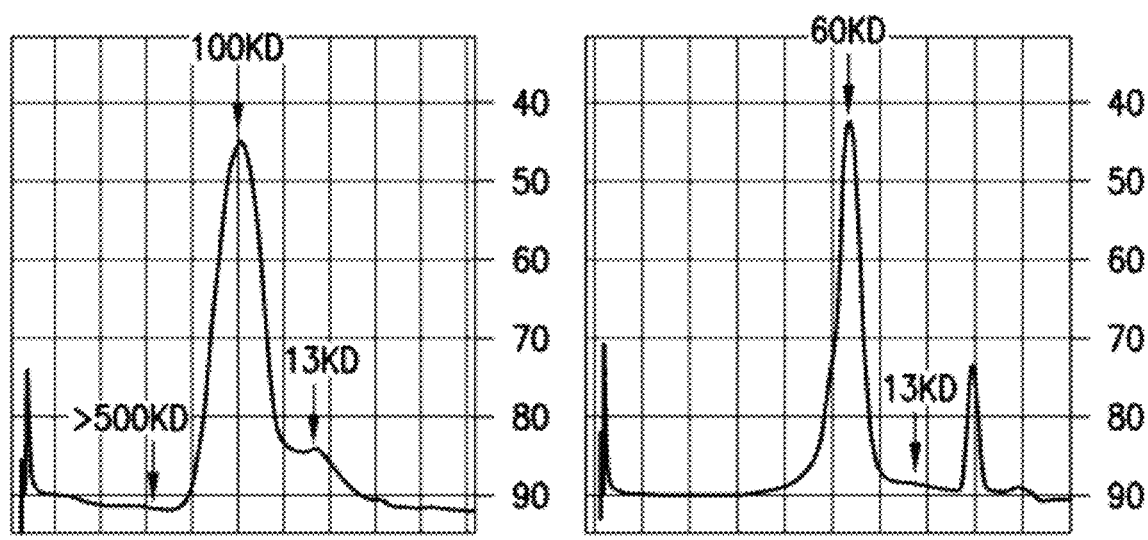
Figure 13:
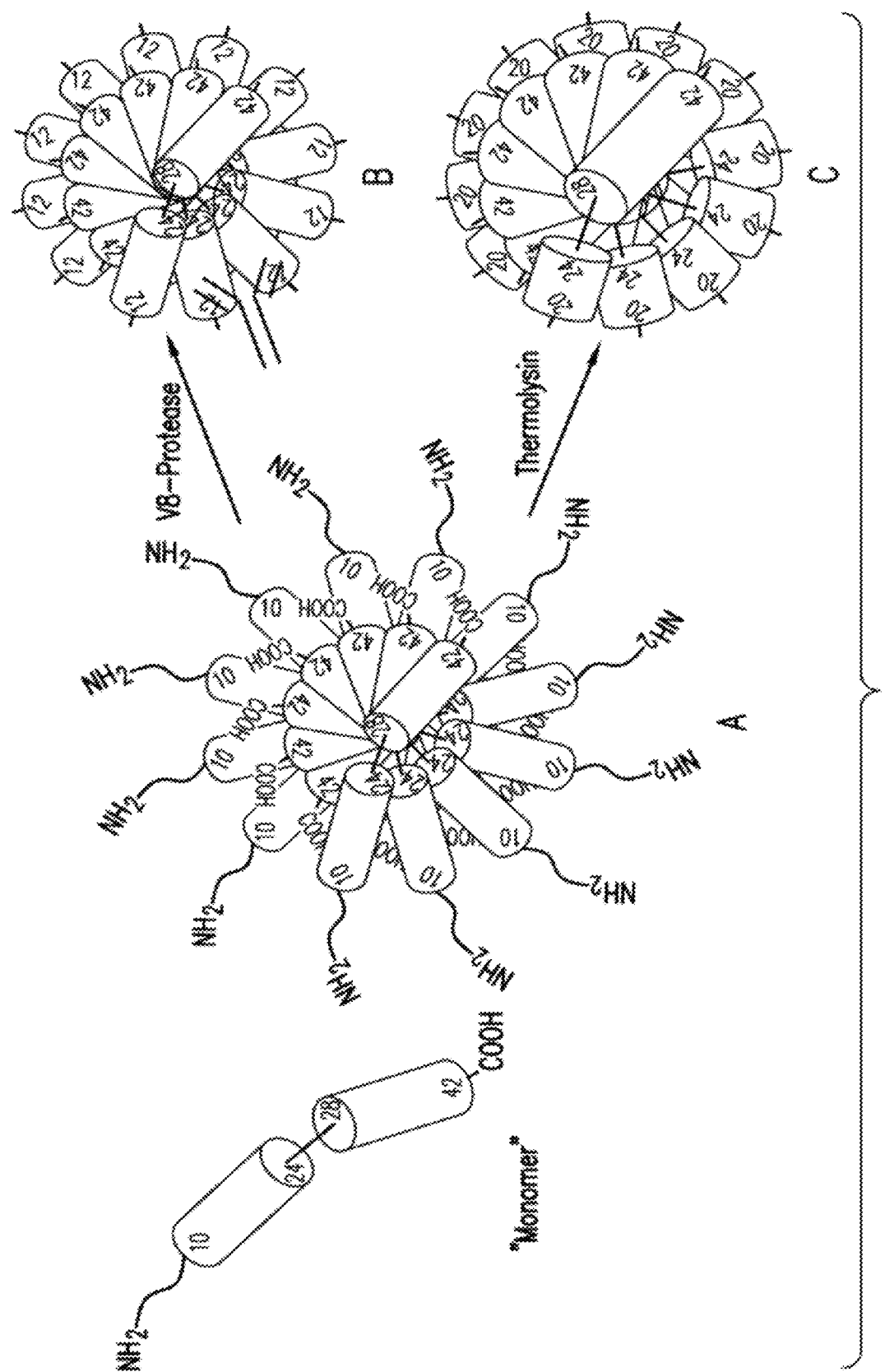
Figure 14:
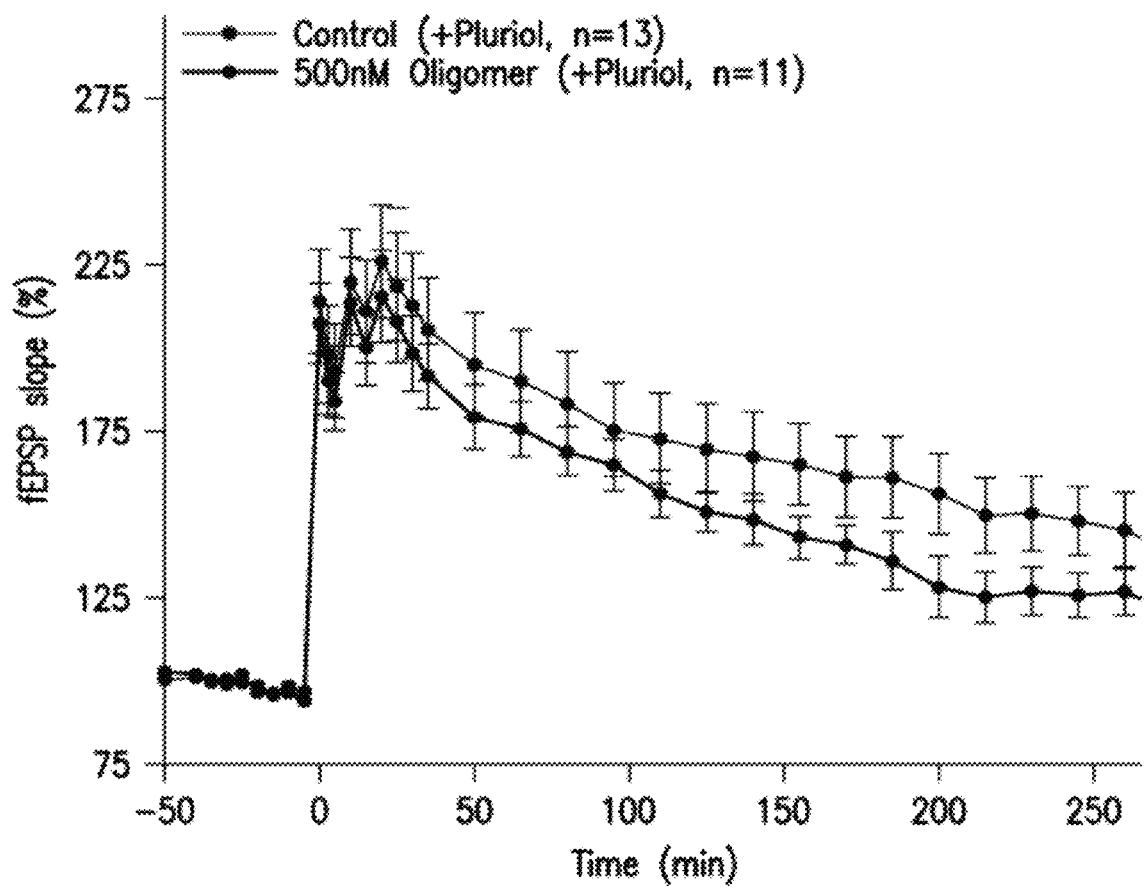

FIG. 9 shows an SDS PAGE of an Aβ(1-42) preparation treated with trypsin (lane 2), chymotrypsin (lane 3), thermolysin (lane 4), elastase (lane 5), papain (lane 6) or untreated (lane 7); and of standard proteins (molecular marker proteins, lane 1);

FIG. 10 shows dot blots of the reactivity of 100 pmol (row A); 10 pmol (row B); 1 pmol (row C); 0.1 pmol (row D) and 0.01 pmol (row E); of Aβ(1-42) oligomer B preparation of example 6b (column 1); of HFIP-treated Aβ(1-42) monomer of example 1a (column 2); of thermolysin-cleaved Aβ(1-42) oligomer B preparation of example 15a (column 3); of glutaraldehyde-crosslinked Aβ(1-42) oligomer B preparation of example 14a (column 4); of ADDL prepared according to M. P. Lambert et al., J. Neurochem. 79, 595-605 (2001) at 4° C. or room temperature or 37° C. (columns 5, 6 and 7, respectively); of Aβ(1-42) dissolved in 0.1% NH$_4$OH (column 8); of an Aβ(1-42) fibril preparation of example 27 (column 9); and of PBS-diluted APP from Sigma (column 10) with a) the monoclonal antibody 6E10; b) the polyclonal antiserum (d1) of example 25d; c) the polyclonal antiserum (c1) of example 25c; d) the polyclonal antiserum (a1) of example 25a; and e) the polyclonal antiserum (a2) of example 25a;

FIG. 11 shows an SDS PAGE of an Aβ(20-42) oligomer B preparation of example 15a (lane B); of an Aβ(12-42) oligomer B preparation of example 15b (lane C); of an Aβ(1-42) oligomer B preparation of example 6b (lane A); and of standard proteins (molecular marker proteins, lane D);

FIG. 12 shows a gel permeation chromatography of the Aβ(1-42) oligomer B preparation of example 6b in comparison with the Aβ(1-42) oligomer B-CL preparation of example 14a;

FIG. 13 shows a diagrammatic representation of the monomeric Aβ(1-42) protein (left); of the Aβ(1-42) oligomer (12-mer, A); and of the Aβ(12-42) oligomer (12-mer, C) and Aβ(20-42) oligomer (12-mer, B) both of which are obtainable by proteolytic cleavage;

FIG. 14 shows the excitatory postsynaptic potential (fEPSP) as a function of the time of action of Aβ(1-42) oligomers B on hippocampal sections;

FIG. 15 shows an immunofluorescence image depicting the binding of Aβ(1-42) oligomers B to hippocampal rat neurons (a) in comparison with unspecifically bound fluorescence (b).

Unless stated otherwise, concentrations of oligomers of the invention are expressed in moles of monomeric Aβ(1-42) polypeptide. The term 13 amyloid(1-42) protein corresponds to the term amyloid β(1-42) protein. Unless stated otherwise, the proteins (polypeptides) used are of human origin.

EXAMPLE 1 a) Preparation of a Stock Suspension of Human Aβ(1-42)

2 mg of human β-amyloid(1-42) protein (short name: Aβ(1-42); peptide-synthetic material, lyophilisate, from Bachem, Germany) are dissolved in 800 μl of 1,1,1,3,3,3-hexafluoro-2-propanol and incubated in an Eppendorf vessel at 37° C. for 30 min. This is followed by evaporation to dryness in a vacuum concentrator (Speed Vac). The residue is taken up with 88 μl of DMSO, resulting in a 5 mM Aβ(1-42) stock suspension which can be stored at −20° C.

b) Preparation of a Stock Suspension or Rat Aβ(1-42)

2 mg of rat β-amyloid(1-42) protein (short name: rat Aβ(1-42); peptide-synthetic material, lyophilisate, from Bachem, Germany) by dissolving 800 μl of 1,1,1,3,3,3-hexafluoro-2-propanol and incubated in an Eppendorf vessel at 37° C. for 30 min. This is followed by evaporation to dryness in a vacuum concentrator (Speed Vac). The residue is taken up with 88 μl of DMSO, resulting in a 5 mM rat Aβ(1-42) stock suspension which can be stored at −20° C.

EXAMPLE 2 a) Preparation of Aβ(1-42) Oligomers Having Molecular Weights of 15 KDa and 20 kDa [Aβ(1-42) Oligomers A]; Use of SDS 690 μl of PBS buffer (20 mM sodium phosphate, 140 mM NaCl, pH 7.4) are added to 60 μl of the stock solution of example 1a and the mixture is adjusted to SDS content of 0.2% with 75 μl of 2% strength sodium dodecyl sulfate (SDS) solution. This is followed by 5 hours of incubation at 37° C. and centrifugation for 10 min at 10 000 g. This Aβ(1-42) oligomer A preparation (approx. 400 μM Aβ(1-42)) can be stored at −20° C.

b) Preparation of rat Aβ(1-42) Oligomers Having Molecular Weights of 15 KDa and 20 kDa [Rat Aβ(1-42) Oligomers A]; Use of SDS 690 μl of PBS buffer (20 mM sodium phosphate, 140 mM NaCl, pH 7.4) are added to 60 μl of the stock solution of example 1b and the mixture is adjusted to SDS content of 0.2% with 75 μl of 2% strength sodium dodecyl sulfate (SDS) solution. This is followed by 5 hours of incubation at 37° C. and centrifugation for 10 min at 10 000 g. This rat Aβ(1-42) oligomer A preparation (approx. 400 μM rat Aβ(1-42)) can be stored at −20° C.

c) Preparation of Aβ(1-42) Oligomers Having Molecular Weights of 15 KDa and 20 kDa [Aβ(1-42) Oligomers A]; Use of Lauric Acid 6900 of PBS buffer (20 mM sodium phosphate, 140 mM NaCl, pH 7.4) are added to 60 μl of the stock solution of example 1a and the mixture is adjusted to lauric acid content of 0.5% with 75 μl of 5% strength lauric acid solution. This is followed by 5 hours of incubation at 37° C. and centrifugation for 10 min at 10 000 g. This Aβ(1-42) oligomer A preparation (approx. 400 μM Aβ(1-42)) can be stored at −20° C.

d) Preparation of Aβ(1-42) Oligomers Having Molecular Weights of 15 KDa and 20 kDa [Aβ(1-42) Oligomers A]; Use of Oleic Acid 690 μl of PBS buffer (20 mM sodium phosphate, 140 mM NaCl, pH 7.4) are added to 60 μl of the stock solution of example 1a and the mixture is adjusted to oleic acid content of 0.5% with 75 μl of 5% strength oleic acid solution. This is followed by 5 hours of incubation at 37° C. and centrifugation for 10 min at 10 000 g. This Aβ(1-42) oligomer A preparation (approx. 400 μM Aβ(1-42)) can be stored at −20° C.

e) Preparation of Aβ(1-42) Oligomers Having Molecular Weights of 15 KDa and 20 kDa [Aβ(1-42) Oligomers A]; Use of Lauroylsarcosine 690 μl of PBS buffer (20 mM sodium phosphate, 140 mM NaCl, pH 7.4) are added to 60 μl of the stock solution of example 1a and the mixture is adjusted to lauroylsarcosine content of 0.5% with 75 μl of 5% strength lauroylsarcosine solution. This is followed by 5 hours of incubation at 37° C. and centrifugation for 10 min at 10000 g. This Aβ(1-42) oligomer A preparation (approx. 400 μM Aβ(1-42)) can be stored at −20° C.

EXAMPLE 3 a) Alternative Method of Preparing Aβ(1-42) Oligomers Having Molecular Weights of 15 kDa and 20 kDa [Aβ(1-42) Oligomers A]

1 mg of human β-amyloid(1-42) protein (short name: Aβ(1-42); peptide-synthetic material, lyophilisate, from Bachem, Germany) is taken up in 220 μl of 10 mM aqueous HCl solution and incubated at room temperature for 10 min.

Insoluble components are removed by centrifugation at 10 000 g for 5 min. The supernatant (1 mM Aβ(1-42)) contains the Aβ(1-42) protein and is processed further as follows:

9 μl of PBS buffer and 1 μl of 2% strength SDS solution are added to 1 μl of the supernatant and the mixture is incubated at 37° C. for 16 h. The hAβ(1-42) oligomer A preparation (100 μM) can be stored at −20° C.

b) Alternative Method of Preparing Rat Aβ(1-42) Oligomers Having Molecular Weights of 15 KDa and 20 KDa [Rat Aβ(1-42) Oligomers A]

1 mg of rat β-amyloid(1-42) protein (short name: rat Aβ(1-42); peptide-synthetic material, lyophilisate, from Bachem, Germany) is taken up in 220 μl of 10 mM aqueous HCl solution and incubated at room temperature for 10 min. Insoluble components are removed by centrifugation at 10 000 g for 5 min. The supernatant (1 mM rat Aβ(1-42)) contains the rat amyloid-β(1-42) protein and is processed further as follows:

9 μl of PBS buffer and 1 μl of 2% strength SDS solution are added to 1 μl of the supernatant and the mixture is incubated at 37° C. for 16 h. The rat Aβ(1-42) oligomer A preparation (100 μM) can be stored at −20° C.

EXAMPLE 4 a) Alternative Method of Preparing Aβ(1-42) Oligomers Having Molecular Weights of 15 kDa and 20 kDa [Aβ(1-42) Oligomers A]

1 mg of human β-amyloid(1-42) protein (short name: Aβ(1-42); peptide-synthetic material, lyophilisate, from Bachem, Germany) is dissolved in 44 μl of 1% SDS/H$_2$O (5 mM Aβ(1-42)). 5 μl of the solution are admixed with 40 μl PBS and 5 μl of 2% SDS and incubated at 37° C. for 16 h. Insoluble components are removed by centrifugation at 10 000 g for 5 min. The thus obtained Aβ(1-42) oligomer A preparation (500 μM Aβ(1-42)) can be stored at −20° C.

b) Alternative Method of Preparing Rat Aβ(1-42) Oligomers Having Molecular Weights of 15 KDa and 20 KDa [Rat Aβ(1-42) Oligomers A]

1 mg of rat β-amyloid(1-42) protein (short name: rat Aβ(1-42); peptide-synthetic material, lyophilisate, from Bachem, Germany) is dissolved in 44 μl of 1% SDS/H$_2$O (5 mM rat Aβ(1-42)). 5 μl of the solution are admixed with 40 μl PBS and 5 μl of 2% SDS and incubated at 37° C. for 16 h. Insoluble components are removed by centrifugation at 10 000 g for 5 min. The thus obtained rat Aβ(1-42) oligomer A preparation (500 μM rat Aβ(1-42)) can be stored at −20° C.

EXAMPLE 5 a) Preparation of Aβ(1-42) Oligomers Having Molecular Weights of 38 KDa and 48 kDa [Aβ(1-42) Oligomers B]

An Aβ(1-42) oligomer A solution obtained according to example 2a is diluted with 2.475 ml of water (0.05% SDS content, 0.1 mM Aβ(1-42)) and incubated at 37° C. for 20 hours. Aliquots of this Aβ(1-42) oligomer B preparation can be frozen at −80° C. and stored for further studies.

b) Preparation of Rat Aβ(1-42) Oligomers Having Molecular Weights of 38 KDa and 48 kDa [rat Aβ(1-42) Oligomers B]

A rat Aβ(1-42) oligomer A solution obtained according to example 2a is diluted with 2.475 ml of water (0.05% SDS content, 0.1 mM rat Aβ(1-42)) and incubated at 37° C. for 20 hours. Aliquots of this rat Aβ(1-42) oligomer B preparation can be frozen at −80° C. and stored for further studies.

c) Alternative Preparation of Aβ(1-42) Oligomers Having Molecular Weights of 38 kDa and 48 kDa [Aβ(1-42) Oligomers B]

An Aβ(1-42) oligomer A solution obtained according to example 2c is diluted with 2.475 ml of water (0.125% lauric acid content, 0.1 mM Aβ(1-42)) and incubated at 37° C. for 20 hours. Aliquots of this Aβ(1-42) oligomer B preparation can be frozen at −80° C. and stored for further studies.

d) Alternative Preparation of Aβ(1-42) Oligomers Having Molecular Weights of 38 kDa and 48 kDa [Aβ(1-42) Oligomers B]

An Aβ(1-42) oligomer A solution obtained according to example 2d is diluted with 2.475 ml of water (0.125% oleic acid content, 0.1 mM Aβ(1-42)) and incubated at 37° C. for 20 hours. Aliquots of this Aβ(1-42) oligomer B preparation can be frozen at −80° C. and stored for further studies.

e) Alternative Preparation of Aβ(1-42) Oligomers B Having Molecular Weights of 38 kDa and 48 kDa [Aβ(1-42) Oligomers B]

An Aβ(1-42) oligomer A solution obtained according to example 2e is diluted with 2.475 ml of water (0.125% laurylsarcosine content, 0.1 mM Aβ(1-42)) and incubated at 37° C. for 20 hours. Aliquots of this Aβ(1-42) oligomer B preparation can be frozen at −80° C. and stored for further studies.

f) Preparation of SDS-Free Aβ(1-42) Oligomers B Having Molecular Weights of 38 kDa and 48 kDa [Aβ(1-42) Oligomers B]

10 μl of an Aβ(1-42) oligomer B preparation prepared according to example 6b are admixed with 250 μl of an acetic acid/methanol/water mixture in a 4%/33%/63% ratio and incubated at 0° C. on ice for 30 min. After centrifugation (10,000 g for 10 min), the supernatant is removed and the precipitated protein residue taken up to 200 μl of buffer (20 mM sodium phosphate, 140 mM NaCl, pH 7.4). The preparation obtained in this way contains the dissolved Aβ(1-42) oligomers B in SDS-free from and can be stored at −20° C.

EXAMPLE 6 a) Dialysis and Concentration of Aβ(1-42) Oligomers Having Molecular Weights of 38 kDa and 48 kDa [Aβ(1-42) Oligomers B]

An Aβ(1-42) oligomer B preparation prepared according to example 5a is admixed with 30 ml of PBS buffer containing 0.1% Pluronic® F68 (BASF) and concentrated to 3 ml in an Amicon Centriprep YM, 30 kD. Residues which may be present are removed by centrifugation (10,000 g for 5 min). The supernatant is removed. Aliquots of this Aβ(1-42) oligomer B preparation can be frozen at −80° C. and stored for further studies.

b) Preparation of a Concentrate of Aβ(1-42) Oligomers B Having Molecular Weights of 38 KDa and 48 KDa [Aβ(1-42) Oligomers B]

72.6 ml of an Aβ(1-42) oligomer B preparation obtained according to example 5a are concentrated to 2 ml via a 30 kD Centriprep YM Tube (Amicon). The concentrate is removed by centrifugation at 10 000 g for 10 min. The supernatant is removed and dialyzed at 6° C. in a dialysis tube against 1 l of buffer (5 mM sodium phosphate, 35 mM sodium chloride, pH 7.4) for 16 h. The dialysate is removed by centrifugation at 10 000 g for 10 min. The supernatant is removed and can be stored at −80° C. for further studies.

EXAMPLE 7

Preparation of biotin-Aβ(1-42) Stock Suspension 0.5 mg of biotin-β-amyloid(1-42) protein (short name: biotin-Aβ(1-42); peptide-synthetic material, lyophilisate, AnaSpec) are dissolved in 200 µl of 1,1,1,3,3,3-hexafluoro-2-propanol and incubated in an Eppendorf vessel at 37° C. for 30 min. This is followed by evaporation to dryness in a vacuum concentrator (Speed Vac). The residue is taken up with 20.5 µl of DMSO, producing a 5 mM biotin-Aβ(1-42) stock suspension which can be stored at −20° C.

EXAMPLE 8

Preparation of Biotin-Aβ(1-42) Oligomers Having Molecular Weights of 17 KDa and 22 kDa [Biotin-Aβ(1-42) Oligomers A]

2 µl of the stock suspension of example 7 are admixed with 23 µl of PBS buffer (20 mM sodium phosphate, 140 mM NaCl, pH 7.4) and adjusted to an SDS content of 0.2% with 2.4 µl of 2% strength. SDS solution. This is followed by 6 hours of incubation at 37° C. Insoluble components are removed by centrifugation at 10 000 g for 5 min. The biotin-Aβ(1-42) oligomer A preparation obtained in this way can be stored at −20° C.

EXAMPLE 9

Preparation of Biotin-Aβ(1-42) Oligomers Having Molecular Weights of 42 KDa and 52 kDa [Biotin-Aβ(1-42) Oligomers B]

Figure 3:
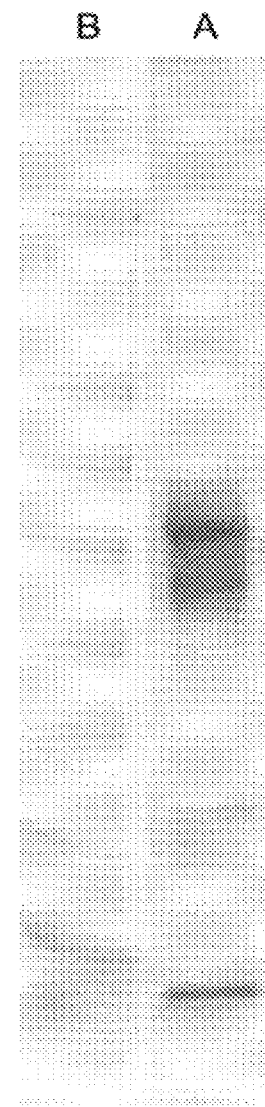
FIG. 3 shows an SDS PAGE of a biotin Aβ(1-42) oligomer B preparation (lane A); of standard proteins (molecular marker proteins, lane B)

A biotin-Aβ(1-42) oligomer A solution obtained according to example 8 is diluted with 82 µl of water (0.05% SDS content, 0.1 mM Aβ) and incubated at 37° C. for 16 hours. Insoluble components are removed by centrifugation at 10 000 g for 5 min. The biotin Aβ(1-42) oligomer B preparation can be frozen at −20° C. and stored for further studies. (FIG. 3).

EXAMPLE 10

Preparation of Fluorescein-Aβ(1-42) Stock Suspension 0.5 mg of fluorescein-β-amyloid(1-42) protein (short name: fluorescein-Aβ(1-42); peptide-synthetic material, lyophilisate, AnaSpec) are dissolved in 200 µl of 1,1,1,3,3,3-hexafluoro-2-propanol and incubated in an Eppendorf vessel at 37° C. for 30 min. This is followed by evaporation to dryness in a vacuum concentrator (Speed Vac). The residue is taken up with 20.5 µl of DMSO, producing a 5 mM fluorescein-Aβ(1-42) stock suspension which can be stored at −20° C.

EXAMPLE 11

Preparation of Fluorescein-Aβ(1-42) Oligomers Having Molecular Weights of 17 KDa and 22 kDa [Fluorescein-Aβ(1-42) Oligomer A]

2 µl of the stock suspension of example 10 are admixed with 23 µl of PBS buffer (20 mM sodium phosphate, 140 mM NaCl, pH 7.4) and adjusted to an SDS content of 0.2% with 2.4 µl of 2% strength SDS solution. This is followed by 6 hours of incubation at 37° C. Insoluble components are removed by centrifugation at 10 000 g for 5 min. The fluorescein-Aβ(1-42) oligomer A preparation obtained in this way can be stored at −20° C.

EXAMPLE 12

Preparation of Fluorescein-Aβ(1-42) Oligomers Having Molecular Weights of 42 KDa and 52 kDa [Fluorescein-Aβ(1-42) Oligomers B]

Figure 4:
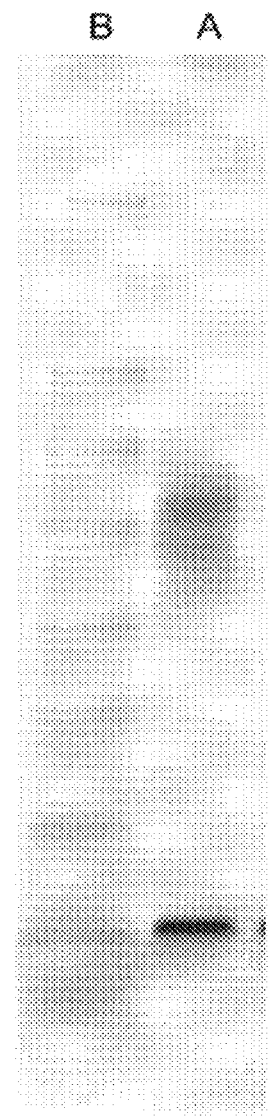
FIG. 4 shows an SDS PAGE of a fluorescein Aβ(1-42) oligomer B preparation (lane A); of standard proteins (molecular marker proteins, lane B)

A fluorescein-Aβ(1-42) oligomer A solution obtained according to example 11 is diluted with 82 µl of water (0.05% SDS content, 0.1 mM A6) and incubated at 37° C. for 16 hours. The fluorescein Aβ(1-42) oligomer B preparation can be frozen at −80° C. and stored for further studies. (FIG. 4).

EXAMPLE 13

Crosslinking of Aβ(1-42) Oligomers A of Example 2a [Aβ(1-42) Oligomers A-CL]

10 µl of an Aβ(1-42) oligomer A solution prepared according to example 2a are diluted to 100 µM Aβ(1-42) content with 7.5 µl of PBS, 0.2% SDS. To this solution 1 µl of freshly prepared 10 mM glutardialdehyde solution in water is added, followed by stirring at RT for 3 h. The excess glutardialdehyde is saturated by adding 1 µl of 100 mM ethanolamine solution in water, pH 7.4, to the sample and stirring for 1 h. The preparation obtained in this way contains crosslinked Aβ(1-42) oligomers A and is referred to as Aβ(1-42) oligomer A-CL preparation.

EXAMPLE 14 a) Crosslinking of Aβ(1-42) Oligomers B of Example 5a [Aβ(1-42) Oligomers B-CL]

10 µl of an Aβ(1-42) oligomer B solution prepared according to example 5a are admixed with 1 µl of freshly prepared 10 mM glutardialdehyde solution in water and stirred at RT for 3 h. The excess glutardialdehyde is saturated by adding 1 µl of 100 mM ethanolamine solution in water, pH 7.4, to the sample and stirring for 1 h. The preparation obtained in this way contains crosslinked Aβ(1-42) oligomers B and is referred to as Aβ(1-42) oligomer B-CL preparation.

b) Alternative Procedure for Crosslinking Aβ(1-42) Oligomers [Aβ(1-42) Oligomers B-CL]

72.6 ml of an Aβ(1-42) oligomer B solution prepared according to example 5a are admixed with 7.26 ml of freshly prepared 10 mM glutardialdehyde solution in water and stirred at RT for 2 h. The excess glutardialdehyde is saturated by adding 726 µl of buffer (20 mM sodium phosphate, 140 mM NaCl, 500 mM ethanolamine, pH 7.4) to the sample and stirring at RT for 30 min. The reaction mixture is concentrated to 3 ml via a 15 ml 30 kDa Centriprep tube. The concentrate is removed by centrifugation at 10 000 g for 10 min. The supernatant is removed and dialyzed at 6° C. in a dialysis tube against 1 l of 5 mM sodium phosphate, 35 mM NaCl, pH 7.4 for 16 h. The dialysate is subsequently removed by centrifugation at 10 000 g for 10 min and the supernatant is removed and can be stored at −80° C. for further studies. The preparation obtained in this way contains crosslinked Aβ(1-42) oligomers B and is referred to as Aβ(1-42) oligomer B-CL preparation.

EXAMPLE 15 a) Preparation of Truncated Aβ(20-42) Oligomers, Starting from Aβ(1-42) Oligomers B, by Cleavage with Thermolysin 1.59 ml of Aβ(1-42) oligomer B preparation prepared according to example 6b are admixed with 38 ml of buffer (50 mM MES/NaOH, pH 7.4) and 200 µl of a 1 mg/ml thermolysin solution (Roche) in water. The reaction mixture is stirred at RT for 20 h. Then 80 µl of a 100 mM EDTA solution, pH 7.4, in water are added and the mixture is furthermore adjusted to an SDS content of 0.01% with 400 µl of a 1% strength SOS solution. The reaction mixture is concentrated to approx. 1 ml via a 15 ml 30 kDa Centriprep tube. The concentrate is admixed with 9 ml of buffer (50 mM MES/NaOH, 0.02% SDS, pH 7.4) and again concentrated to 1 ml. The concentrate is dialyzed at 6° C. against 1 l of buffer (5 mM sodium phosphate, 35 mM NaCl) in a dialysis tube for 16 h. The dialysate is adjusted to an SDS content of 0.1% with a 2% strength SDS solution in water. The sample is removed by centrifugation at 10 000 g for 10 min and the supernatant is removed.

The material thus obtained is analyzed further (SDS polyacrylamide gel electrophoresis; cf. FIG. 11); the mass-spectrometric analysis of the truncated oligomers produced reveals that the oligomer is composed of truncated Aβ(20-42).

b) Preparation of Truncated A8(12-42) Oligomers, Starting from Aβ(1-42) Oligomers B, by Cleavage with Endoproteinase GluC 2 ml of an Aβ(1-42) oligomer B preparation prepared according to example 6b are admixed with 38 ml buffer (5 mM sodium phosphate, 35 mM sodium chloride, pH 7.4) and 150 µl of a 1 mg/ml GluC endoproteinase (Roche) in water. The reaction mixture is stirred for 6 h at RT, and a further 150 µl of a 1 mg/ml GluC endoproteinase (Roche) in water are subsequently added. The reaction mixture is stirred at RT for another 16 h, followed by addition of 8 µl of a 5 M DIFP solution. The reaction mixture is concentrated to approx. 1 ml via a 15 ml 30 kDa Centriprep tube. The concentrate is admixed with 9 ml of buffer (5 mM sodium phosphate, 35 mM sodium chloride, pH 7.4) and again concentrated to 1 ml. The concentrate is dialyzed at 6° C. against 1 l of buffer (5 mM sodium phosphate, 35 mM NaCl) in a dialysis tube for 16 h. The dialysate is adjusted to an SDS content of 0.1% with a 1% strength SDS solution in water. The sample is removed by centrifugation at 10 000 g for 10 min and the supernatant is removed.

The material thus obtained is analyzed further (SDS polyacrylamide gel electrophoresis; cf. FIG. 11). Mass-spectrometric analysis of the truncated oligomer produced reveal that the oligomer is composed of truncated Aβ(12-42).

Characterization of A8(1-42) Oligomers

EXAMPLE 16

SDS Polyacrylamide Gel Electrophoresis (SDS PAGE)

The molecular weight under denaturing conditions is characterized by analyzing the preparations of examples 2a, 5a, 9, 12, 13 and 14a, all of which contain oligomers A and B, under denaturing conditions according to standard conditions in a 4-20% strength Tris-glycine SDS PAGE.

Figure 1:
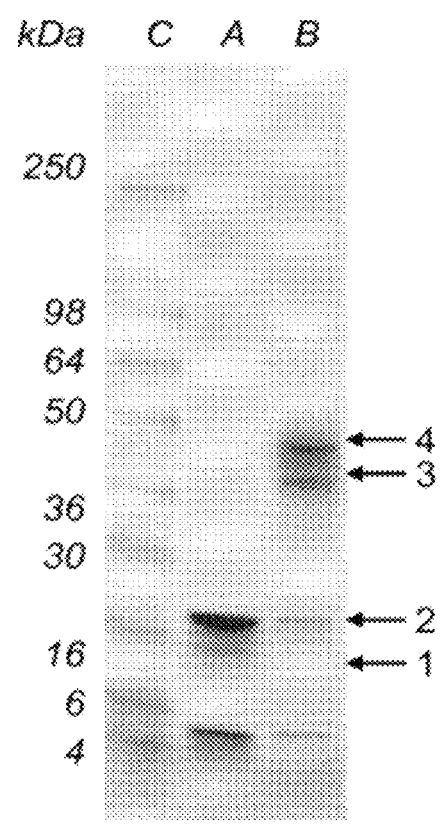
FIG. 1 shows an SDS PAGE of an Aβ(1-42) oligomer A preparation (lane A); an Aβ(1-42) oligomer B preparation (lane B); of standard proteins (molecular marker proteins, lane C)

The evaluation of said SDS PAGE (FIG. 1) reveals that starting protein Aβ(1-42) still present in the oligomer A preparation appears as a band at about 4 kDa, while the oligomers A1 and A2 of example 2a, denoted 1 and 2, respectively, in FIG. 1, are visible at about 15 kDa (weaker band) and at about 20 kDa (main band).

In the oligomer B preparation comparatively little starting protein Aβ(1-42) can be detected (relatively weak band at about 4 kDa). In contrast, the oligomers B1 and B2 of example 5a, denoted 3 and 4, respectively, in FIG. 1 appear at about 38 kDa and about 48 kDa (see arrows). Correspondingly higher molecular weights of about 42 kDa and about 52 kDa arise for the biotin- and fluorescein-derivatized oligomers B of examples 9 and 12 (FIGS. 3, 4).

Figure 2:
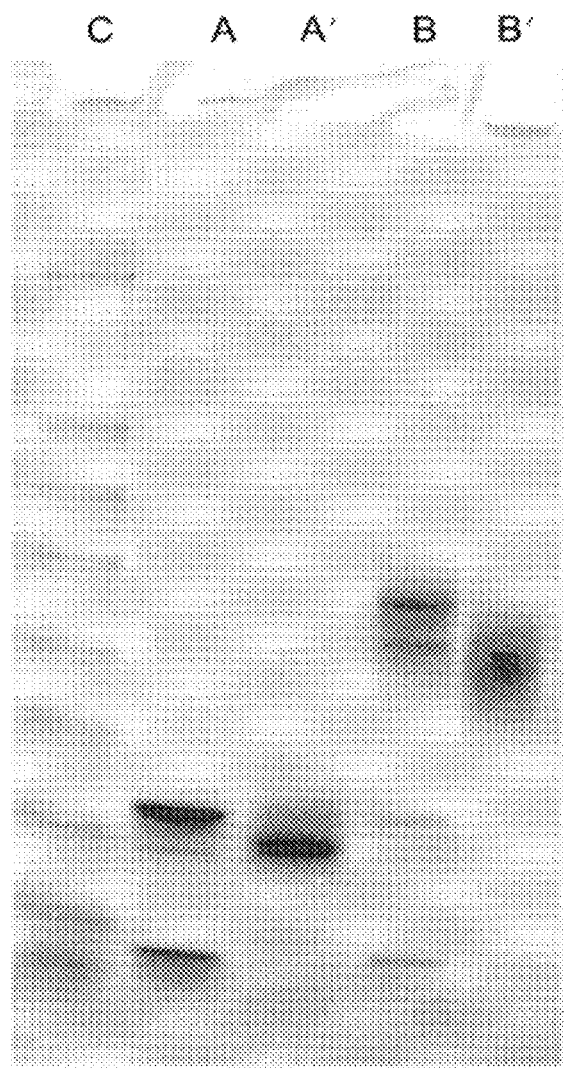
FIG. 2 shows an SDS PAGE of an Aβ(1-42) oligomer A preparation (lane A); an Aβ(1-42) oligomer A-CL preparation (lane A'); an Aβ(1-42) oligomer B preparation (lane B); an Aβ(1-42) oligomer B-CL preparation (lane B'); of standard proteins (molecular marker proteins, lane C)

Analysis of the preparations containing the respective crosslinking products A-CL and B-CL (examples 13 and 14a; FIG. 2) reveals that the two samples essentially maintain their degree of oligomerization (cf. lane A with A' and lane B with B'). The slightly different migration behavior compared to the oligomers A and B can be explained by a slightly altered SDS binding capacity and by modification of the amino groups of the N terminus and, respectively, the lysine residue.

Analysis of the truncated Aβ(20-42) oligomers (of Example 15a) reveals that the 38/48 kDa double band (FIG. 11, lane A) is converted to a 28/38 kDa double band (FIG. 11; lane B) by proteolytic removal of the N-terminal peptide with themolysine. Similarly, analysis of the truncated Aβ(12-42) oligomers (of Example 15b) reveals that the 38/48 kDa double band (FIG. 11; lane A) is converted to a 33/40 kDa double band (FIG. 11; ring C) by proteolytic removal of the N-terminal peptide with Glu-C endoprotease.

EXAMPLE 17

Gel Permeation Chromatography

In order to study the molecular weight behavior under nondenaturing conditions in more detail, a gel permeation chromatography (GPC) is carried out by way of an FPLC process using a Superose 12 HR10/30 column. The GPC is run at 4° C.

Figure 5A:
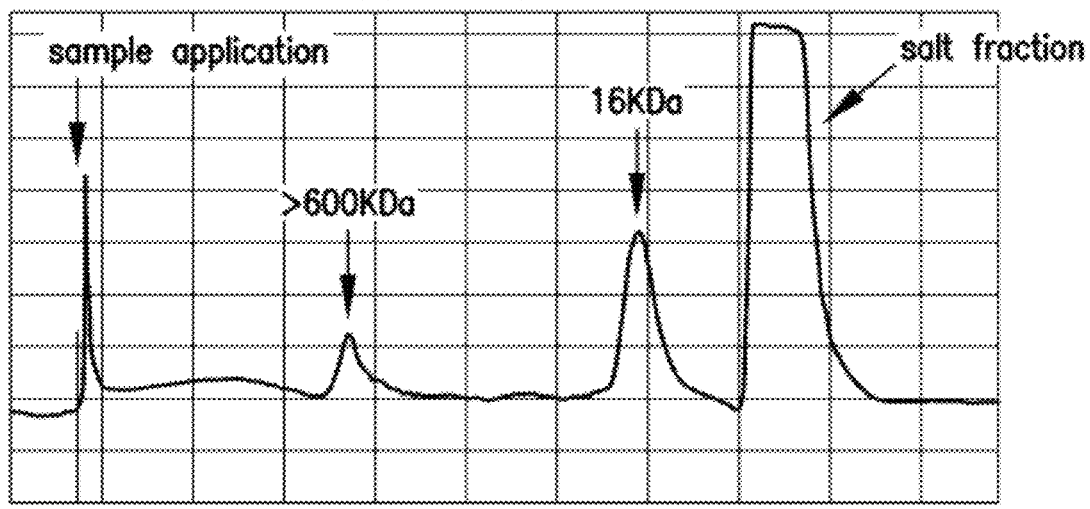
FIG. 5 shows a gel permeation chromatography of a solution containing Aβ(1-42) lyophilisate in comparison with a preparation containing Aβ(1-42) oligomers B.
Figure 5B:
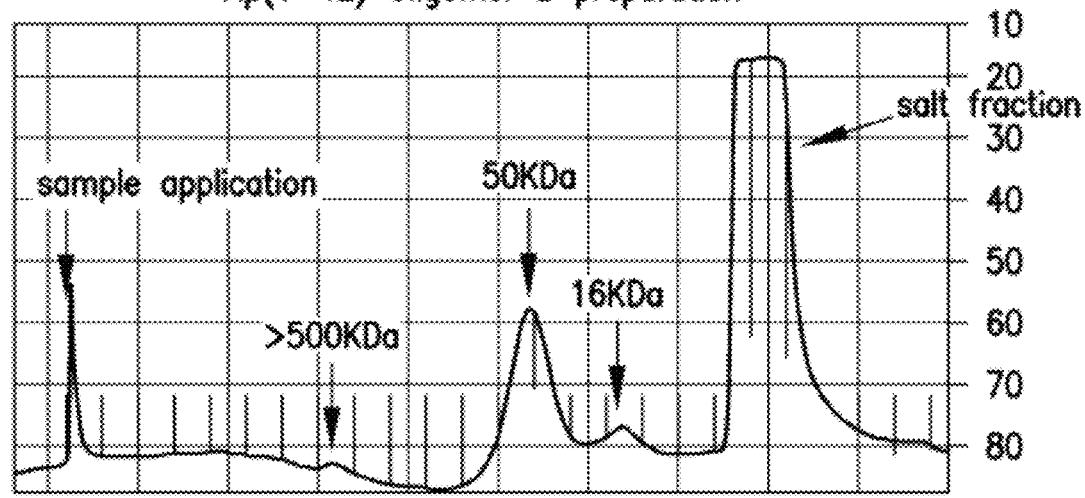

The column is equilibrated with 5 volumes of PBS buffer (flow rate 0.5 ml/min, UV detection, 214 nm) and first calibrated using protein standards. Subsequently, the Aβ(1-42) oligomer B preparation of example 5a (FIG. 5, bottom) and, for comparison, the same concentration of freshly weighed Aβ(1-42) lyophilisate dissolved in PBS are analyzed, after removing the insoluble components by centrifugation at 10 000 g for 5 minutes (FIG. 5, top).

The evaluation reveals that the Aβ(1-42) oligomer B preparation has a protein fraction characterized by a main peak in the molecular weight range of around approximately 50 kDa. As under denaturing conditions in the SDS PAGE, this protein fraction differs significantly from the monomeric Aβ(1-42) protein characterized by a main peak in the molecular weight range of around approximately 16 kDa.

In order to study the molecular weight behavior of Aβ(1-42) oligomers B of example 6b and of Aβ(1-42) oligomers B-CL of example 14a under nondenaturing conditions, a gel permeation chromatography (GPC) is carried out by way of an FPLC process using a Superose 12 HR10/30 column at room temperature. The column is equilibrated with 5 column volumes of PBS buffer (flow rate 0.5 ml/min, UV detection, 214 nm) and first calibrated using protein standards. Subsequently, Aβ(1-42) oligomer B of example 6b is diluted to 1 mg/ml with PBS buffer and Aβ(1-42) oligomer B-CL of example 14a is diluted to 1 mg/ml with PBS buffer, and both mixtures are analyzed (FIG. 12).

The evaluation reveals that the Aβ(1-42) oligomer B preparation with reduced SDS content has a protein fraction characterized by a main peak in the molecular weight range around approximately 100 kDa. In comparison therewith, the Aβ(1-42) oligomer B-CL preparation with reduced SDS content has a protein fraction characterized by a main peak in the molecular weight range around approximately 60 kDa.

EXAMPLE 18

Native Polyacrylamide Gel Electrophoresis (NATIVE PAGE) of Aβ(1-42) Oligomers B of Example 5a The molecular weight under native conditions is characterized by analyzing the oligomers B-containing preparations of example 5a under nondenaturing conditions in a 4-20% Tris-glycine gel.

The detergent present in the preparations is neutralized by the nonionic detergent Triton X-100. To this end, 1 μl (4% Triton X-100) is pipetted to 10 μl of the preparation of the example 5a and incubated at room temperature for 5 min. Subsequently, 10 μl are admixed with the same volume of native sample buffer (4 ml of 1M Tris, pH 6.8, 8 ml of glycerol, 1 ml of bromophenol blue in 50 ml of H$_2$O) and the electrophoresis (running buffer: 7.5 g of Tris, 36 g of glycine to 2.5 l of H$_2$O).

Figure 6:
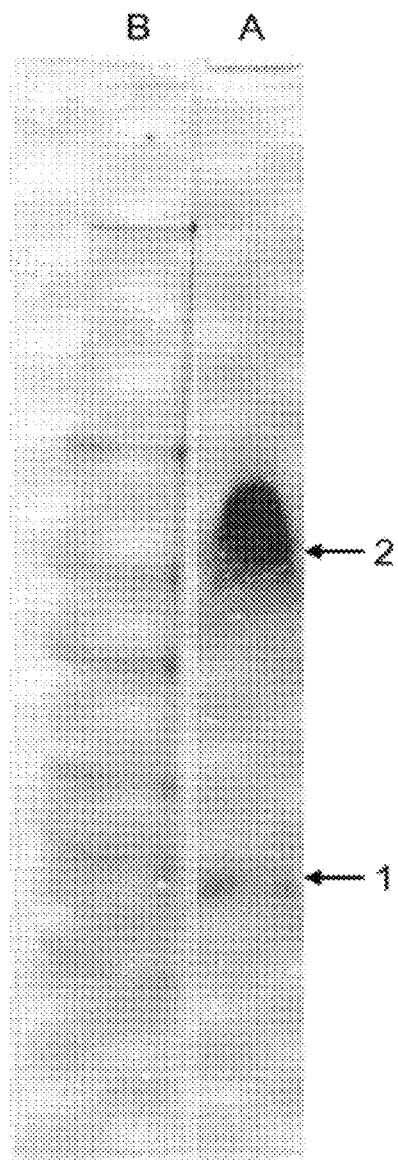
FIG. 6 shows a NATIVE PAGE of an Aβ(1-42) oligomer B preparation (lane A); of standard proteins (molecular marker proteins, lane B)

The NATIVE PAGE evaluation reveals that the starting peptide Aβ(1-42) still present in the oligomer B preparation appears as a band at about 28 kDa (lane A, denoted 1), while the main bands of the preparation of example 5a are visible at an apparent molecular weight of 64-90 kDa (lane A, denoted 2) (FIG. 6).

It is important that molecular weights can be assigned to the oligomers of the invention, in particular the oligomers B, also in native molecular weight analytical methods such as gel permeation chromatography (see example 17) or native gel electrophoresis (see example 18).

After complexing of the SDS, the oligomers B to which molecular weights of about 38 and 48 kDa can be assigned in the SDS PAGE are detected in the native gel electrophoresis as a band in the molecular weight range of about 64-90 kDa, based on selected standard proteins. This method cannot be expected to provide an exact reading of the molecular weight, since the migration behavior of the oligomers is substantially determined by their intrinsic charges, in addition to their size. However, the result leads to the conclusion that a defined oligomeric species is present.

EXAMPLE 19 a) Stability of Aβ(1-42) Oligomers B at Various Protein Concentrations in Physiological Buffers The Aβ(1-42) oligomers B obtained according to example 6b are tested for stability in PBS buffer under the following conditions.

5 mg/ml are diluted with PBS in 2× dilution steps down to 0.08 mg/ml. All solutions obtained are incubated at room temperature for 24 hours. This was followed by analyzing the band pattern in an SDS PAGE in comparison with a frozen control preparation. The band pattern is identical in all samples.

b) Stability of Aβ(1-42) Oligomers B at Various Temperatures and after Different Periods of Time in Physiological Buffers The Aβ(1-42) oligomers B obtained according to example 6b are diluted to 0.5 mg/ml with PBS buffer and incubated at room temperature or at 37° C. for 24 h or 96 h.

Subsequently, the band pattern was analyzed in an SDS PAGE. The band pattern is identical in all samples.

EXAMPLE 20

Proteolysis of Aβ(1-42) Oligomers B by Means of Various Proteases (Trypsin, Chymotrypsin, Thermolysin, Elastase, Papain)

Aliquots of the Aβ(1-42) oligomer B preparation obtained according to example 6b are diluted to 0.5 mg/ml with buffer (20 mM sodium phosphate, 140 mM NaCl, pH 7.4) and incubated with in each case 1/50 of the amount by weight of the protease solutions indicated in FIG. 9 under the following conditions at 37° C. and pH 7.4 for 20 h. 1 μg of reactive mixture aliquots are then analyzed in an SDS-PAGE (FIG. 9).

The SDS PAGE reveals that, starting from the Aβ(1-42) oligomers B preparation, all proteases revert the double band at about 38/48 kDa to a kDa double band at about 32/28 kDa under the chosen limited proteolysis conditions.

EXAMPLE 21

Stability of Aβ(1-42) oligomers B in Rat Plasma

4 μl of the Aβ(1-42) oligomer B preparation prepared according to example 6b are incubated with 76 μl of rat plasma at room temperature for 0 h, 1 h, 2 h, 4 h and 8 h. The incubations are stopped by freezing in dry ice.

Subsequently, all samples are analyzed in an SDS PAGE, after addition of SDS sample buffer. This is followed by an evaluation of the stability via staining of the Aβ(1-42) oligomers B in a Western blot. The anti-Aβ(1-42) antibody 6E10 (Signet) was used for detection. The bands are made visible by an anti-mouse IgG antibody coupled to alkaliphosphatase and addition of the substrate NBT/BCIP. Both molecular weight and intensity of the observed band pattern remain nearly unchanged over a period of 2 h, 4 h and 8 h.

This result suggests that the Aβ(1-42) oligomers B have high plasma stability. According to this, the biological half life in the plasma is in the range of about 8 hours or longer.

EXAMPLE 22

Figure 7A:
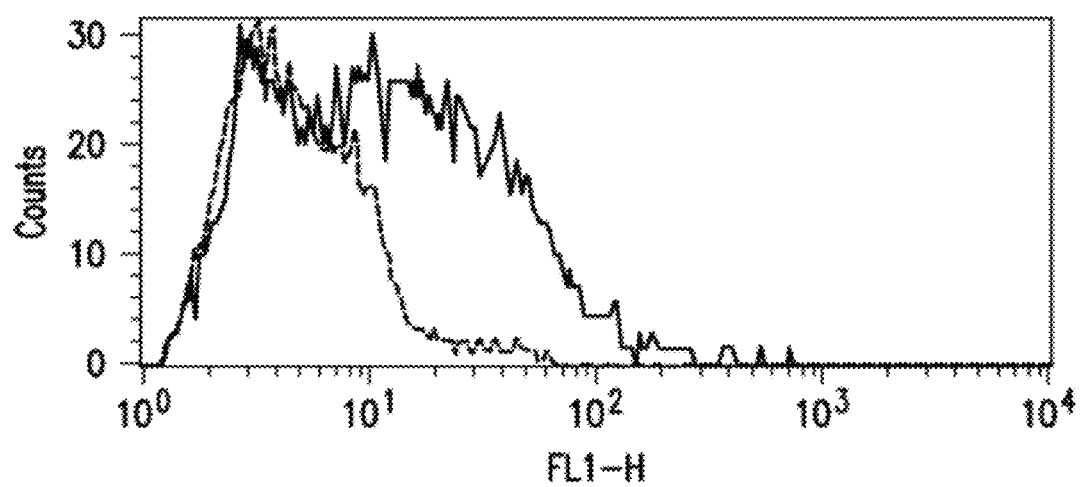
FIG. 7 shows the binding of (A) monomeric Aβ(1-42) protein and (B) of the Aβ(1-42) oligomers A and (C) Aβ(1-42) oligomers B to the surface of the human neuroblastoma cell line IMR-32.
Figure 7B:
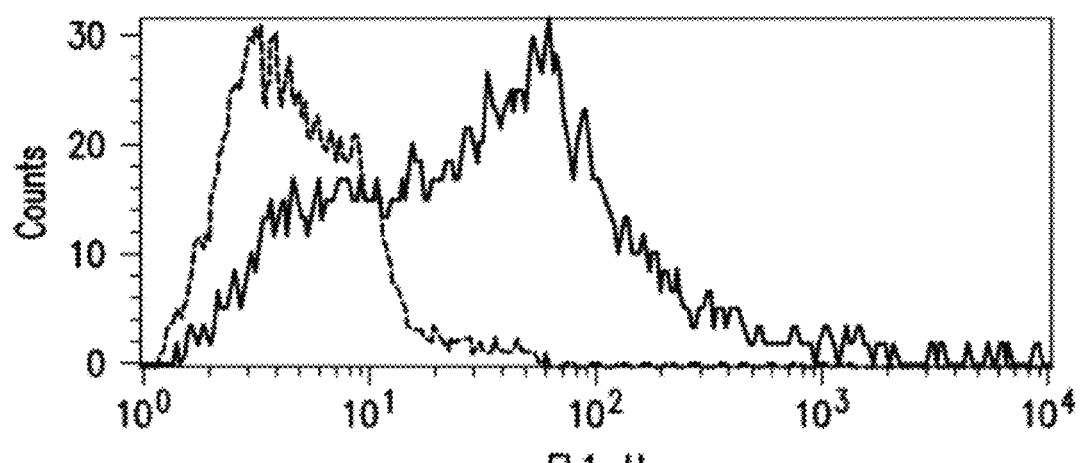
Figure 7C:
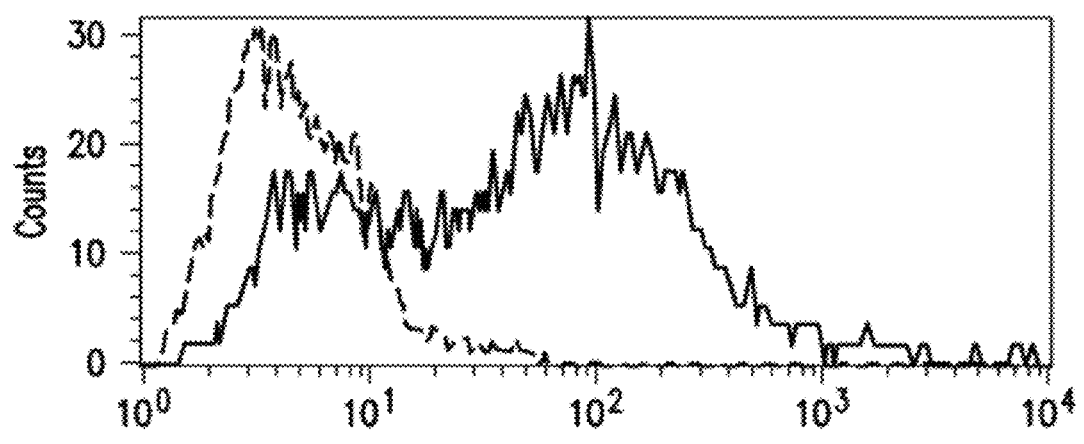

Binding of Biotin-Aβ(1-42) Oligomers Having Molecular Weights of 17 KDa and 22 KDa [Biotin-Aβ(1-42) Oligomers A] and, Respectively, of 42 KDa and 52 KDa [Biotin-Aβ(1-42) Oligomers B] to the Surface of Human Neuronal Cells Binding of human β-amyloid(1-42) protein and the two Aβ(1-42) oligomer A and Aβ(1-42) oligomer B preparations to the human neuroblastoma cell line IMR-32 (ATCC Number: CCL-127) is studied by means of FACScan (Beckton Dickinson). A suspension of IMR-32 cells ($1.5 \times 10^6$ cells/0.1 ml PBS) is incubated with biotin-labeled human β-amyloid (1-42) protein (peptide-synthetic material, lyophilisate, AnaSpec) and the preparations containing the biotin-labeled oligomers A and B (examples 8 and 9, respectively) at 37° C. for 20 minutes. The cells are subsequently washed with buffer (PBS plus 1% BSA) and incubated at room temperature with fluorescein coupled to streptavidin isothiocyanate (Sigma) for 20 minutes. After a washing step with buffer, binding to the surface of IMR-32 cells was analyzed by FACScan. The dashed line indicates background fluorescence in the absence of the biotin-labeled components. The addition of the individual preparations resulted in a strong increase of cell-associated fluorescence and is represented by the thick line. Binding of the oligomers A (FIG. 7B) and B (FIG. 7C) to the cell surfaces is distinctly different from the binding of the monomeric β-amyloid(1-42) protein (FIG. 7A). The data indicate specific binding sites for said oligomers on human cell surfaces.

EXAMPLE 23

Detection of Aβ(1-42) Oligomers B in Rat Brain Homogenates after icv Administration 10 nmol of an Aβ(1-42) oligomer B preparation obtained according to example 6b are administered as icv-bolus to rats. The brains are prepared after 15 min and 120 min, respectively. Brains of untreated control animals are likewise prepared. For this purpose, in each case 1 g of rat brain is admixed with 9 ml of disruption buffer A (200 ml of 5 mM sodium phosphate, 35 mM NaCl, 300 mM sucrose, adjusted to pH 7.4, are admixed with 4 tablets of Complete® protease inhibitor cocktail from Roche) in a 50 ml Falcon tube and disrupted under ultrasound (UltraTurrax) on ice for 2 min. The solution is left standing for 20 min, then shaken briefly and divided into 8×1 ml aliquots (=homogenate).

In order to carry out quantitative detection, first a series of standards of the Aβ(1-42) oligomer B preparation in PBS in the concentration range of 1.58 ng/μl-0.005 ng/μl is prepared.

Furthermore, as a positive control, a homogenate from a control brain of an untreated rat is also processed and a series of standards of the Aβ(1-42) oligomer B preparation is prepared in this brain homogenate in the same way. The homogenates are then introduced in an ultracentrifuge at 100 000 g for 1 h and the supernatants are used for the subsequent analyses.

From the comparison of the values measured on both series of standards (PBS versus control brain-homogenate supernatant), the Aβ(1-42) oligomer B content can be determined quantitatively as follows, first in the positive control and then, in comparison therewith, also in the brain sample of treated rats.

1) Detection by Dot Blot 1 it drops of the series of standards samples and of the sample extracts from the treated animals are applied to nitrocellulose paper, and Aβ(1-42) is detected using the antibody 6E10 (anti-Aβ(1-42); Signet). Staining is carried out using an alkaliphosphatase coupled to anti-mouse IgG and by adding the staining reagent NBT/BCIP.

While no Aβ(1-42) (0.01 nmol/g) is detectable in the brain extracts of untreated rats, about 0.4 nmol/g Aβ(1-42) can be detected in the rats sacrificed 15 min after treatment by comparing the staining intensity with the corresponding concentrations of the positive control, and approx. 0.2 nmol/g can still be detected by the same method in the rats sacrificed 120 min after treatment. This results in an average biological half life of about 105 min for the exogenously administered Aβ(1-42) oligomers B.

2) Detection by Western Blot

All dot blot-analyzed samples are likewise analyzed in a Western blot. The Western blot is likewise developed with mMAb 6E10 (anti-Aβ(1-42); Signet) and furthermore with an alkaliphosphatase coupled to anti-mouse IgG and by adding the staining reagent NBT/BCIP.

Anti-Aβ(1-42) reactive bands only occur in the 38/48 kDa region, corresponding to the apparent molecular weight of the Aβ(1-42) oligomers B, i.e. the oligomeric structure is still retained with in vivo administration, even after 2 hours.

Furthermore, as in the dot blot method, the same concentrations can be estimated in the brains of the 15 min rats (0.4 nmol/g) and the 120 min rats (0.2 nmol/g) by comparing the staining intensities with correspondingly intensively stained bands of the Aβ(1-42) oligomers B in the positive control.

EXAMPLE 24

Figure 8:
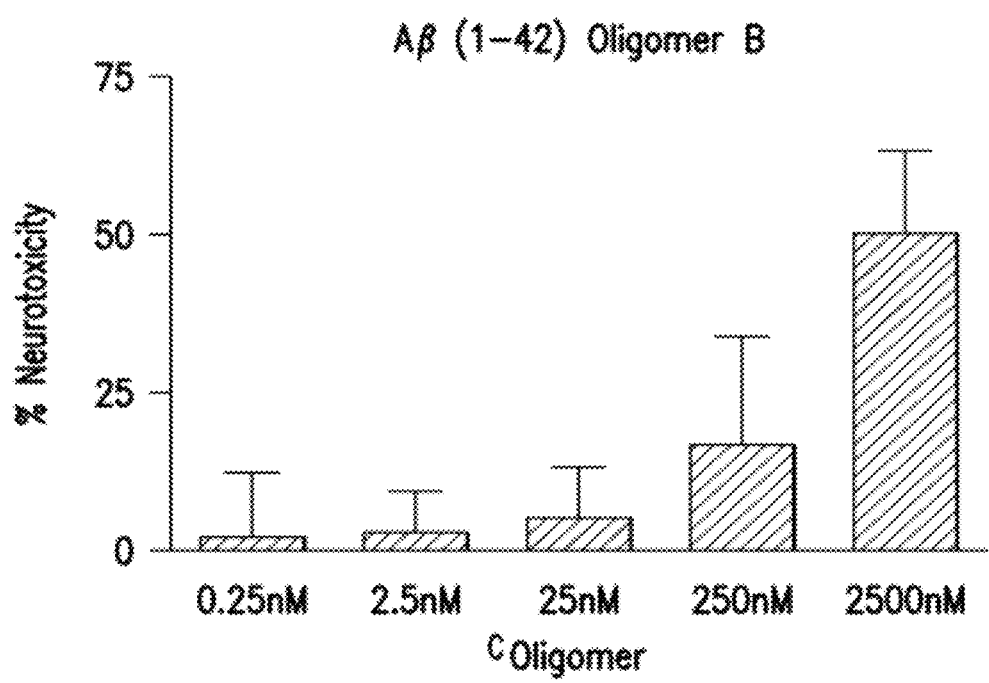
FIG. 8 shows the neurotoxic effect in % after treatment of murine cortical neurons with Aβ(1-42) oligomers B, the error bar corresponding to the 95% confidence interval.

Neurotoxic Action of Aβ(1-42) Oligomers Having Molecular Weights of 38 KDa and 48 kDa [Aβ(1-42) Oligomers B] on Murine Cortical Neurons Murine cortical neurons are prepared and cultured as a mixed culture with glia cells following the literature (Choi et al. (1987) J. Neurosci. 7, 357-368). The cortices of embryos on days 14-15 of development are mechanically removed from the meninges and lower brain regions. The cells are separated from one another by incubation in a 0.05% strength trypsin solution at 37° C. for 5-7 minutes and subsequently pipetting said solution several times through a pasteur pipette with reduced opening. After determining the number of cells, 430 000 cells are seeded in 0.5 ml of maintenance medium (minimum essential medium containing 0.8 mM glutamine, 18 mM glucose, 23 mM NaHCO$_3$ and 10% of horse serum) per 2 cm$^2$ on cell culture material coated with poly-L-ornithine and laminine. Cultivation and later incubations of the cells are carried out in a humidified cell culture incubator at 37° C., 5% CO$_2$. After 3-5 days in culture, propagation of the glia cells is interrupted by a 1-day incubation with a mixture of (+)-5-fluoro-2'-deoxyuridine/uridine (10 μM each). After 14 days in culture, the toxic action of Aβ(1-42) oligomers B is studied. For this purpose, the cells are incubated in brain cell buffer (120 mM NaCl, 5.4 mM KCl, 1.8 mM CaCl$_2$, 15 mM glucose, 25 mM HEPES, pH 7.2) for 15 minutes. Control cells 1 are incubated with 300 μM L-glutamate in brain cell buffer for the same time. The Aβ-oligomer stock solution is diluted with serum-free medium (minimum essential medium containing 0.8 mM glutamine, 20 mM glucose, 26 mM NaHCO$_3$) to various final concentrations and incubated for 24 h. The L-glutamate-treated control cells 1 are incubated in parallel in serum-free medium. Another group of cells (control cells 2) is treated only with brain cell buffer and serum-free medium. The cell culture supernatants are removed after 24 h, the remaining cells are destroyed by incubation in distilled water for 20 minutes and the activity of the enzyme lactate dehydrogenase (LDH) is determined enzymatically in both solutions. For evaluation, the ratio of the LDH activity of the cell culture supernatants to the sum of the LDH activities of supernatant and remaining cells is determined and the average of the quadruple determinations is formed. 3 experiments are carried out, with each experimental condition being present in quadruplicate (n=12). The average for the glutamate-treated cells (control cells 1) is set to 100% neuronal death, the average of the cells which have been treated neither with L-glutamate nor with A13 oligomers (control cells 2) is set to 0% neuronal death and the values of the cells treated with Aβ oligomers are converted accordingly. The neurotoxicity average of all determinations at the concentrations used in each case indicates a distinct toxic action of the Aβ(1-42) oligomers having molecular weights of 38 kDa and 48 kDa [Aβ(1-42) oligomer B], cf. FIG. 8.

EXAMPLE 25

Production of Antibodies

The cocktails used for immunization contain in all cases adjuvant (Biogenes) with essentially the following components:
95% Paraffin oil
2.4% Tween 40
0.1% Cholesterol
0.1% Lipopolysaccharide
The adjuvant is mixed with a solution of the antigen in a 2:1 ratio until a stable emulsion is obtained. The emulsion is injected and forms a depot from which said antigen is released steadily.

a) Production of Polyclonal Antisera by Immunization of Rabbits with Truncated Aβ(20-42) Oligomers B of Example 15a 2 rabbits are immunized with unconjugated Aβ(20-42) oligomer B preparation of example 15a according to a standard protocol:
Day 1 Primary immunization and taking of preimmune serum
Day 7 First boost
Day 14 Second boost
Day 28 Third boost and bleeding
Day 35 Taking blood
The antisera are obtained from the rabbit's blood by letting the latter stand at room temperature and subsequent centrifugation at room temperature. The serum obtained in this way is referred to as serum (a1).
2 mg of Aβ(20-42) oligomer B preparation of example 15a are coupled to LPH with glutardialdehyde under standard conditions and 2 more rabbits are immunized with this conjugated Aβ(20-42) oligomer B according to a standard protocol:
Day 1 Primary immunization and taking of preimmune serum
Day 7 First boost
Day 14 Second boost
Day 28 Third boost and bleeding
Day 35 Taking blood
The antisera are obtained from the rabbit's blood by letting the latter stand at room temperature and subsequent centrifugation at room temperature. The serum obtained in this way is referred to as serum (a2).

b) Production of Polyclonal Antisera by Immunization of Rabbits with Truncated Aβ(12-42) Oligomers B of Example 15b 2 rabbits are immunized with unconjugated Aβ(12-42) oligomer B preparation of example 15b according to a standard protocol:
Day 1 Primary immunization and taking of preimmune serum
Day 7 First boost
Day 14 Second boost
Day 28 Third boost and bleeding
Day 35 Taking blood
The antisera are obtained from the rabbit's blood by letting the latter stand at room temperature and subsequent centrifugation at room temperature. The serum obtained in this way is referred to as serum (b1).
2 mg of Aβ(12-42) oligomer B preparation of example 15b are coupled to LPH with glutardialdehyde under standard conditions and 2 more rabbits are immunized with this conjugated Aβ(12-42) oligomer B according to a standard protocol:
Day 1 Primary immunization and taking of preimmune serum
Day 7 First boost
Day 14 Second boost
Day 28 Third boost and bleeding
Day 35 Taking blood
The antisera are obtained from the rabbit's blood by letting the latter stand at room temperature and subsequent centrifugation at room temperature. The serum obtained in this way is referred to as serum (b2).

c) Production of Polyclonal Antisera by Immunization of Rabbits with Aβ(1-42) Oligomer Preparation B-CL of Example 14a 2 rabbits are immunized with unconjugated Aβ(1-42) oligomers B-CL preparation of example 14a according to a standard protocol:
Day 1 Primary immunization and taking of preimmune serum
Day 7 First boost
Day 14 Second boost
Day 28 Third boost and bleeding
Day 35 Taking blood
The antisera are obtained from the rabbit's blood by letting the latter stand at room temperature and subsequent centrifugation at room temperature. The serum obtained in this way is referred to as serum (c1).

d) Production of Polyclonal Antisera by Immunization of Rabbits with Aβ(1-42) Oligomer Preparation B of Example 6b 2 rabbits are immunized with unconjugated Aβ(1-42) oligomers B preparation of example 6b according to a standard protocol:
Day 1 Primary immunization and taking of preimmune serum
Day 7 First boost
Day 14 Second boost
Day 28 Third boost and bleeding
Day 35 Taking blood
The antisera are obtained from the rabbit's blood by letting the latter stand at room temperature and subsequent centrifugation at room temperature. The serum obtained in this way is referred to as serum (d1).
2 mg of Aβ(1-42) oligomer B preparation of example 6b are coupled to LPH, with glutardialdehyde under standard conditions and 2 more rabbits are immunized with this conjugated Aβ(1-42) oligomer B preparation according to a standard protocol:
Day 1 Primary immunization and taking of preimmune serum
Day 7 First boost
Day 14 Second boost
Day 28 Third boost and bleeding
Day 35 Taking blood The antisera are obtained from the rabbit's blood by letting the latter stand at room temperature and subsequent centrifugation at room temperature. The serum obtained in this way is referred to as serum (d2).

EXAMPLE 26

Characterization of Polyclonal Antisera from the Immunizations of Example 25 Regarding their Cross Reaction with Various Aβ(1-42) Forms In order to characterize the polyclonal antisera, serial dilution in the range of 100 pmol/µl-0.01 pmol/µl of the various Aβ(1-42) forms were prepared in PBS. In each case 1 µl of the sample was applied to a nitrocellulose membrane: detection was carried out using the appropriate rabbit sera of example 25. A detection using mMAb 6E10 (Signet) was carried out for comparison. Alkaliphosphatase coupled to anti-rabbit IgG (for comparison: alkaliphosphatase coupled to anti-mouse IgG) was used for staining together with addition of the staining reagent NBT/BCIP. FIG. 10 indicates the dot blots obtained in this manner, which can be numerically evaluated as follows:

| Antigen | 6E10 | Serum (a1) | Serum (a2) | Serum (d1) | Serum (c1) |
|---|---|---|---|---|---|
| Oligomer | 0.1 | 0.5 | 10 | 0.1 | 0.5 |
| Monomer | 0.1 | 10 | 100 | 0.1 | 1 |
| Fibril | 1 | 100 | >100 | 0.5 | 1 |
| APP | 0.01 | >1 | 1 | 0.1 | 0.1 |
| Aβ (1-40)* | 0.1 | 100 | n.d. | 0.5 | 10 |

*not shown in FIG. 10

The numbers in the table indicate the minimum amount of antigen visible [in pmol; in each case based on the monomer, except for APP] (detection limit).

Comparison of the immunological reactions with rabbit serum (a1) obtained by immunization with unconjugated Aβ(20-42) oligomer of example 15a clearly indicates that the antibodies directed against these oligomers cross-react only weakly with the other forms such as fibrils, APP and monomer. In contrast, a markedly stronger cross reaction with the Aβ(1-42) oligomer B (see row 1) and, moreover, a cross reaction with the stabilized CL antigen are observed. This data indicates a distinctly different structure of the oligomer form present here, in comparison with APP, monomer and the fibril structure. The antibodies bind to oligomer-specific structures.

The immunological reactions with rabbit serum (a2) obtained by immunization with conjugated Aβ(20-42) oligomer of example 15a likewise show that antibodies directed against these oligomers cross-react only weakly with the other forms such as fibrils and monomer. In contrast, a weak cross reaction with the Aβ(1-42) oligomer B (see row 1) and, moreover, a cross reaction with the stabilized CL antigen and with APP are observed. This data indicates a likewise distinctly-different structure of the oligomer form present here, in comparison with monomer and the fibril structure.

In comparison therewith, the immunological reactions with rabbit serum (d1) obtained by immunization with Aβ(1-42) oligomer of example 6b, and also with rabbit serum (c1) obtained by immunization with Aβ(1-42) oligomer B-CL of example 14a indicate that the antibodies directed against these oligomers cross-react with the other forms such as fibrils, APP and monomer comparably as strongly as with the Aβ(1-42) oligomers B (see row 1). These antibodies exhibit an immune reaction comparable to that of mMAb 6E10 (Signet) and do not bind to oligomer-specific structures.

Correspondingly, mice were immunized with Aβ(1-42) oligomers of example 6b and monoclonal antibodies established in a manner known per se. Here, 2 out of 10 hybridomas secreted monoclonal antibodies whose binding profiles are similar to those of the antiserum (a1), in particular with respect to the reactivites assayed above.

EXAMPLE 27

Preparation of Aβ(1-42) Fibrils

100 µl of 2 mg/ml Aβ(1-42) solution in 0.1% NH$_4$OH are diluted with 300 µl of buffer (20 mM sodium phosphate, 140 mM NaCl, pH 7.4) to 0.5 mg/ml and adjusted to pH 7.4 with 0.1 M HCl (100 µM Aβ(1-42)). The sample is incubated at 37° C. for 24 h and then removed by centrifugation at 10 000 g for 10 min. The protein residue obtained is resuspended with 400 µl of buffer (20 mM sodium phosphate, 140 mM NaCl, pH 7.4). The Aβ(1-42) fibril preparation obtained in this way can be stored at −20° C. and used for further studies.

EXAMPLE 28

Effects of Aβ(1-42) Oligomers B-CL (of example 14b) on Hippocampal Slices

Transversal hippocampal slices of 400 µM in thickness were adapted in a submersion slice chamber at 34° C. under perfusion by gassed Ringer's solution (NaCl 124 mM, KCl 4.9 mM, MgSO$_4$ 1.3 mM, CaCl$_2$ 2.5 mM, KH$_2$PO$_4$ 1.2 mM, NaHCO$_3$ 25.6 mM, glucose 10 mM). Subsequently, the Schaffer collateral was stimulated with the aid of a monopolar stimulating electrode and the excitatory postsynaptic potential (fEPSP) in the stratum radiatum was recorded. Test pulses were given with 30% of the stimulus level that generates a maximum fEPSP. Long-term potentiation was induced by applying 100 pulses three times every 10 minutes, with single pulses having a width of 200 µs (strong tetanus). The resulting potentiation of the fEPSPs was recorded for at least 240 minutes. The rinsing-in of the oligomer B-CL of example 14b (500 nM) started 20 minutes before the first tetanus and was stopped 10 minutes after the last tetanus. The rise (slope) of the fEPSPs was determined and plotted as a function of time.

FIG. 14 indicates that the washing-in of Aβ(1-42) oligomers suppresses long-term potentiation in hippocampus, especially in the maintenance phase. Accordingly, the Aβ(1-42) oligomers BCL influence the storage of information by nerve cells (cellular memory).

EXAMPLE 29

Binding of Aβ(1-42) Oligomers B (of Example 5b) to Rat Primary Hippocampal Neurons The binding of rat Aβ(1-42) oligomers B of example 5b to rat primary hippocampal neurons was studied. The hippocampal neurons were cultured in neurobasal medium with B27 supplement on poly-L-lysine-coated cover slips and used on day 14 of the culture. The oligomers were bound to the cell membrane of the neurons by adding 200 nM (total monomeric Aβ concentration) oligomers to fresh culture medium and incubating at 37° C. for 15 minutes. After removing the Aβ-containing medium, two washing steps with medium were carried out and the cells were then fixed in 3.7% formaldehyde. After further washing of the cells, unspecific binding sites were blocked with 10% normal donkey serum in PBS buffer at room temperature for 90 min. 6E10 (from mouse) was applied as the first antibody in a 1:2000 dilution at room temperature for 2 h. The cells were washed again and incubated with the second antibody (from donkey) which is directed against mouse and which is coupled to the fluorescent dye Cy3, at room temperature for 2 h. After the cells had been washed again, the cover slips containing the neurons were fixed to a slide with embedding medium. The hippocampal neurons with bound Aβ oligomers were depicted in a fluorescent microscope. The control used was a mixture in which the first antibody 6E10 had been omitted. This control thus exhibits unspecific fluorescence not based on A13.

Figure 15A:
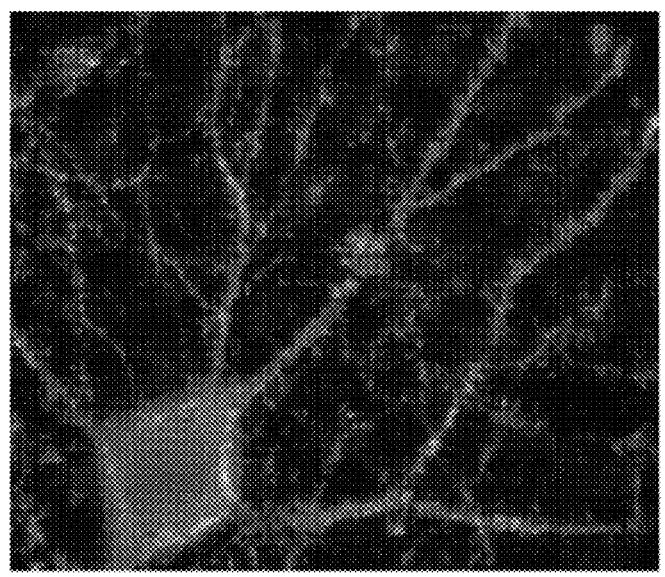
Figure 15B:

As FIG. 15a shows, the oligomers bind to the cell surface of the neurons in a dotted manner. In contrast, the control without the first antibody 6E10 exhibits only low unspecific fluorescence, due to binding of the second antibody to the neurons (FIG. 15b).

wherein the N-terminal truncated Aβ(1-42) oligomer is produced by a process comprising:
   i) exposing a monomeric Aβ(1-42) protein to a detergent to form an intermediate oligomer;
   ii) reducing the detergent action and further incubating the intermediate oligomer to form an Aβ(1-42) oligomer; and
   iii) treating the Aβ(1-42) oligomer with a protease to form the N-terminal truncated Aβ(1-42) oligomer,
wherein the detergent is a compound of formula R—X, wherein the radical R is unbranched or branched alkyl having from 6 to 20 carbon atoms or unbranched or branched alkenyl having from 6 to 20 carbon atoms, and the radical X is an acidic group or salt thereof.

2. The isolated antibody of claim 1, which binds the N-terminal truncated Aβ(1-42) oligomer with an affinity greater than $K_d = 10^{-8}$ M.

3. The isolated antibody of claim 1, which binds monomeric Aβ(1-42) protein and/or monomeric Aβ(1-40) protein with an affinity of less than $K_d = 10^{-8}$ M.

The invention claimed is:

1. An isolated antibody which binds an N-terminal truncated amyloid-β ("Aβ")(1-42) oligomer comprising an Aβ(X-42) fragment, wherein X is 10 to 24, the isolated antibody obtainable by a method comprising:
   a) immunizing a host with the N-terminal truncated Aβ(1-42) oligomer; and
   b) obtaining an antibody-containing host serum produced as a response to said immunization,
wherein the isolated antibody binds the N-terminal truncated Aβ(1-42) oligomer with 10-fold greater affinity than an amyloid derived, diffusible and dementing ligand (ADDL), 4. The isolated antibody of claim 1, wherein the affinity of said antibody to the N-terminal truncated Aβ(1-42) oligomer is at least 10 times greater than to monomeric Aβ(1-42) protein and/or monomeric Aβ(1-40) protein.

5. The isolated antibody of claim 1, which binds the N-terminal truncated Aβ(1-42) oligomer with a rate constant $k_{off}$ of 0.1 $S^{-1}$ or lower, as determined by means of surface plasmon resonance.

6. A pharmaceutical agent, comprising the isolated antibody of claim 1 and, optionally, a pharmaceutically suitable carrier.

7. The isolated antibody of claim 1, wherein the fragment is selected from Aβ(12-42), Aβ(13-42), Aβ(14-42), Aβ(15-42), Aβ(16-42), Aβ(17-42), Aβ(18-42), Aβ(19-42), and Aβ(20-42).

8. The isolated antibody of claim 1, wherein the fragment is an Aβ(20-42) fragment.

9. The isolated antibody of claim 8, wherein the protease is thermolysin.

10. The isolated antibody of claim 1, wherein the Aβ(1-42) oligomer has an apparent molecular weight of about 38 kDa and/or about 48 kDa on SDS gel electrophoresis.

11. The isolated antibody of claim 1, wherein the radical X is selected from among $-COO^-M^+$, $-SO^{3-}M^+$, and $-OSO^{3-}M^+$, wherein $M^+$ is a hydrogen cation or an inorganic or organic cation selected from alkali metal and alkaline earth metal cations and ammonium cations.

12. The isolated antibody of claim 1, wherein the detergent is sodium dodecyl sulfate.

\* \* \* \* \*